United States Patent
Mason et al.

(10) Patent No.: US 6,392,121 B1
(45) Date of Patent: May 21, 2002

(54) GEMINI VIRUS VECTORS FOR GENE EXPRESSION IN PLANTS

(75) Inventors: Hugh S. Mason, Ithaca, NY (US); Kenneth E. Palmer, Vacaville, CA (US); Kathleen L. Hefferon, Ithaca, NY (US); Tsafrir S. Mor, Ithaca, NY (US); Charles Arntzen, Ithaca, NY (US)

(73) Assignee: Boyce Thompson Institute for Plant Research, Ithaca, NY (US)

( * ) Notice: Subject to any disclaimer, the term of this patent is extended or adjusted under 35 U.S.C. 154(b) by 0 days.

(21) Appl. No.: 09/414,276

(22) Filed: Oct. 7, 1999

Related U.S. Application Data
(60) Provisional application No. 60/103,352, filed on Oct. 7, 1998.

(51) Int. Cl.$^7$ .......................... C12N 5/04; C12N 15/82; C12N 15/87; C12N 15/90

(52) U.S. Cl. ................ 800/287; 435/320.1; 435/252.3; 435/252.33; 435/469; 435/468; 435/410; 435/411; 435/412; 435/414; 435/415; 435/417; 435/430; 435/470; 536/23.1; 536/23.2; 536/23.6; 536/24.1; 800/278; 800/280; 800/293; 800/295; 800/298; 800/312; 800/317.2; 800/317.3; 800/317.4; 800/320.1; 800/320.2; 800/320.3

(58) Field of Search ......................... 435/320.1, 252.3, 435/252.33, 469, 468, 410, 411, 412, 414, 415, 417, 430, 470; 536/23.1, 23.2, 23.6, 24.1; 800/278, 287, 280, 293, 295, 298, 312, 317.2, 317.3, 317.4, 320.1, 320.2, 320.3

(56) References Cited

U.S. PATENT DOCUMENTS

| | | |
|---|---|---|
| 5,589,379 A | 12/1996 | Kridl |
| 5,650,303 A | 7/1997 | Kridl |
| 6,077,992 A | 6/2000 | Yadav |

OTHER PUBLICATIONS

Arntzen et al. (1997) "Oral vaccine production in the edible tissues of transgenic plants." In: *New Generation Vaccines*, Second Edition (Eds. Levine MM, Woodrow GC, Kaper JB, Cobon GS) Marcel Dekker, New York, pp. 263–277.
Atkinson et al. (1998) *The Plant Journal*, 15(5):593–604.
Caddick et al. (1998) *Nature Biotechnology* 16:177–180.
Carrington et al. (1990) "Cap–independent enhancement of translation by a plant potyvirus 5' nontranslated region," *J. Virol.* 64: 1590–1597.
Christou et al. (1990) "Soybean genetic engineering—commercial production of transgenic plants," *Trends Biotechnol.* 8:145–151.

Clements et al. (1988) "Adjuvant activity of *Escherichia coli* heat–labile enterotoxin and effect on the induction of oral tolerance in mice to unrelated protein antigens," *Vaccine* 6:269–277.
Clough et al. (1998) *The Plant Journal* 16(6):735–743.
Collin et al. (1996) *Virology* 219:324–329.
Cregg et al. (1987) "High level expression and efficient assembly of hepatitis B surface antigenin the methulotrophic yeast *Pichia pastoris*," *Bio/Technology* 5:479–485.
Delkman et al. (1992) *Plant Physiol.* 100:2013–2017.
Di Tommaso et al. (1996) "Induction of antigen–specific antibodies in vaginal secretions by using a nontoxic mutant of heat–labile eneterotoxin as a mucosal adjuvant," *Infect. Immun.* 64:974–979.
Doyle et al. (1996) "The glycosylated seed storage proteins of *Glycine max* and *Phaseolus vulgaris*. Structural homologies of genes and proteins," *J. Biol. Chem.* 261:9228–9238.
Elmer et al. (1990) *Nucleic Acids Research* 18:8.
Giovannoni, et al. (1989) "Expression of a chimeric polygalacturonase gene in transgenic rin (ripening inhibitor) tomato fruit results in polyuronide degradation but not fruit softening," *Plant Cell* 1, 53–63.
Guerche et al. (1990) *The Plant Cell.* 2:469–478.
Goddijn et al. (1995) "Plants as bioreactors," *Trends Biotechnol.* 13:379–387.
Hanley–Bowdoin et al. (1988) "Transient expression of heterologous RNAs using tomato golden mosaic virus," *Nucl. Acids Res.* 16: 10511.
Hanley–Bowdoin et al. (1990) "Expression of functional replication protein from tomato golden mosaic virus in transgenic tobacco plants," *Proc. Natl. Acad. Sci. USA* 87: 1446–1450.
Haq et al. (1995) "Oral immunization with a recombinant bacterial antigen produced in transgenic plants," *Science* 268:714–716.

(List continued on next page.)

Primary Examiner—David Guzo
(74) Attorney, Agent, or Firm—Kathleen M. Williams; Palmer & Dodge, LLP

(57) ABSTRACT

A gene amplification system based on plant viral genetic elements dramatically increases foreign protein production in plants. A safer and more economical production system for vaccines and antibodies in recombinant plants grown using agricultural practice is described. The high-level expression system uses the replicative process of a plant mastrevirus, exemplified by bean yellow dwarf virus (BeYDV). The expression system is preferably inducible to avoid interference with plant growth and development. Developmental cues, such as fruit ripening, are employed to trigger expression of the foreign protein using a tissue-specific promoter. A single, stably integrated expression cassette for foreign protein is replicated extrachromosomally in ripening fruit, forming hundreds of transcriptionally competent copies. Preferred plant hosts include tomato as a model system and soybean for production of large quantities of protein at high total protein levels.

66 Claims, 44 Drawing Sheets

OTHER PUBLICATIONS

Hayes et al. (1988) "Gene amplification and expression in plants," *Nature* 334: 179–182.

Hayes et al. (1989) "Stability and expression of bacterial genes in replicating geminivirus vectors in plants," *Nucl. Acids Res.* 17: 2391–2403.

Hiatt et al. (1989) "Production of antibodies in transgenic plants," *Nature* 342:76–78.

Hood et al. (1997) "Commercial production of avidin from transgenic maize: characterization of transformant, production, processing, extraction and purification," *Molecular Breeding* 3:291–306.

Iida et al. (1995) "Positive and negative cis–regulatory regions in the soybean glycinin promoter identified by quantitative transient gene expression," *Plant Cell Reports* 14: 539–544.

Jefferson et al. (1987) "GUS fusions: β–glucuronidase as a sensitive and versatile gene fusion marker in higher plants," *EMBO J.* 13:3901–3907.

Jiang et al. (1992) "Expression, self–assembly, and antigenicity of the Norwalk virus capsid protein," *J. Virol.* 66:6527–6532.

Kanevski et al. (1992) "Tobacco lines with high copy numbers of replicating recombinant geminivirus vectors after biolistic delivery," *Plant J.* 2: 457–463.

Kuntz et al. (1997) "Polymeric controlled delivery for immunization," *Trends Biotechnol.* 15:364–369.

Kusnadi et al. (1997) "Production of recombinant proteins in transgenic plants: practical considerations," *Biotechnol. Bioeng.* 56: 473–484.

Laufs et al. (1995) *Biochemie* 77:765–773.

Liu et al. (1997) "Molecular characterization of a Subgroup I geminivirus from a legume in South Africa," *J. Gen. Virol.*, 78: 2113–2117.

Liu et al. (1998) *Journal of General Virology*, 79:2265–2274.

Liu et al. (1999) *Journal of General Virology*, 80:501–506.

Ma et al. (1995a) "Generation and assembly of secretory antibodies in plants," *Science* 268: 716–719.

Ma et al. (1995b) "Plant antibodies for immunotherapy," *Plant Physiol.* 109:341–346.

Maniatis et al. (1982) *Molecular Cloning: A Laboratory Manual.* Cold Spring Harbor Laboratory, 1982.

Mason et al. (1988) "Proteins homologous to leaf storage proteins are abundant in stems of soybean seedlings. Analysis of proteins and cDNAs," *Plant Mol. Biol.* 11;845–856.

Mason et al. (1992) "Expression of hepatitis B surface antigen in transgenic plants," *Proc. Natl. Acad. Sci. USA* 89:11745–11749.

Mason et al. (1995) "Transgenic plants as vaccine production systems," *Trends Biotechnol.* 13:388–392.

Mason et al. (1996) "Expression of Norwalk virus capsid protein in transgenic tobacco and potato and its oral immunogenicity in mice," *Proc. Natl. Acad. Sci. USA* 93:5335–5340.

Mason et al. (1998) "Edible vaccine protects mice against *E. coli* heat–labile enterotoxin (LT): potatoes expressing a synthetic LT–B gene," *Vaccine*, 16:1336–1343.

Montgomery et al. (1993) *The Plant Cell* 5:1049–1062.

Needham, et al. (1998) *Plant Cell Reports* 17: 631–639.

Palmer K. (1997a) "The use of geminiviruses in biotechnology and plant molecular biology, with particular focus on Mastreviruses," *Plant Science* 129:115–130.

Palmer et al. (1997b) "Molecular biology of Mastreviruses". *Advances in Virus Research* 50: 183–234.

Palmer et al. (1997c) "Geminivirus isolation and DNA extraction". In: *Plant Virology Protocols* (Series: Methods in Molecular Biology). (S. Taylor and G. Foster (Eds) Totowa, NJ: Humana Press.

Palmer et al. (1999) *Archives of Virology* 144:1345–1360.

Penarrubia et al. (1992), *Bio/Technology* 10:561–564.

Rojas et al. (1998), *Cell*, vol. 95, p105–113.

Shah et al. (1995) "Resistance to diseases and insects in transgenic plants: progress and applications to agriculture," *Trends Biotechnol.* 13:362–368.

Shen et al. (1991) *Virology* 183:721–730.

Sijmons et al. (1990) "Production of correctly processed human serum albumin in transgenic plants," *Bio/Technology* 8:217–220.

Stanley et al. (1990) "Defective viral DNA ameliorates symptoms of geminivirus infection in transgenic plants," *Proc. Natl. Acad. Sci. USA* 87: 6291–6295.

Stenger et al. (1991) "Replicational release of geminivirus genomes from tandemly repeated copies: evidence for rolling–circle replication of a plant viral DNA," *Proc. Natl. Acad. Sci. USA* 88:8029–8033.

Stewart et al. (1996) "Genetic transformation, recovery, and characterization of fertile soybean transgenic for a synthetic *Bacillus thuringiensis* cryIAc gene," *Plant Physiol.* 112: 121–129.

Sugrue et al. (1997) "Expression of the dengue virus structural proteins in *Pichia pastoris* leads to the generation of virus–like particles," *J. Gen. Virol.* 78:1861–1866.

Thanavala et al. (1995) "Immunogencity of transgenic plant–derived hepatitis B surface antigen," *Proc. Natl. Acad. Sci. USA* 92: 3358–3361.

Timmermans et al. (1994) "Geminiviruses and their use as extrachromosomal replicons," *Annu. Rev. Plant Physiol. Plant Mol. Biol.* 45: 79–112.

Vitale et al. (1984) "Biosynthesis and processing of phytohemagglutinin in developing bean cotyledons," *Eur. J. Biochem.* 141:97–104.

Zambryski P. (1988) "Basic processes underlying Agrobacterium–mediated DNA transfer to plant cells," *Annu. Rev. Genet.* 22:1–30.

C1 →
AGGCATGTGTTGTGACTCCGAGGGTGCCTCAAATCTATCTATAA
CCGGCCGTGGAGGCAAGGGCATTTGGTAATTTAAGTAGTT
AGTGGAAAATGACGTCATTTACTAAAGACGAAGTCTTGCGACAAGGG
GGGCCCACGCCGAATTTAATATTACC<u>GGGTGG</u>CCCACCTTATCGC
GAGTGCTTAGCACGAGGGTCCAGATTTAAAGTAGAAAAGTCCCGC
CCACTAGGGTAAAGGGTGTTCACACTATAAAGCATATACGATGTGATG
GTATTTGATGGAG
 ←V1→

FIG. 2 pBY017 pBY002

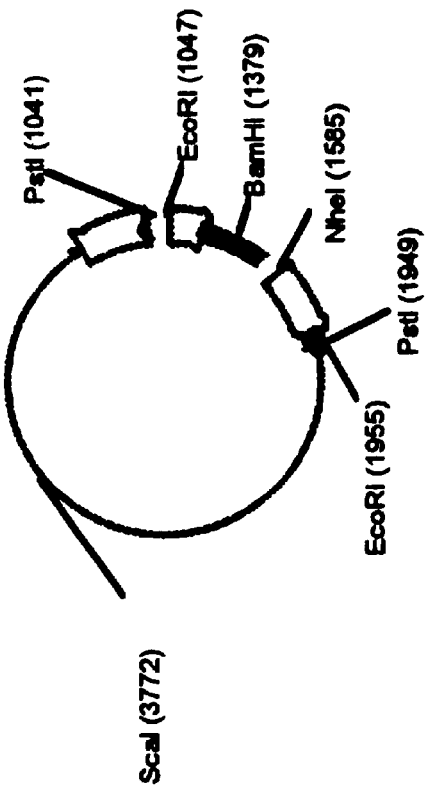
FIG. 5D pBY020
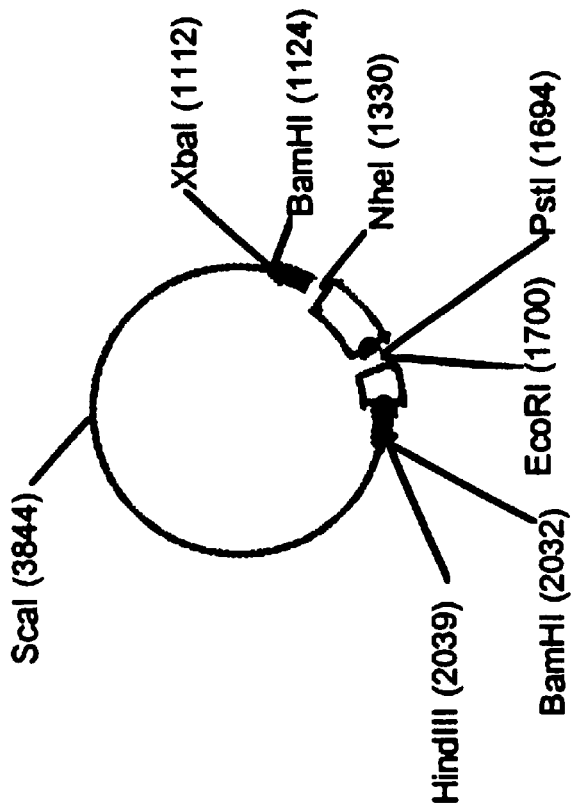
FIG. 5C pBY019

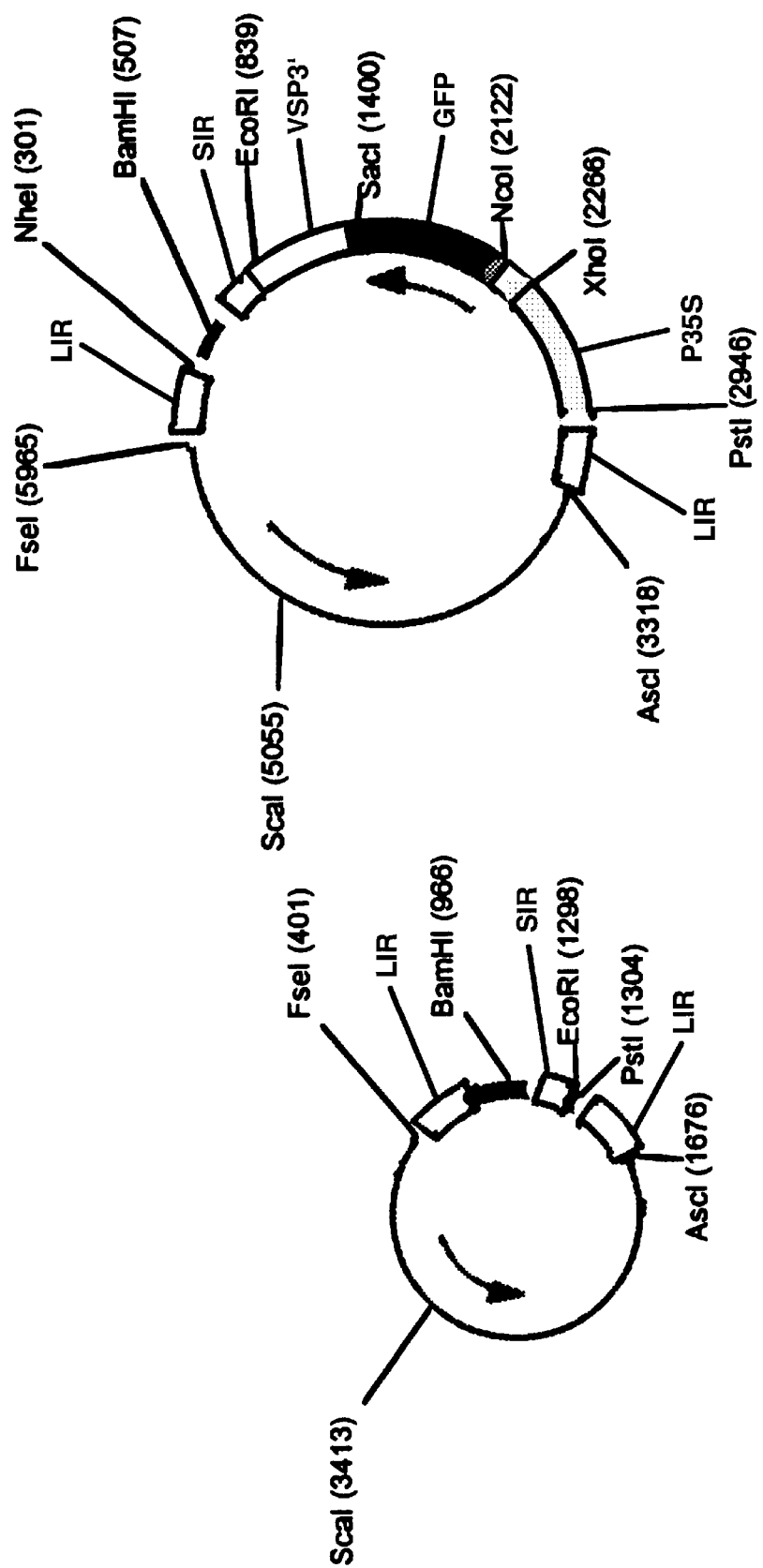
FIG. 5F pBY027
FIG. 5E pBY024

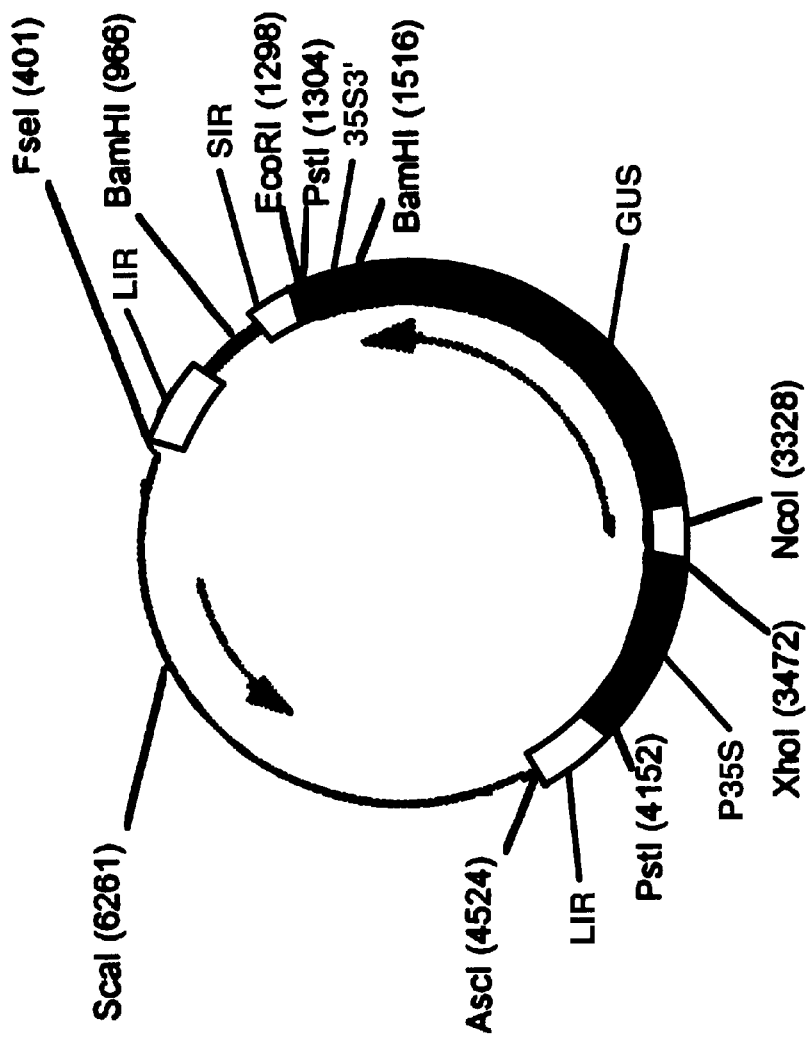
FIG. 5G pBY028

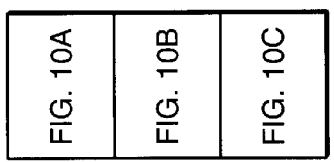

FIG. 10

```
         NcoI
  1 CCATGGGACCCTTCTGCTAGCAAGAACTTCAGACTCCAATCTAAATATGTTTTCCTTACCTACCCAAGTGC
 C1 > M  G  P  S  A  S  K  N  F  R  L  Q  S  K  Y  V  F  L  T  Y  P  K  C

72 TCATCTCAAAGAGATGATTTATTCCAGTTTCTCTGGGAGAAACTCACACCTTTTCTTATTTTCTTCCTTGG
  > S  S  Q  R  D  D  L  F  Q  F  L  W  E  K  L  T  P  F  L  I  F  F  L  G

143 TGTTGCTTCTGAGCTTCATCAAGATGGCACTACCCACTATCATGCTCTTATCCAGCTTGATAAAAAACCTT
  > V  A  S  E  L  H  Q  D  G  T  T  H  Y  H  A  L  I  Q  L  D  K  K  P
      BamHI

214 GTATTAGGGATCCTTCTCTTTTTTCGATTTTGAAGGAAATCACCCTAATATCCAGCCAGTAGAAACTCTAAA
  > C  I  R  D  P  S  F  F  D  F  E  G  N  H  P  N  I  Q  P  A  R  N  S  K
```

FIG. 10A

285 CAAGTCCTTGATTACATATCAAAGGACGGAGATATTAAAACCAGAGGAGATTCCGAGATCATAAGGTCTC
    >Q  V  L  D  Y  I  S  K  D  G  D  I  K  T  R  G  D  F  R  D  H  K  V  S

356 TCCTCGCAAATCTGACGCACGATGGCGAACTATATCCAGACTGCAACGTCTAAGGAGGAGTATCTTGACA
    >P  R  K  S  D  A  R  W  R  T  I  Q  T  A  T  S  K  E  E  Y  L  D
                       EcoRI                HindIII 427 TGATCAAAGAAGAATTCCCTCATGAATGGCAACAAAGCTTCAATGGCTGGAATATTCAGCCAACAAATTA
    >M  I  K  E  E  F  P  H  E  W  A  T  K  L  Q  W  L  E  Y  S  A  N  K  L 498 TTTCCTCCACAACCTGAGCAGTACGTGTGCCCTTCACAGAATCAGATCTCCGCTGCCACGAAGATCTGCA
    >F  P  P  Q  P  E  Q  Y  V  S  P  F  T  E  S  D  L  R  C  H  E  D  L  H 569 CAACTGGAGAGAGACGCACCTATATCATGTAAGCATCGATGCCTACACTTTCATACATCCTGTCTCCTACG
    >N  W  R  E  T  H  L  Y  H  V  S  I  D  A  Y  T  F  I  H  P  V  S  Y
                                        ClaI 640 ATCAAGCACACAATCTGACCTTGAGTGGATGGCCGATCTAACCAGGATGAGGGAAGGACTGGGGGTCAGACACC
    >D  Q  A  Q  S  D  L  E  W  M  A  D  L  T  R  M  R  E  G  L  G  S  D  T
                              C2 > D  G  R  S  N  Q  D  E  G  R  T  G  V  R  H

FIG. 10B

```
 711  CCAGCCTCTACATCTGCGGACCAACTCGTACCGGAAAGACCACCTGGGCTAGAAGTCTCGGGCGACACAAC
    > P  S  L  Y  I  C  G  P  T  R  T  G  K  T  T  W  A  R  S  L  G  R  H  N

782  TACTGGAACGGGACCATCGACTTCACCAACTACGATGAACACGCCACCTATAATATCATCGACGACATCCC
    > Y  W  N  G  T  I  D  F  T  N  Y  D  E  H  A  T  Y  N  I  D  D  I  P

853  CTTCAAGTTCGTCCCATTGTGGAAGCAATTAATAGGTTGCCAGTCTGATTTCACTGTCAACCCTAAATATG
    > F  K  F  V  P  L  W  K  Q  L  I  G  C  Q  S  D  F  T  V  N  P  K  Y
    > P  S  S  S  S  H  C  G  S  N
                          BamHI

924  GAAAAAAAGAAGAAAATAAAAGGTGGGATCCCTTCTATAATTCTTTGGAATCCTGACGAAGACTGGATGTTA
    > G  K  K  K  K  I  K  G  G  I  P  S  I  I  L  W  N  P  D  E  D  W  M  L

995  TCAATGACAAGTCAACAGAAGGATTACTTTGAAGATAATTGCGTCACCCACTATATGTGTGACGGGGAGAC
    > S  M  T  S  Q  Q  K  D  Y  F  E  D  N  C  V  T  H  Y  M  C  D  G  E  T
                                                        SacI

1066  TTTTTTTGCTCGGGAATCGTCGAGTCACTGAACGTGCCTGAGCTC
    > F  F  A  R  E  S  S  S  H  TER
```

|FIG. 18A|
|FIG. 18B|

FIG. 18

```
     NcoI
  1  CCATGGGACCTTCTGCTAGCAAGAACTTCAGACTTCCAATCTAAATATGTTTCCTTACCTACCCCAAGTGCTCAT
     M  G  P  S  A  S  K  N  F  R  L  Q  S  K  Y  V  F  L  T  Y  P  K  C  S

76  CTCAAAGAGATGATTTATTCCAGTTTCTCTGGGAGAAACTCACACCTTTTCTTATTTCTTCCTTGGTGTTGCT
     S  Q  R  D  D  L  F  Q  F  L  W  E  K  L  T  P  F  L  I  F  F  L  G  V  A
                BamHI

150  TCTGAGCTTCATCAAGATGGCACTACCCACTATCATGCTCTTATCCAGCTTGATAAAAAACCTTGTATTAGGGA
     S  E  L  H  Q  D  G  T  T  H  Y  H  A  L  I  Q  L  D  K  K  P  C  I  R  D

224  TCCTTCTTTTTTCGATTTTGAAGGAAATCACCCTAATATCCAGCCAGTAGAAACTCTAAACAAGTCCTGATT
     P  S  F  F  F  D  F  E  G  N  H  P  N  I  Q  P  A  R  N  S  K  Q  V  L  D

298  ACATATCAAAGGACGGAGATATTAAAACCAGAGGAGATTTCCGAGATCATAAGGTCTCCTCCTCGCAAATCTGAC
     Y  I  S  K  D  G  D  I  K  T  R  G  D  F  R  D  H  K  V  S  P  R  K  S  D
                                                                    EcoRI

372  GCACGATGGCGAACTATTATCCAGACTGCAACGTCTAAGGAGGAGTATCTTGACATGATCAAAGAAGAATTCCC
     A  R  W  R  T  I  I  Q  T  A  T  S  K  E  E  Y  L  D  M  I  K  E  E  F  P
```

FIG. 18A

```
     BspHI        HindIII
446  TCATGAATGGGCAACAAAGCTTCAATGGCTGGAATATTCAGCCAACAATTATTCCTCCACAACCTGAGCAGT
      H  E  W  A  T  K  L  Q  W  L  E  Y  S  A  N  K  L  F  P  P  Q  P  E  Q
                                                                              BspH1
520  ACGTGTCGCCCTTCACAGAATCAGAGATCTCCGCTGCCGTGCACGAAGATCTGCACAACTGGAGAGAGACGCACCTATAT
      Y  V  S  P  F  T  E  S  D  L  R  C  H  E  D  L  H  N  W  R  E  T  H  L  Y 594  CATGATGAGGGAAGGACTGGGGGTCAGAGACACCCCAGCCTCTACATCTGCGGACCAACTCGTACCGGAAAGACCACC
      H  D  E  G  R  T  G  V  R  H  P  S  L  Y  I  C  G  P  T  R  T  G  K  T  T 669  TGGGCTAGAAGTCTCGGGGCGACACAACTACTGGAACGGAGACCATGACTTCACCAACTACGATGAACACGCCAC
      W  A  R  S  L  G  R  H  N  Y  W  N  G  T  I  D  F  T  N  Y  D  E  H  A  T 743  CTATAATATCATCGACGACATCCCCCTTCAAGTTCGTCCATTGTGGAAGCAATTAATAGGTTGCCAGTCTGATT
      Y  N  I  I  D  D  I  P  F  K  F  V  P  L  W  K  Q  L  I  G  C  Q  S  D
                                                                                BamHI
817  TCACTGTCAACCCTAAATATGGAAAAAAAGAAAATAAAGGTGGATCCCTTCTATAATTCTTTGGAATCCT
      F  T  V  N  P  K  Y  G  K  K  K  K  I  K  G  G  I  P  S  I  I  L  W  N  P 891  GACGAAGACTGGATGTTATCAATGACAAGTCAACAGAAGGATTACTTTGAAGATAATTGCGTCACCCACTATAT
      D  E  D  W  M  L  S  M  T  S  Q  Q  K  D  Y  F  E  D  N  C  V  T  H  Y  M
                                                                              SacI
965  GTGTGACGGGGAGACTTTTTTGCTCGGGAATCGTCGAGTCACTGAACGTGCCTGAGCTC
      C  D  G  E  T  F  F  F  A  R  E  S  S  S  H Ter
```

FIG. 18B

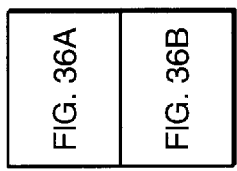

FIG. 36

```
                                                                BstXI
NcoI
  1 CCATGGACAAGAGGCTCTTCATCTCCCATGTGATCCTCCATCTTTGCACTCATCTTGGTGATCTCTACCCCCAATG
    >M  D  K  R  L  F  I  S  H  V  I  L  I  F  A  L  I  L  V  I  S  T  P  N
    >
 76 TGTTGGCAGAGAGCCAACCAGACCCTAAGCCAGATGAGTTGCATAAGAGCAGCAAGTTCACTGGTCTCATGGAGA
    >V  L  A  E  S  Q  P  D  D  P  K  P  D  E  L  H  K  S  S  K  F  T  G  L  M  E
151 ACATGAAGGTGCTCTATGATGACAACCATGTGTCAGCAATCAATGTGAAGTCTATTGACCAATCCCTCTACTTTG
    >N  M  K  V  L  Y  D  D  N  H  V  S  A  I  N  V  K  S  I  D  Q  S  L  Y  F
226 ACCTCATCTACTCTATCAAGGACACTAAGTTGGGAAACTATGACAATGTGAGGGTGGAGTTCAAGAACAAGGACT
    >D  L  I  Y  S  I  K  D  T  K  L  G  N  Y  D  N  V  R  V  E  F  K  N  K  D
```

FIG. 36A

```
301 TGGCTGACAAGTACAAGGACAAGTATGTGGATGTGTTTGGAGCTAACTACTATTACCAATGCTACTTCTCTAAGA
    >L  A  D  K  Y  K  D  K  Y  V  D  V  F  G  A  N  Y  Y  Y  Q  C  Y  F  S  K

376 AAACCAATGACATCAACAGCCACCAAACTGACAAGAAAGACTTGCATGTATGGTGGTGACTGAGCACAACG
    >K  T  N  D  I  N  S  H  Q  T  D  K  R  K  T  C  M  Y  G  G  V  T  E  H  N

451 GAAACCAATTGGACAAATACAGGAGCATCACTGTGAGGGTGTTTGAGGATGGTAAGAACCTCCTCTTTGATG
    >G  N  Q  L  D  K  Y  R  S  I  T  V  R  V  F  E  D  G  K  N  L  L  S  F  D

526 TGCAAACTAACAAGAAGAAGGTGACTGCTCAAGAGTTGGACTACCTCACTAGGCACTACTTGGTGAAGAACAAGA
    >V  Q  T  N  K  K  K  V  T  A  Q  E  L  D  Y  L  T  R  H  Y  L  V  K  N  K

601 AGCTCTATGAGTTCAACAACAGCCCTTATGAGACTGGATACATCAAGTTCATTGAGAATGAGAACAGCTTCTGGT
    >K  L  Y  E  F  N  N  S  P  Y  E  T  G  Y  I  K  F  I  E  N  E  N  S  F  W

676 ATGACATGATGCCTGCACCAGGAGACAAGTTTGACCAATCTAAGTACCTCATGATGTACAATGAC
    >Y  D  M  M  P  A  P  G  D  K  F  D  Q  S  K  Y  L  M  M  Y  N  D

741 AACAAGATGGTGGACTCTAA GGATGTGAAGATTGAGGTGT ACCTTACCACCAAGAAGAAG
    >N  K  M  V  D  S  K  D  V  K  I  E  V  Y  L  T  T  K  K  K
                       SacI
801 TAAgtcttcgagctc
    Ter
```

FIG. 36B

GEMINI VIRUS VECTORS FOR GENE EXPRESSION IN PLANTS

This application claims priority to Provisional Application No. 60/103,352, filed Oct. 7, 1998.

This invention was made using U.S. goverment funds and therefore the government has certain rights in the invention.

TECHNICAL FIELD

The present invention is related to genetic engineering of plants. The invention is particularly related to the transformation of plants using recombinant DNA techniques to amplify a gene of interest and express a protein of interest.

BACKGROUND OF THE INVENTION

A predominant mode of plant transformation employs *A. tumefaciens*, in which a transforming DNA (T-DNA) is modified to incorporate a desired foreign gene. The recombinant T-DNA contains the desired foreign gene between flanking non-coding regulatory sequences and the left and right border regions of the wild-type tumor-inducing (Ti) plasmid. The recombinant T-DNA can be provided as part of an integrative plasmid, which integrates into a wild-type Ti plasmid by homologous recombination. Typically, however, the recombinant T-DNA is provided in a binary vector and transferred into a plant cell through the action of trans-acting vir genes on a helper Ti plasmid. The T-DNA integrates randomly into the nuclear genome with some of the transformants permitting expression of the desired protein (Zambryski, 1988). Because of the random integration event of the T-DNA into the nuclear chromosome, variability of transcription level is expected, and transformants are screened to identify those showing the highest levels of foreign gene expression. Those transformants expressing the highest levels of foreign protein can be propagated and multiplied in tissue culture before transplanting to soil.

Many plant species previously recalcitrant to gene transfer are now amenable, including cereal crops (McElroy et al., 1994). Plants have the capacity to express foreign genes from a wide range of sources, including viral, bacterial, fungal, insect, animal, and other plant species. In single-copy nuclear transgenics, foreign protein in excess of 1% of total protein is often achieved (Hiatt et al., 1989). Further, assembly and processing of complex animal proteins in plants is possible, e.g., human serum albumin (Sijmons et al., 1990) and secretory antibodies (Ma et al., 1995a). Recently, expression of correctly processed avidin was reported in corn seed at a level of 2% of the total soluble protein (Hood et al., 1997). It has been estimated that the cost of recombinant protein production in plants (assuming the foreign protein is 10% of total protein) can be 10 to 50 times less than in *E. coli* by fermentation (Kusnadi et al., 1997).

Plants have been used as expression systems for vaccine antigens (Mason et al., 1995). The expression of vaccine antigens in tobacco plants has been reported and the plant material has been shown to be orally immunogenic in mice (work reviewed by Mason et al., 1995; Arntzen et al., 1996). Complex antibodies have also been expressed in plants, which correctly processed and assembled the antibody chains into IgG and secretory IgA forms (review by Ma et al., 1995b). In the latter case, four different genes were coordinately expressed, including the IgA heavy and light chains, the joining component, and the secretory component, which faithfully assembled in plant cells. Further, expression and accumulation of antibodies in corn and soybean seeds has been reported.

However, a major limitation in the use of plants for expression and delivery of a protein of interest is the rather low level of expression usually obtained, which ranges from 0.01% to 2% of the total soluble protein. For example, soybeans contain 40% protein by weight, yet current methods for foreign protein expression yield no more than 2% of the total protein in seeds. Synthetically produced recombinant vaccine proteins, which avoid the hazards associated with using live or attenuated virus, can be produced in cell culture systems, e.g., hepatitis B surface antigen (Cregg et al., 1987) and dengue virus proteins (Sugrue et al., 1997). However, the cost of cell culture systems is often so high as to preclude vaccination on a large scale, particularly in poor countries.

In applications requiring overexpression of a purified protein of interest, high-level expression would greatly facilitate the purification process. Therefore, a method of amplifying a gene of interest and overproducing a protein of interest in recombinant plants is desired.

Previous techniques are, however, inherently self-limiting by virtue of "successful" transformation affording only one or a few functional copies of the foreign gene integrated into the plant genome. Efforts to increase the level of expression under such circumstances are therefore limited to optimizing the promoter and/or enhancer sequences, using synthetic versions of the foreign gene optimized for expression in the plant host, optimizing the termination sequence, optimizing expression of transcription factors, and the like. These measures can be expected to enhance expression of the desired antigen, although such enhancement is still limited by the copy number of the foreign gene. True "amplification" of the foreign gene in plant cells, in which multiple functional copies of the gene are generated either extrachromosomally or integrated into the plant chromosome, is desired if much greater levels of protein expression are to be achieved. The geminiviruses are interesting candidates for producing marked amplification of transgenes in plants.

Members of the plant virus taxonomic family Geminiviridae are unique among viruses in possessing twinned or geminate virions. They are also unusual among plant viruses in that they possess single-stranded circular DNA genomes. The three genera of Geminiviridae are: the leafhopper-transmitted Mastreviruses (type member: maize streak virus, MSV); the leaf- and planthopper-transmitted Curtoviruses (type member: beet curly top virus, BCTV); and the whitefly-transmitted Begomoviruses (type member: bean golden mosaic virus, BGMV). Until recently, the three genera were known as Subgroups I, II and III, respectively. Mastreviruses and Curtoviruses have only a single genomic component of approximately 2.5 to 2.8 kb; Begomoviruses may have one or two components of the same size, one of which is dependent on the other for replication. Mastreviruses have the simplest organization, with Curtoviruses and Begomoviruses sharing a very similar and more complex organization. An overview of the genetic organization of geminivirus genomes is shown in FIG. 1.

The geminiviruses replicate via a rolling circle mechanism, analogous to that used by phage ΦX174 and ssDNA plasmids of gram positive microorganisms. The only exogenous a protein required for replication is the viral replication initiation (Rep) protein encoded by a geminiviral replicase gene. This multifunctional protein initiates replication at a conserved stem loop structure found in the viral origin of replication by inducing a nick within a conserved nonanucleotide motif (TAATATTA↓C) found in the intergenic loop sequence. Transcription of the viral genome is bidirectional with transcription initially within the intergenic (IR) region. Rep also has functions involved in controlling the plant cell cycle, and possibly also in modulating the expression of host genes involved in DNA replication (reviewed by Palmer et al., 1997b). The Rep protein can act in trans, that is, it need not be expressed by the viral replicon itself, but can be supplied from another extrachromosomal viral replicon, or even from a nuclear transgene (Hanley-Bowdoin et al., 1990). The cis requirements for viral replication are the viral intergenic region/s (IR), which contain sequences essential for initiation of rolling circle replication (the long intergenic region (LIR) of Mastreviruses, or the intergenic region of other geminiviruses) and synthesis of the complementary strand (the short IR (SIR) of Mastreviruses).

Infectious clones of geminiviruses are commonly constructed as tandem dimers or partial dimers of the virus genome, usually with the origin of replication sequences duplicated. This facilitates escape of the cloned virus from the cloning vector sequences by a replicative release mechanism mediated by the Rep protein inducing a nick at each stem-loop structure and the host DNA replication machinery then displacing a ssDNA copy of the viral genome. This mechanism applies to rescue of replication-defective geminivirus genomes from chromosomally integrated partial multimers by the Rep protein of wild type virus (see, for example, Stanley et al., 1990). Moreover, the Rep protein can mediate replicative release of recombinant viral DNA integrated into the host cell chromosome (Hayes et al., 1988; 1989; Kanevski et al., 1992; Palmer, 1997; Palmer et al., 1997d).

Geminiviruses replicate to very high copy number in the nuclei of infected cells, via a double-stranded DNA replicative intermediate form (RF-DNA) and have therefore attracted interest for their potential use in gene amplification strategies to increase the copy number and enhance the expression levels of foreign genes linked to the viral replicon (reviewed by Palmer et al., 1997a and Timmermans et al., 1994). Geminiviruses seem to be fairly plastic with respect to the size of foreign DNA that can be linked to the viral replicon without inhibiting DNA replication. There is, however, a stringent size limitation imposed on movement of virus genomes. This issue becomes irrelevant, however, if the geminiviral replicon is used in a transgene amplification system where a partial dimer of a "master copy" of the viral replicon (lacking the genes involved in viral movement) is integrated into every cell of a transgenic plant (Palmer et al., 1997a). The circular monomeric viral replicon is then mobilized from the master copy in the chromosome by a replicative release mechanism (Stenger et al., 1991), and the recombinant viral vector replicates to very high copy number as a nuclear episome (e.g. Hayes et al. ,1988; 1989; Kanevski etal., 1992; Palmer et al., 1997d). The RF-DNA forms of geminiviral genomes exist as histone-associated minichromosome structures, and their genes are transcribed by the host RNA polymerase complex. Transcription of genes linked to a geminiviral replicon should therefore be regulated by their respective promoter sequences.

U.S. Pat. Nos. 5,589,379 and 5,650,303, issued to Kridl et al., disclose use of a geminiviral gene transfer vector to permit inducible expression of a foreign gene in plants. In this approach, a first expression cassette has a foreign protein coding sequence under the control of the coat protein promoter native to the geminivirus. A second expression cassette has a geminiviral trans-acting transcription factor under the control of a plant-inducible promoter. In this way, transcription of the foreign gene reportedly can be regulated by the inducible expression of the trans-acting transcription factor.

A gene amplification approach to increasing the copy number and expression of recombinant transgenes could dramatically increase the level of desired foreign proteins in plants. This could lead to safer and more economical production of a protein of interest. In this regard, a transgene vector system that utilizes the release and replication capabilities of geminiviruses is particularly worthy of investigation.

Needham et al. disclose a binary vector containing the following elements derived from tobacco yellow dwarf virus: two copies of an LIR flanking an SIR and two complementary sense open reading frames (C1 and C2) which contain an intron, which when processed, produces a Rep protein under the transcriptional control of its native promoter within the LIR. This vector does not include open reading frames encoding the putative movement (V1) and coat (V2) proteins. Needham et al. disclose further that transgenic tobacco plants transformed with this vector further comprising a reporter gene, demonstrate release and episomal replication of the viral elements of the vector, and expression of the reporter gene (Needham et al., 1998, *Plant Cell Reports*, 17:631)

Atkinson et al. disclose an episomal vector containing the following elements derived from tobacco yellow dwarf virus: two copies of an LIR flanking both an SIR and two complementary sense open reading frames, C1 and C2 that produce Rep. The expression of the Rep protein is under the transcriptional control of its native promoter within the LIR. Atkinson et al. also disclose that transgenic *Petunia hybrida* plants containing a CaMv 35S promoter-driven chalcone synthase A gene cloned into the episomal vector, demonstrate release and episomal replication of the viral elements of the vector and the chalcone synthase A gene (Ross et al., 1998, *The Plant Journal*, 15:593).

There is a need in the art for a method of increasing the copy number of a recombinant transgene in a plant.

There is also a need in the art for a method of increasing the level of expression of a recombinant transgene in a plant.

There is also a need in the art for a method of increasing the level of protein expressed from a recombinant transgene in a plant.

SUMMARY OF THE INVENTION

The invention provides a pair of recombinant nucleic acid molecules wherein a first molecule comprises at least a portion of a long intergenic region (LIR) of a geminivirus genome and wherein the first molecule lacks a functional geminiviral coat protein encoding sequence, and a second molecule comprising a geminiviral replicase gene operably linked to a fruit ripening-dependent promoter.

As used herein, a "long intergenic region" (LIR) refers to a noncoding region that contains sequences capable of forming a hairpin structure, including a conserved 9-base sequence (TAATATTA↓C) found in all geminiviruses.

As used herein, "at least a portion of a long intergenic region" refers to a region of a long intergenic region (LIR) that contains a rep binding site capable of mediating excision and replication by a geminivirus Rep protein. The LIR of the geminivirus, bean yellow dwarf virus is 303 nucleotides (FIG. 2). As used herein, "at least a portion of a long intergenic repeat" refers to a fragment of the long intergenic repeat that is less than 303 nucleotides. "At least a portion" of a long intergenic region encompasses for example 50 nucleotides, 100 nucleotides, 150 nucleotides, 200 nucleotides, 250 nucleotides, 264 nucleotides, 270 nucleotides, 275 nucleotides, 280 nucleotides, 285 nucleotides, 290 nucleotides or 300 nucleotides. An LIR according to the invention includes an LIR of mastrevirus as well as an intergenic region (IR) of either curtovirms or begomovirus.

As used herein, "fruit ripening dependent" refers to inducible under fruit ripening conditions and/or expressed in a tissue specific manner.

By "tissue specific" is meant expressed only in tissues of the fruit or in leaves. Tissues of the fruit include vascular bundles, pericaip, collumella, epidermis, placental tissue, locular tissue and seeds. As used herein, "tissue specific" also refers to expressed in a seed specific manner.

As used herein, "seed specific" refers to expressed only in the developing seed encompassing the cotyledon and the embryo axis, but not including the root and the stem. As used herein, "seed specific" also refers to expressed in the endosperm and perisperm.

A "fruit ripening-dependent promoter" according to the invention does not include a native viral Rep protein promoter included in an LIR. The LIR sequence of Bean yellow dwarf 30 virus, including the putative TATA box (TTATA, boxed in FIG. 2) is presented in FIG. 2, for example. Sequences of other geminivirus LIRs are available in the literature. As used herein, the native rep gene promoter is located in the LIR and can regulate rep gene expression in a phloem specific manner. Therefore, the invention does not encompass control of the rep gene by a native rep promoter, which native promoter is found in an LIR (FIG. 2), and includes the TATA sequence TTATA (boxed in FIG. 2).

As used herein, a "fruit ripening-dependent promoter" can also be expressed in phloem wherein it demonstrates development-stage dependent expression encompassing expression during fruit ripening or embryo storage protein deposition.

As used herein, "development stage" refers to a particular period of cell growth, differentiation, and organization of cells which can be characterized by changes in anatomy, biochemistry, or the coordinate expression of a particular set of genes.

As used herein, "developing" refers to the process of growth, differentiation and organization of cells that occurs during the formation of a tissue (e.g. epidermis, phloem, xylem, parenchyma etc . . . ) or an organ (e.g. leaf, stem, root, flower, fruit or seed).

As used herein, "fruit" refers to the ovary of an angiosperm flower and the associated structures (e.g. the receptacle or parts of the floral tube) that enlarge and develop to form a mass of tissue surrounding the seeds. According to the invention, the particular tissues that are involved in fruit development vary with the species, but tissues involved in fruit development according to the invention, are always derived from the maternal parent of the progeny seeds.

As used herein, "ripe" refers to a stage of fruit development that is characterized by changes in pigmnentation, the conversion of acids and starches to free sugars, and breakdown of cell walls that results in softening of the fruit.

As used herein, "fruit ripening conditions" refer to conditions under which the developmental processes involved in fruit ripening can occur, including cell division and expansion of maternal tissues that occurs after fertilization of ovaries. As used herein, for example, production of ethylene is a chemical signal that stimulates the genetic program for ripening in climacteric fruits such as tomato.

As used herein, "embryo storage protein deposition" refers to the synthesis and accumulation of storage proteins in the parts of the embryo, particularly cotyledons, or seeds of species that lack endosperm and in which the embryo is large and contains most of the seed storage tissue (including for example, Leguminosae, Cucurbitaceae, Compositaea, Solanaceae, Brassicaceae).

"inducible" refers to expressed in the presence of an exogenous or endogenous chemical (for example an alcohol, a hormone, or a growth factor), in the presence of light and/or in response to developmental changes.

As used herein, "endogenous" refers to naturally occurring in a plant.

As used herein, "exogenous" refers to not naturally occurring in a plant.

As used herein, "inducible" also refers to expressed in any tissue in the presence of a chemical inducer". As used herein, "chemical induction" according to the invention refers to the physical application of a exogenous or endogenous substance (including macromolecules e.g. proteins, or nucleic acids) to a plant or a plant organ (e.g. by spraying a liquid solution comprising a chemical inducer on leaves, application of a liquid solution to roots or exposing plants or plant organs to gas or vapor) which has the effect of causing the target promoter present in the cells of the plant or plant organ to increase the rate of transcription.

As used herein, "protein of interest" refers to any protein that is either heterologous or endogenous to a geminivirus or plant.

As used herein, "gene of interest" refers to any gene that is either heterologous or endogenous to a geminivirus or plant.

As used herein, "nucleotide sequence of interest" refers to any nucleotide sequence that is either heterologous or endogenous to a geminivirus or plant. A nucleotide sequence of interest refers to DNA or RNA.

"Heterologous" refers to a gene which is not naturally present in a geminivirus genome or a gene which is not naturally present in a plant genome. "Heterologous" also refers to a protein which is not naturally expressed from a geminivirus genome or a plant genome.

"Endogenous" refers to a gene which is naturally present in a geminivirus genome or a plant genome. "Endogenous" also refers to a protein which is naturally expressed from a geminivirus genome or a plant genome.

As used herein, the term "operably linked" refers to the respective coding sequence being fused in-frame to a promoter, enhancer, termination sequence, and the like, so that the coding sequence is faithfully transcribed, spliced, and translated, and the other structural features are able to perform their respective functions.

In a preferred embodiment, the first molecule further comprises an SIR.

As used herein, "SIR" refers to a noncoding region of a Mastrevirus genome containing the putative complementary strand origin of replication, the binding site for a short DNA primer that primes synthesis of the complementary DNA strand and consensus polyadenylation signals in both strands. As used herein, "SIR" refers to a region of DNA that is approximately 150 base pairs and extends from the termination codon of the geminivirus coat proteins (V2) to the termination codon of one of the open reading frames encoding the Rep protein (C2).

According to the invention, a gene of interest can be located either 5' of an SIR or 3' of an SIR in a recombinant nucleic acid molecule.

In another preferred embodiment, the first molecule further comprises a plant-functional promoter.

In another preferred embodiment, the plant-fulnctional promoter is selected from the group consisting of CaMV 35S, tomato E8, patatin, ubiquitin, mannopine synthase (mas), rice actin 1, soybean seed protein glycinin (Gy1) and soybean vegetative storage protein (vsp).

In another preferred embodiment, the first molecule further comprises a gene of interest.

In another preferred embodiment, the gene of interest is a heterologous gene.

In another preferred embodiment, the gene of interest of the first molecule is selected from the group consisting of a gene encoding luciferase, glucuronosidase (GUS), green fluorescent protein (GFP), shigatoxin B (StxB), staphylococcus enterotoxin B (SEB), E. coli labile toxin B (LT-B), Norwalk virus capsid protein (NVCP), and hepatitis B surface antigen (HBsAg).

In another preferred embodiment, the first molecule further comprises a plant-functional termination sequence.

In another preferred embodiment, the plant-functional termination sequence is selected from the group consisting of nopaline synthase (nos), vegetative storage protein (vsp), pin2, and geminiviral short intergenic (sir) termination sequences.

In another preferred embodiment, the nucleotide sequence of the first DNA molecule is optimized for expression in plants by having at least one codon degenerate to a corresponding codon of the native protein encoding sequence.

In another preferred embodiment, the first molecule is single stranded.

The invention also provides a recombinant nucleic acid molecule comprising at least a portion of a long intergenic region (LIR) of a geminivirus genome and a geminiviral replicase gene operably linked to a fruit ripening-dependent promoter.

In a preferred embodiment, the recombinant nucleic acid molecule further comprises an SIR.

In another preferred embodiment, the recombinant nucleic acid molecule further comprises a plant-functional promoter.

In another preferred embodiment, the plant-functional promoter is selected from the group consisting of CaMV 35S, tomato E8, patatin, ubiquitin, mannopine synthase (mas), rice actin 1, soybean seed protein glycinin (Gy1) and soybean vegetative storage protein (vsp).

In another preferred embodiment, the recombinant nucleic acid molecule further comprises a gene of interest.

In another preferred embodiment, the gene is a heterologous gene.

In another preferred embodiment, the gene of interest is selected from the group consisting of a gene encoding luciferase, glucuronosidase (GUS), green fluorescent protein (GFP), shigatoxin B (StxB), staphylococcus enterotoxin B (SEB), E. coli labile toxin B (LT-B), Norwalk virus capsid protein (NVCP), and hepatitis B surface antigen (HbsAg).

In another preferred embodiment, the recombinant nucleic acid molecule further comprises a plant-functional termination sequence.

In another preferred embodiment, the plant-functional termination sequence is selected from the group consisting of nopaline synthase (nos), vegetative storage protein (vsp), pin2, and geminiviral short intergenic (sir) termination sequences.

In another preferred embodiment, the nucleotide sequence is optimized for expression in plants by having at least one codon degenerate to a corresponding codon of the native protein encoding sequence.

In another preferred embodiment, the recombinant nucleic acid molecule is single stranded.

The invention also provides an expression vector comprising a selectable marker gene and at least a portion of a long intergenic region (LIR) of a geminivirus genome, a restriction site for insertion of a gene of interest, a functional geminiviral replicase gene operably linked to a fruit ripening-dependent promoter, and wherein said nucleic acid sequence lacks a functional geminiviral coat protein encoding sequence.

In a preferred embodiment, the vector further comprises an SIR.

In another preferred embodiment, the vector lacks a functional geminiviral replicase gene.

In another preferred embodiment, the nucleotide sequence is flanked by two of said LIR portions.

In another preferred embodiment, the 5' end of the nucleotide sequence is operably linked to a plant-functional promoter sequence.

In another preferred embodiment, the vector further comprises a gene of interest.

In another preferred embodiment, the gene is a heterologous gene.

In another preferred embodiment, the gene of interest is selected from the group consisting of a gene encoding a luciferase, glucuronosidase (GUS), green fluorescent protein (GFP), shigatoxin B (StxB), staphylococcus enterotoxin B (SEB), labile toxin B (LT-B), Norwalk virus capsid protein (NVCP), and hepatitis B surface antigen (HbsAg).

In another preferred embodiment, the 3' end of the gene is operably linked to a plant-functional termination sequence.

In another preferred embodiment, the gene is optimized for expression in plants by having at least one codon degenerate to a corresponding codon of the native protein encoding sequence.

In another preferred embodiment, the vector further comprises an E. coli origin of replication.

In another preferred embodiment, the vector further comprises an Agrobacterium tumefaciens origin of replication.

In another preferred embodiment, the nucleotide sequence is flanked by left and right T-DNA border regions of Agrobacterium tumefaciens.

The invention also provides for a strain of E. coli transfected with an expression vector comprising a selectable marker gene and at least a portion of a long intergenic region (LIR) of a geminivirus genome, a restriction site for insertion of a gene of interest, a functional geminiviral replicase gene operably linked to a fruit ripening-dependent promoter, and wherein said nucleic acid sequence lacks a functional geminiviral coat protein encoding sequence, and further comprising an E. coli origin of replication.

The invention also provides for a strain of Agrobacterium tumefaciens transfected with an expression vector comprising a selectable marker gene and at least a portion of a long intergenic region (LIR) of a geminiviras genome, a restriction site for insertion of a gene of interest, a functional geminiviral replicase gene operably linked to a fruit ripening-dependent promoter, and wherein said nucleic acid sequence lacks a functional geminiviral coat protein encoding sequence, and firther comprising an *E. coli* origin of replication, further comprising an *Agrobacterium tumefaciens* origin of replication.

In a preferred embodiment, the strain further comprises a helper tumor-inducing (Ti) plasmid.

The invention also provides for a transgenic plant cell transformed with a nucleic acid having at least a portion of a long intergenic region (LIR) of a gemninivirus genome, a gene of interest, wherein the nucleic acid lacks a functional geminiviral coat protein encoding sequence.

The invention also provides for a transgenic plant cell transformed with a nucleic acid comprising at least a portion of a long intergenic region (LIR) of a geminivirus genome flanking a restriction site for insertion of a gene of interest, and a functional geminiviral replicase gene operably linked to a fruit ripening-dependent promoter and wherein the nucleic acid sequence lacks a functional geminiviral coat protein encoding sequence.

In a preferred embodiment, the transgenic plant cell further comprises a heterologous gene.

In another preferred embodiment, the transgenic plant cell lacks a functional geminiviral replicase gene.

In another preferred embodiment, the nucleic acid is present in nuclear episomes in the cell.

In another preferred embodiment, the 5' end of the gene of interest is operably linked to a plant-functional promoter sequence.

In another preferred embodiment, the gene of interest is selected from the group consisting of a gene encoding luciferase, glucuronosidase (GUS), green fluorescent protein (GFP), shigatoxin B (StxB), staphylococcus enterotoxin B (SEB), labile toxin B (LT-B), Norwalk virus capsid protein (NVCP), and hepatitis B surface antigen (HBsAg).

In another preferred embodiment, the 3' end of the gene of interest is operably linked to a plant-functional termination sequence.

In another preferred embodiment, the gene of interest is optimized for expression in plants by having at least one codon degenerate to a corresponding codon of the native protein encoding sequence.

In another preferred embodiment, the transgenic plant cell further comprises a viral replicase encoding sequence operably linked to a plant functional promoter and a termination sequence.

In another preferred embodiment, transcription of the viral replicase encoding sequence is regulated by an inducible promoter.

In another preferred embodiment, the 5' end of the viral replicase encoding sequence is operably linked to a tissue-specific promoter.

In another preferred embodiment, the tissue-specific promoter is selected from the group consisting of glucocorticoid, estrogen, jasmonic acid, insecticide RH5992, copper, tetracycline, and alcohol-inducible promoters.

In another preferred embodiment, the viral replicase encoding sequence encodes a wild-type geminiviral replicase.

In another preferred embodiment, the viral replicase encoding sequence is provided as an expression cassette or viral replicon.

The invention also provides for a transgenic plant seed transformed with a nucleic acid having at least a portion of a long intergenic region (LIR) of a geminivirus genome, a gene of interest, wherein the nucleic acid lacks a functional geminiviral coat protein encoding sequence.

The invention also provides for a transgenic plant seed transformed with a nucleic acid comprising at least a portion of a long intergenic region (LIR) of a geminivirus genome, a restriction site for insertion of a gene of interest, and a functional geminiviral replicase gene operably linked to a fruit ripening-dependent promoter and wherein the nucleic acid sequence lacks a functional geminiviral coat protein encoding sequence.

In a preferred embodiment, the seed further comprises a heterologous gene.

In another preferred embodiment, the nucleic acid lacks a functional geminiviral replicase gene.

In another preferred embodiment, the seed further comprises a viral replicase encoding sequence expressed in trans with the nucleotide sequence.

In another preferred embodiment, the 5' end of the viral replicase encoding sequence is operably linked to a fruit ripening-dependent promoter.

In another preferred embodiment, the seed is selected from tobacco, tomato, potato, banana, soybean, pepper, wheat, rye, rice, spinach, carrot, maize and corn.

The invention also provides for a method of transforming a plant cell comprising contacting the plant cell with a strain of *Agrobacterium tumefaciens* transfected with an expression vector comprising a selectable marker gene and a nucleic acid sequence comprising at least a portion of a long intergenic region (LIR) of a geminivirus genome, a restriction site for insertion of a gene of interest, and a functional geminiviral replicase gene operably linked to a fruit ripening-dependent promoter and wherein said nucleic acid sequence lacks a functional geminiviral coat protein encoding sequence, and further comprising an *Agrobacterium tumefaciens* origin of replication, under conditions effective to transfer and integrate the nucleotide sequence into the nuclear genome of the cell.

In a preferred embodiment, the transformed plant cell is regenerated.

The invention also provides a method of transforming a plant cell comprising subjecting the plant cell to microparticle bombardment with solid particles loaded with a pair of recombinant nucleic acid molecules wherein a first molecule comprises at least a portion of a long intergenic region (LIR) of a geminivirus genome, and wherein the first molecule lacks a functional geminiviral coat protein encoding sequence, and a second molecule comprising a geminiviral replicase gene operably linked to a fruit ripening-dependent promoter, under conditions effective to transfer and integrate said nucleotide sequence into the nuclear genome of the cell.

The invention also provides a method of producing a transgenic plant comprising transforming a plant cell by a method comprising subjecting the plant cell to microparticle bombardment with solid particles loaded with a pair of recombinant nucleic acid molecules wherein a first molecule comprises at least a portion of a long intergenic region (LIR) of a geminivirus genome, and wherein the first molecule lacks a functional geminiviral coat protein encoding sequence, and a second molecule comprising a geminiviral replicase gene operably linked to a fruit ripening-dependent promoter under conditions effective to transfer and integrate said nucleotide sequence into the nuclear genome of the cell, and regenerating the plant cell.

The invention also provides a method of amplifying a heterologous nucleotide sequence in a transgenic plant comprising producing a transgenic plant by a method comprising transforming a plant cell by a method comprising subjecting the plant cell to microparticle bombardment with solid particles loaded with a pair of recombinant nucleic acid molecules wherein a first molecule comprises at least a portion of a long intergenic region (LIR) of a geminivirus genome, and wherein the first molecule lacks a functional geminiviral coat protein encoding sequence, and a second molecule comprising a geminiviral replicase gene operably linked to a fruit ripening-dependent promoter under conditions effective to transfer and integrate said nucleotide sequence into the nuclear genome of the cell, and regenerating the plant cell, and subjecting the transgenic plant to a wild-type geminivirus, which expresses a viral replicase in planta that rescues and replicates the nucleotide sequence in cells of the plant.

The invention also provides a method of overproducing a protein in a plant comprising producing a transgenic plant by the method of contacting the plant cell with a strain of *Agrobacterium tumefaciens* transfected with an expression vector comprising a selectable marker gene and a nucleic acid sequence comprising at least a portion of a long intergenic region (LIR) of a geminivirus genome, a restriction site for insertion of a gene of interest, and a functional geminiviral replicase gene operably linked to a fruit ripening-dependent promoter and wherein said nucleic acid sequence lacks a functional geminiviral coat protein encoding sequence, and further comprising an *Agrobacterium tumefaciens* origin of replication, under conditions effective to transfer and integrate the nucleotide sequence into the nuclear genome of the cell, ans subjecting the transgenic plant to a wild-type geminivirus, which expresses a viral replicase in planta that rescues and replicates the nucleotide sequence in said plant.

The invention also provides for a method of amplifying a heterologous nucleotide sequence in a transgenic plant comprising producing a transgenic plant by the method of contacting the plant cell with a strain of *Agrobacterium tumefaciens* transfected with an expression vector comprising a selectable marker gene and a nucleic acid sequence comprising at least a portion of a long intergenic region (LIR) of a geninivirus genome, a restriction site for insertion of a gene of interest, and a functional geminiviral replicase gene operably linked to a fruit ripening-dependent promoter and wherein said nucleic acid sequence lacks a functional geminiviral coat protein encoding sequence, and further comprising an *Agrobacterium tumefaciens* origin of replication, under conditions effective to transfer and integrate the nucleotide sequence into the nuclear genome of the cell, and subjecting the transgenic plant to a chemical or developmental agent, which induces expression of a viral replicase in planta that rescues and replicates the nucleotide sequence in the plant.

In a preferred embodiment, the inducible promoter is selected from the group consisting of glucocorticoid, estrogen, and alcohol-inducible promoters.

In another preferred embodiment, replication of the viral replicase is expressed in trans with the nucleotide sequence.

The invention also provides for a method of overproducing a protein in a plant, comprising producing a transgenic plant produced by the method comprising contacting the plant cell with a strain of *Agrobacterium tumefaciens* transfected with an expression vector comprising a selectable marker gene and a nucleic acid sequence comprising at least a portion of a long intergenic region (LIR) of a geminivirus genome, a restriction site for insertion of a gene of interest, and a functional geminiviral replicase gene operably linked to a fruit ripening-dependent promoter and wherein said nucleic acid sequence lacks a functional geminiviral coat protein encoding sequence, and further comprising an *Agrobacterium tumefaciens* origin of replication, under conditions effective to transfer and integrate the nucleotide sequence into the nuclear genome of the cell, and subjecting the transgenic plant to a chemical or developmental agent, which induces expression of a viral replicase in planta that rescues and replicates the nucleotide sequence in the plant.

The invention also provides a recombinant nucleic acid molecule comprising a functional geminiviral replicase gene operably linked to a fruit ripening-dependent promoter.

The invention also provides a vector comprising a functional geminiviral replicase gene operably linked to a fruit ripening-dependent promoter.

The invention also provides a transgenic plant cell transformed with a nucleic acid comprising a functional geminiviral replicase gene operably linked to a fruit ripening-dependent promoter.

In a preferred embodiment, the transgenic plant cell is selected from the group consisting of tobacco, tomato, potato, banana, soybean, pepper, wheat, rye, rice, spinach, carrot, maize and corn.

The invention also provides a transgenic plant seed transformed with a nucleic acid comprising a functional geminiviral replicase gene operably linked to a fruit ripening-dependent promoter.

In a preferred embodiment, the transgenic plant cell is selected from the group consisting of tobacco, tomato, potato, banana, soybean, pepper, wheat, rye, rice, spinach, carrot, maize and corn.

The present invention thereby affords a method of amplifying, i.e., increasing the copy number, of a desired nucleotide sequence, in the genome of a transgenic plant, thereby permitting expression of the encoded protein over basal levels obtained in the absence of amplification. Moreover, protein expression can be regulated in a fruit ripening-dependent manner.

BRIEF DESCRIPTION OF THE DRAWINGS

FIG. 2 shows the nucleic acid sequence of the LIR of Bean Yellow Dwarf Virus (SEQ ID NO:1). Translation start sites for the Rep/RepA protein (C1) and by arrows. Putative TATA boxes are boxed. Stem and loop are indicated by underlined and outlined text respectively. Putative introns appear in bold faced letters.

FIG. 10 is the nucleic acid sequence of a rep gene including the intron (SEQ ID NO:2). The sequences of the C1 protein (SEQ ID NO:3) and C2 protein (SEQ ID NO:4) are indicated.

FIG. 18 is the nucleic acid sequence of a rep gene without the intron (SEQ ID NO:5). The sequence of the corresponding protein (SEQ ID NO:6) is indicated.

FIG. 36 is the nucleotide sequence of a plant-optimized mutant staphylococcal enterotoxin B (SEB-F44S) gene (SEQ ID NO:7). The sequence of the corresponding protein (SEQ ID NO:8) is indicated.

DETAILED DESCRIPTION OF THE INVENTION

The invention is based on the discovery that DNA constructs comprising components of the viral genome can be excised and episomally replicated in the presence of a geminiviral replicase gene encoding a Rep protein. These constructs can be used to amplify a gene of interest and to express a protein of interest in a plant. Further, these constructs can be used to amplify a gene of interest and express a protein of interest in a regulated manner in plants in the presence of geminiviral replicase gene that is transcriptionally regulated by a fruit ripening-dependent promoter.

As used herein, "episomally replicated" refers to independent replication of an episome. An "episome" according to the invention refers to a mobile genetic element or plasmid that can exist either in an autonomous extrachromosomal state or can be integrated into a chromosome".

I. Geminiviruses

Geminiviruses useful according to the invention include Begomoviruses, Curtoviruses and Mastreviruses.

Figure 1:
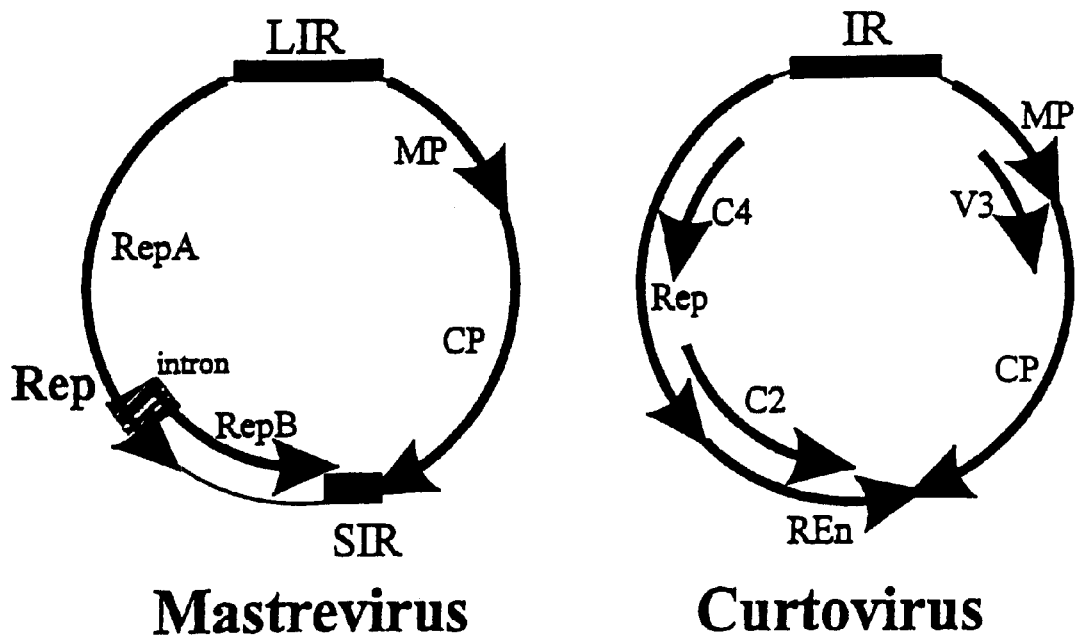
FIG. 1 illustrates the genome organization of the geminiviruses.

FIG. 1 shows the consensus genome organization of double stranded replicative forms of geminiviruses. Grey boxes indicate the intergenic regions (IR) which contain the origin of replication and transcription regulatory regions for bidirectional transcription. The part of the intergenic region which is identical in both Begomovirus genome components is called the common region (CR); as Mastreviruses have two intergenic regions, the region which contains the origin of replication and viral gene promoter sequences is called the long intergenic region (LIR). The putative complementary strand origin of replication in Mastreviruses is in the short intergenic region (SIR), where a short DNA primer binds, and possibly primes synthesis of the complementary DNA strand. Open reading frames are shown by arrows, which indicate the direction in which the ORF is transcribed. Where a gene's function is known, the name of the gene product is indicated. CP: coat protein; MP: movement protein; Rep: replication initiator protein; TrAP: transcriptional activator protein for virion-sense genes; REn: replication enhancer protein. In Curtoviruses, the C2 ORF does not seem to have transcriptional activator activity. An AV1 ORF is indicated as the coat protein gene in all cases, whether or not an AV1 ORF is present. The position of an intron which results in fusion of the Mastrevirus RepA and RepB open reading frames in processed mRNAs is indicated.

A. Mastreviruses

Mastreviruses have the simplest genetic organization of any members of the plant virus taxonomic family Geminiviridae.

Species in the Subgroup I (Mastrevirus) genus of the geminiviruses that are useful according to the invention include bean yellow dwarf virus (BeYDV)(Liu et al., 1997, J. Gen. Virol., 78:2113), Bromus striate mosaic virus (BrSMV), Chioris striate mosaic virus (CSMV)(GenBank M20021), Digitaria streak virus (DSV)(GenBank M23022), Digitaria striate mosaic virus (DiSMV), maize streak virus (MSV) (GenBank AF003952), Miscanthus streak virus, strain natal (MiSV) (DBBJ D00800), Panicum streak virus (PanSV-Kar) (GenBank L39638), Paspalum striate mosaic virus (PSMV), sugarcane streak virus (SSVN) (GenBankM82918), tobacco yellow dwarf virus (TYDV) (GenBank M81103), and wheat dwarf virus (WDV) (EMBL X82104). Tentative species in the genus include bajra streak virus (BaSV) and chickpea chlorotic dwarf virus (CpCDV).

Exemplary of a Mastrevirus vector for use in the present invention is bean yellow dwarf virus (BeYDV). BeYDV has only one genome component (Liu et al. 1997). It has only three genes, which encode the replication initiator protein (rep), the movement protein, and the coat protein (FIG. 1). All of the viral genes are essential for viral infectivity, but only the rep gene is required for replication (see Palmer & Rybicki, 1997b for a review of Subgroup I geminivirus molecular biology). BeYDV is preferred for several reasons: as a Mastrevirus, BeYDV has a fairly simple genomic organization; it also has a broad host range which encompasses both legumes and solanaceous plants. BeYDV can be used as a system for enhancing tissue specific gene expression in tomatoes or for seed specific expression in soybeans.

Tobacco yellow dwarf virus (TYDV)(GenBank M81103) is also exemplary of a Mastrevirus genome useful according to the invention.

B. Curtovirus

Species in the Subgroup II (Curtovirus) genus of the geminiviruses that are useful according to the invention include but are not limited to beet curly top virus (BCTV) (GenBank M24597), horseradish curly top virus (HRCTV) (GenBank U49907) and tomato pseudo curly top virus (TPCTV) (EMBL X84735).

C. Begomovirus

Species in the Subgroup III (Begomovirus) genus of the geminiviruses that are useful according to the invention include but are not limited to mungbean yellow mosaic virus (MYMV) (DDBJ D14703), tomato yellow leaf curl virus strain Israel (TYLCV-Is) (EMBL X1 5656), African cassava mosaic virus strain West Kenya (ACMV-K) (EMBL Z24758), Indian cassava mosaic virus (ICMV) (EMBL Z24758), Indian tomato leaf curl virus (ItmLCV)(GenBank Z48182), Ageratum yellow vein virus (AgYVV)(EMBL X74516), pepper huasteco virus (PHV)(EMBLX70418), Texas pepper virus strain Tamaulipas (TPV)(GenBank U57457), tomato golden mosaic virus (TGMV)(GenBank K02029), bean golden mosaic virus (BGMV)(GenBank M88686), potato yellow mosaic virus (PYMV)(DDBJ D00940), bean dwarf mosaic virus (BDMV) (GenBank M88179), tomato mottle virus (TmoV)(GenBank L14460) and Abutilon mosaic virus (AbMV)(EMBL X15983).

Figure 3A:
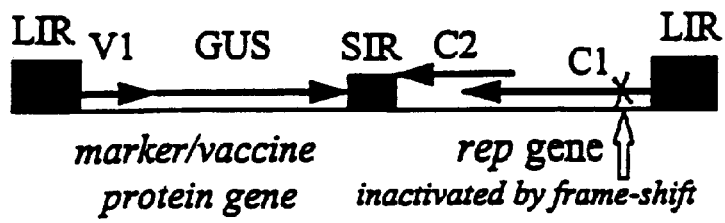
FIG. 3A shows a replicon construct, whereby a partial dimer can be integrated into the chromosome of a transgenic plant. Due to a mutation in the Rep protein, it is unable to replicate until Rep protein is supplied.
Figure 3B:
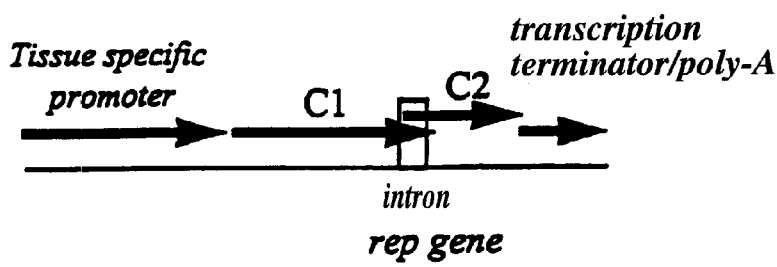
FIG. 3B shows a Rep expression cassette in which the rep gene (C1/C2) is placed under the control of a fruit ripening-dependent promoter (e.g., tomato E8 promoter or soybean seed protein promoter).
Figure 3C:
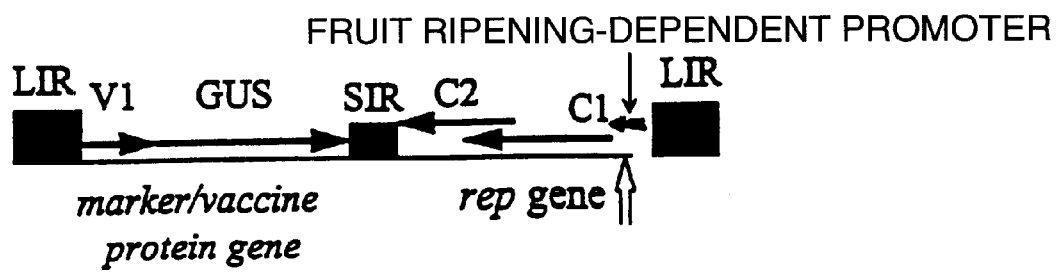
FIG. 3C shows a replicon construct whereby a partial dimer can be integrated into the chromosome of a transgene plant comprising a gene of interest and a rep gene under the control of a fruit ripening-dependent promoter.

In the present invention, a geminiviral Rep protein can mediate replication of viral DNA in trans with the appropriate cis-acting sequences providing the viral origin of replication. In one aspect, the dual expression cassettes for a gene of interest, represented by the GUS reporter gene and a rep gene under the transcriptional control of a fruit ripening-dependent promoter, are shown illustrated in FIGS. 3A and 3B. The expression cassette for a gene of interest either lacks a rep gene or contains an inactivated rep gene. Alternatively, these cassettes can be provided together in a single vector, wherein the Rep protein is under the transcriptional control of a fruit ripening-dependent promoter as illustrated in FIG. 3C. Following transformation, the cassettes can be present in the plant cell either integrated into the nuclear genome or extrachromosomal, e.g., as episomes.

Figure 4:
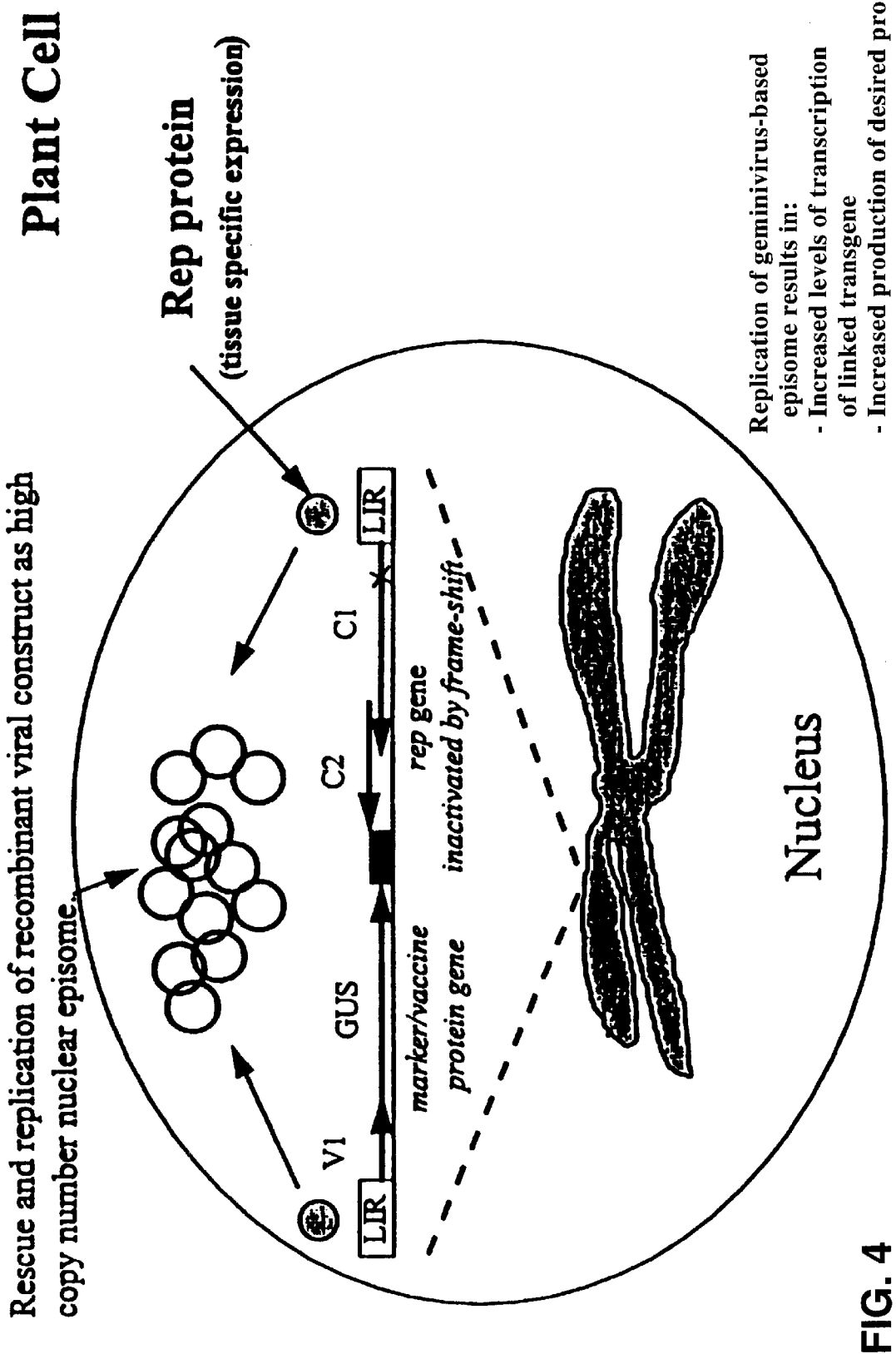
FIG. 4 illustrates the Rep-mediated rescue and replication of a chromosome-integrated viral replicon as a high copy number nuclear episome.

Rescue and replication of a viral cassette wherein the rep gene is inactivated integrated into a plant genome is illustrated in FIG. 4. The trans-acting Rep protein also present within the cell, by virtue of endogenous production or separate transformation, is shown acting at the cleaved LIR borders of the viral construct so as to release the construct from the chromosome.

II. Constructs Useful According to the Invention

The invention provides for DNA constructs comprising components of the viral genome, wherein a nucleotide sequence encoding a protein of interest can be introduced into the DNA construct, and wherein the viral elements of the construct and the nucleotide sequence encoding a protein of interest can be rescued and episomally replicated in the presence of a replicase gene under the transcriptional control of a fruit ripening-dependent promoter.

The invention provides for constructs comprising at least a portion of a geminiviral LIR. A portion of the LIR that is usefull according to the invention will include enough of the LIR to present the nick recognition sequence of a replicase protein, which permits rescue and replication of the DNA construct from a nuclear genome. A construct useful according to the invention lacks a functional geminiviral coat protein encoding sequence so that capsid formation and encapsidation of the viral DNA does not occur. A construct that lacks a functional geminiviral coat protein encoding sequence can be provided by deleting a portion of the coat protein encoding sequence and replacing the deleted section with the nucleotide sequence of interest encoding a protein of interest. The construct can also be provided as a full or partial dimer, which affords a second LIR recognition sequence and facilitates rescue of the desired sequence.

Constructs comprising at least a portion of a geminiviral LIR can be randomly integrated into a chromosome and can be excised by a Rep protein in a site specific manner.

A preferred geminivirus genome for use as a template, i.e., for performing mutations and modifications, is that of the mastrevirus bean yellow dwarf virus (BeYDV). For instance, the rep gene of this virus can be rendered non-functional, e.g., minimnally by inducing a frame shift, in a DNA construct of the present invention. As used herein, "non-flinctionar" means that the protein encoded and expressed by the affected nucleotide sequence is unable to perform its customary and usual function, in this case rescue and replication of a recognized sequence. As used herein, "functional" means capable of performing its customary and usual function. Inactivation of the native rep gene or removal of the native rep gene is desired in order to permit inducible expression of a separately provided viral replicase gene.

The invention provides for a pair of DNA constructs wherein a first DNA construct comprises at least a portion of an LIR of a geminivirus genome, including a site for insertion of a nucleotide sequence encoding a protein of interest, and lacks both a functional geminiviral coat protein encoding sequence and a functional rep gene. The rep gene can either be deleted (as shown in FIG. 3C) or inactivated (as shown in FIG. 3A). The second DNA construct comprises a functional geminiviral replicase gene encoding a Rep protein, operably linked to a fruit ripening-dependent promoter.

Figure 5B:
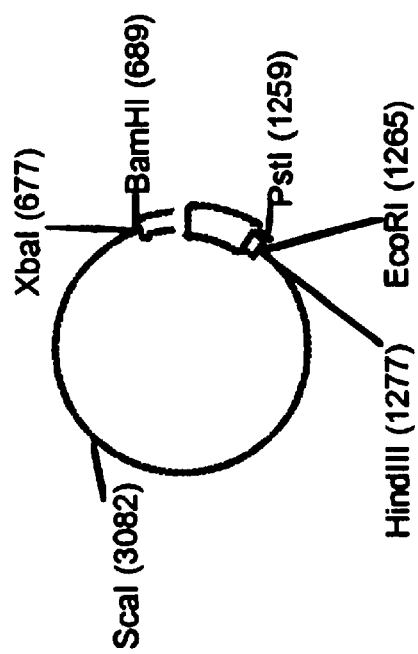
FIG. 5 illustrates plasmid maps of pBY002, pBY017, pBY019, pBY020, pBY024, pBY027 and pBY028.
Figure 5A:
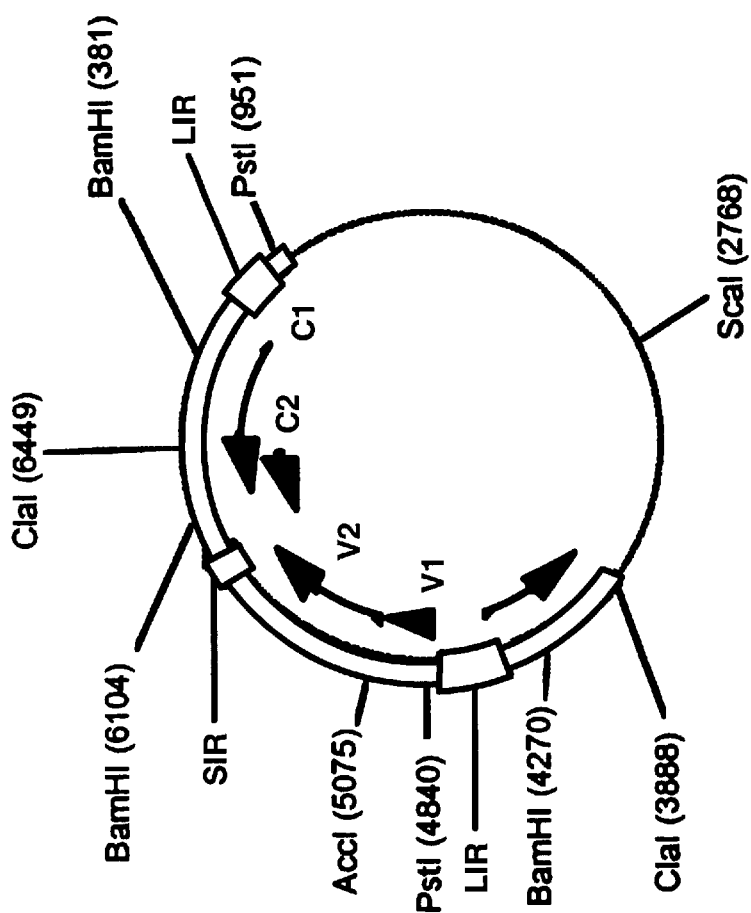

Vectors comprising at least a portion of a geminiviral LIR, including a site for insertion of a nucleotide sequence encoding a protein of interest, and lacking both a functional geminiviral coat protein encoding sequence and a functional rep gene useful according to the invention include pBY024 (FIG. 5).

A DNA construct comprising a gene of interest flanked by two LIRs useful according to the invention is pBY217 (FIG. 6), a derivative of pBY024 wherein the expression cassette for hepatitis B surface antigen is flanked by BeYDV LIR elements.

Figure 7:
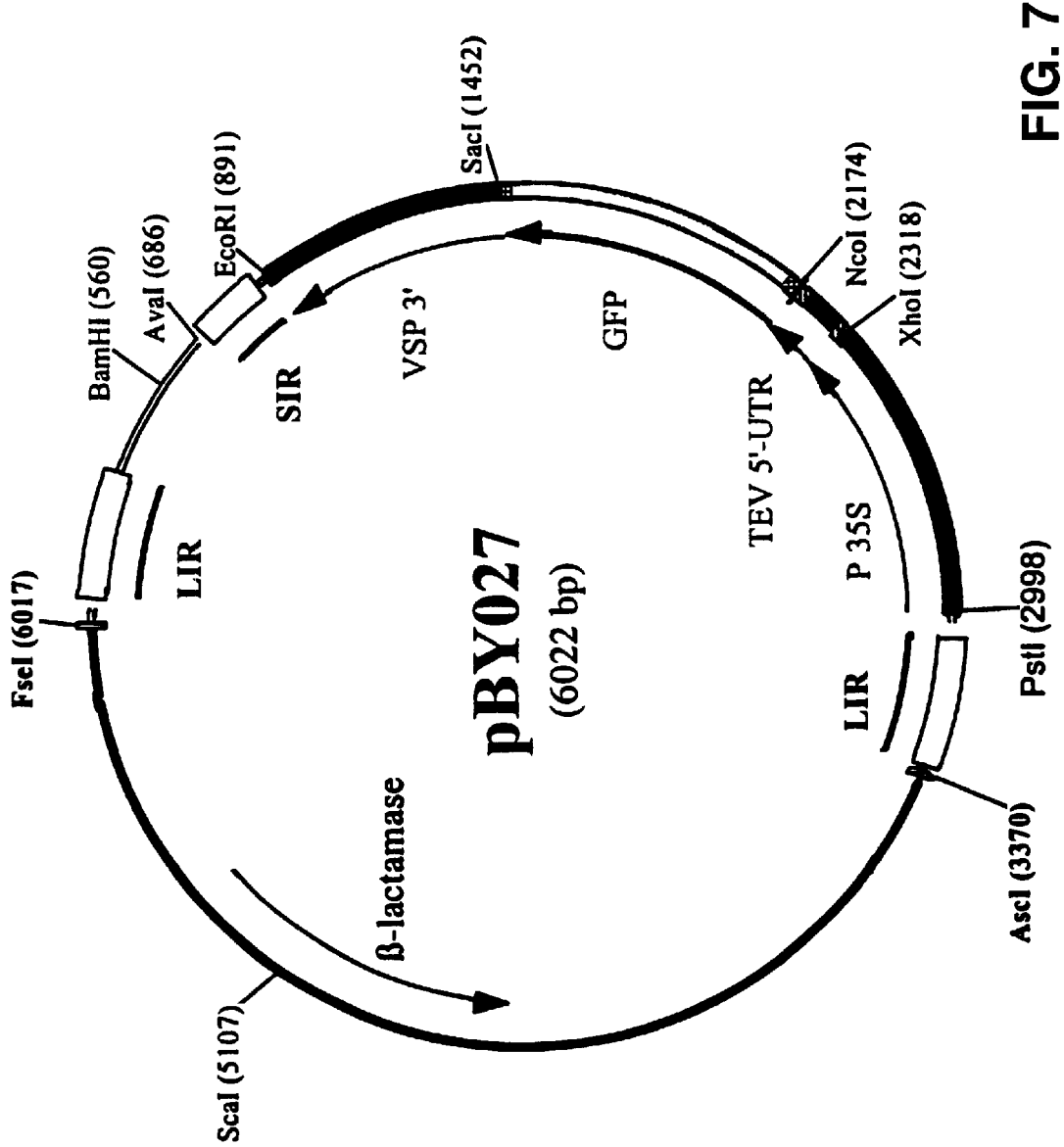
FIG. 7 is a plasmid map of pBY027.
Figure 8:
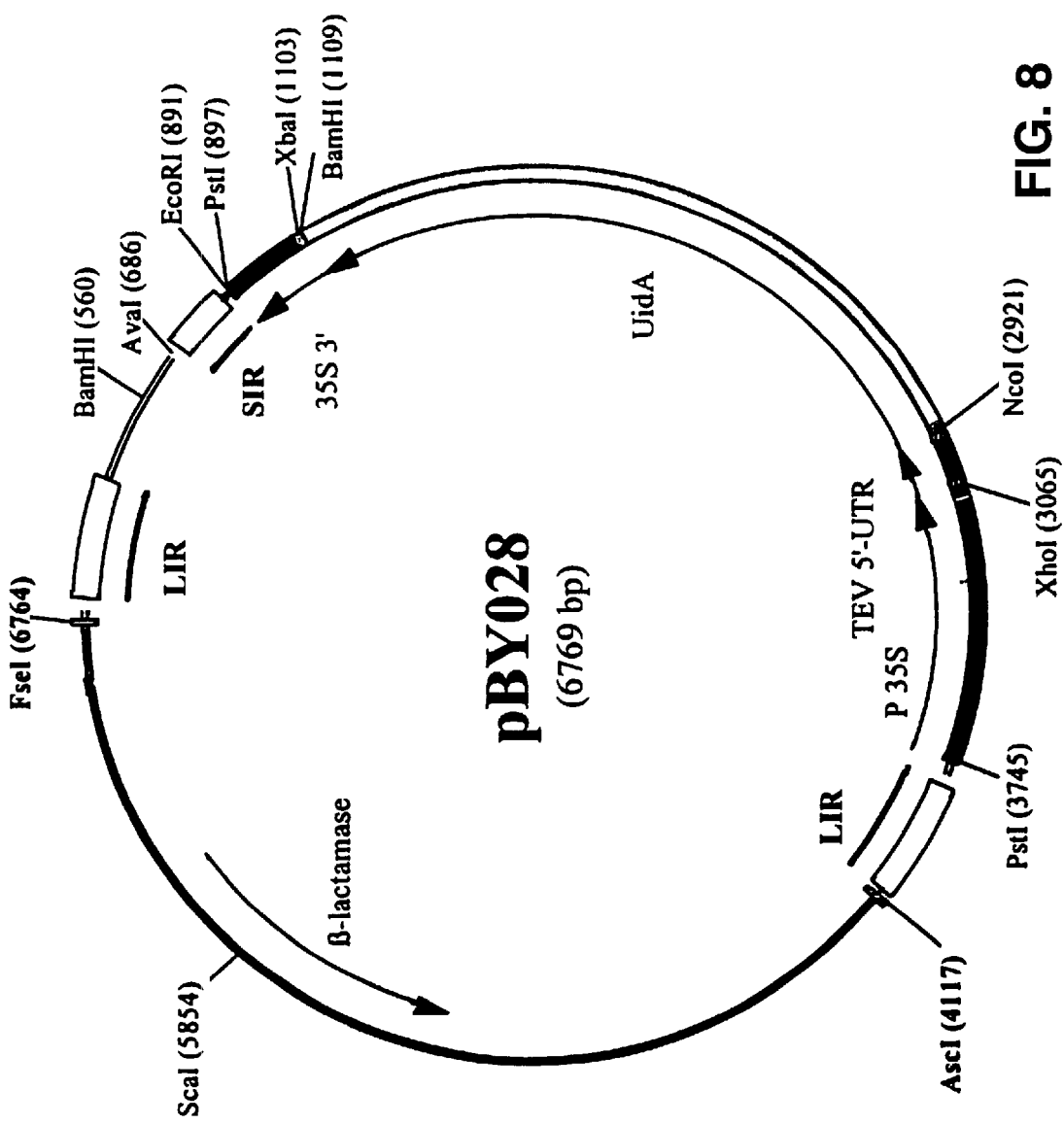
FIG. 8 is a plasmid map of pBY028.
Figure 9:
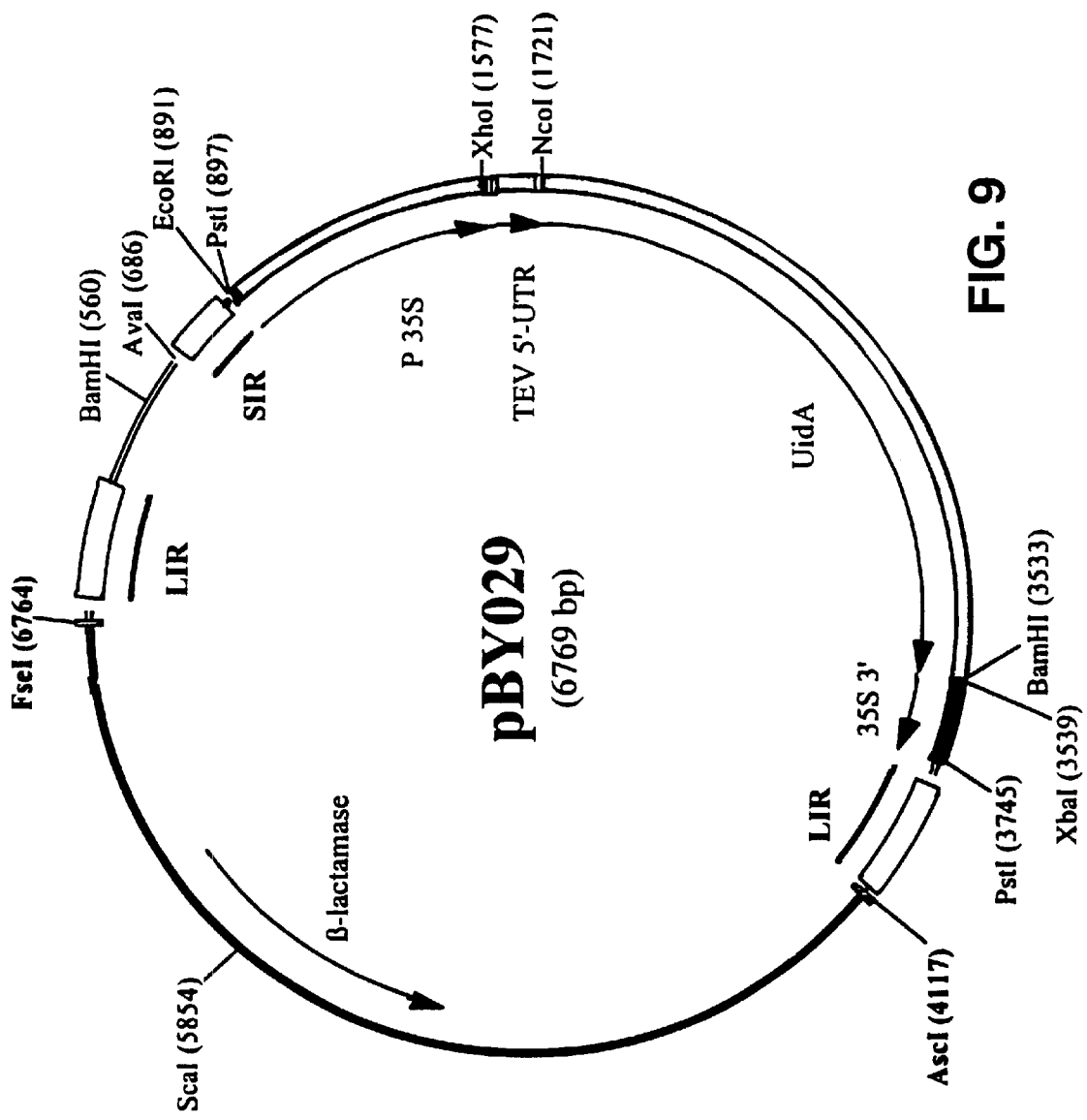
FIG. 9 is a plasmid map of pBY029.

Another DNA construct comprising a gene of interest flanked by two LIRs useful according to the invention is pBY027 (FIG. 7), a derivative of pBY024 wherein the expression cassette for GFP is flanked by BeYDV LIR elements. Other DNA constructs comprising a gene of interest flanked by two LIRs useful according to the invention are pBY028 (FIG. 8), and pBY029 (FIG. 9) a derivative of pBY024 wherein the expression cassette for GUS (UidA) is flanked by BeYDV LIR elements. pBY028 and pBY029 comprise the expression cassette for GUS (UidA) cloned in a orientation such that the 5' end of the GUS gene is adjacent to the LIR and such that the 3' end of the GUS gene is adjacent to the LIR, respectively.

The invention also provides for a DNA construct comprising at least a portion of a geminiviral LIR, a restriction site for insertion of a gene of interest, and a functional geminiviral replicase gene operably linked to a fruit ripening-dependent promoter.

A vector comprising a DNA construct comprising at least a portion of a geminiviral LIR, a restriction site for insertion of a gene of interest, and a functional geminiviral replicase gene operably linked to a fruit ripening-dependent promoter is prepared by cloning a Rep protein encoding sequence under the control of a fruit ripening-dependent promoter into pBY024 by methods well known in the art (Ausubel et al., 1995, Short Protocols in Molecular Biology, 3rd Edition, John Wiley & Sons, Maniatis et al., 1982, Molecular Cloning: A Laboratory Manual. Cold Spring Harbor Laboratory).

Figure 11:
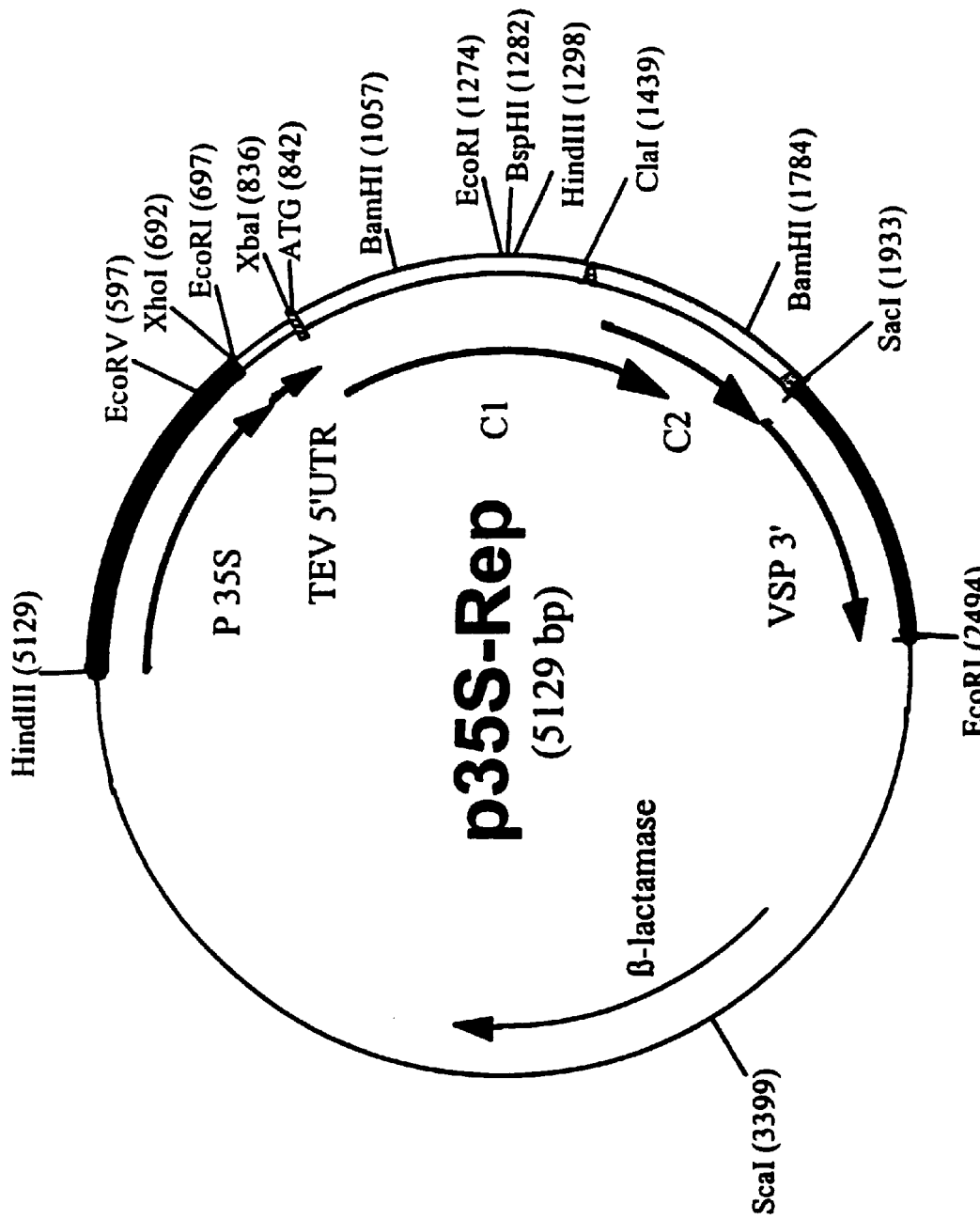
FIG. 11 is a plasmid map of p35S-Rep.
Figure 12:
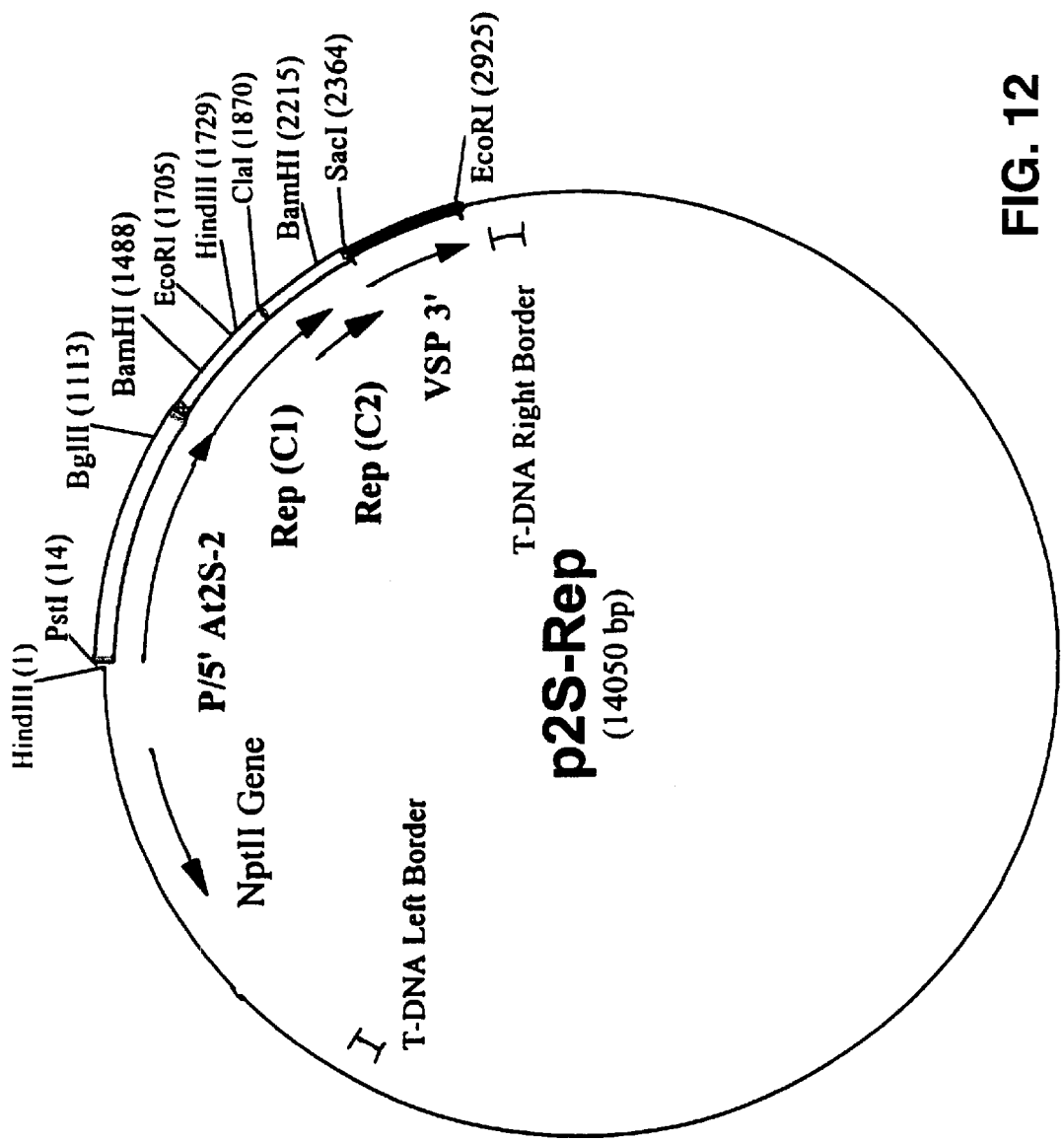
FIG. 12 is a plasmid map of p2S-Rep.
Figure 13:
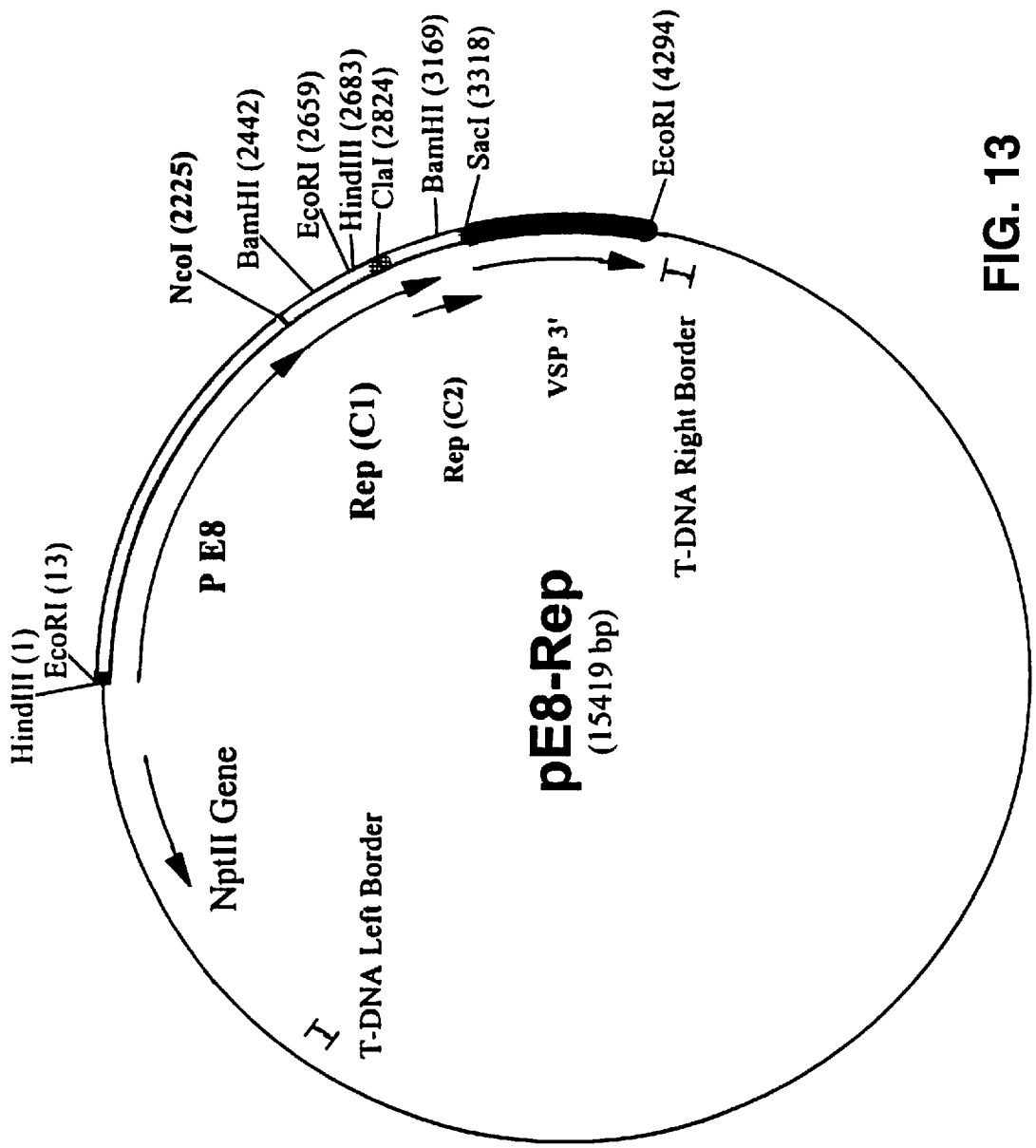
FIG. 13 is a plasmid map of pE8-Rep.
Figure 14:
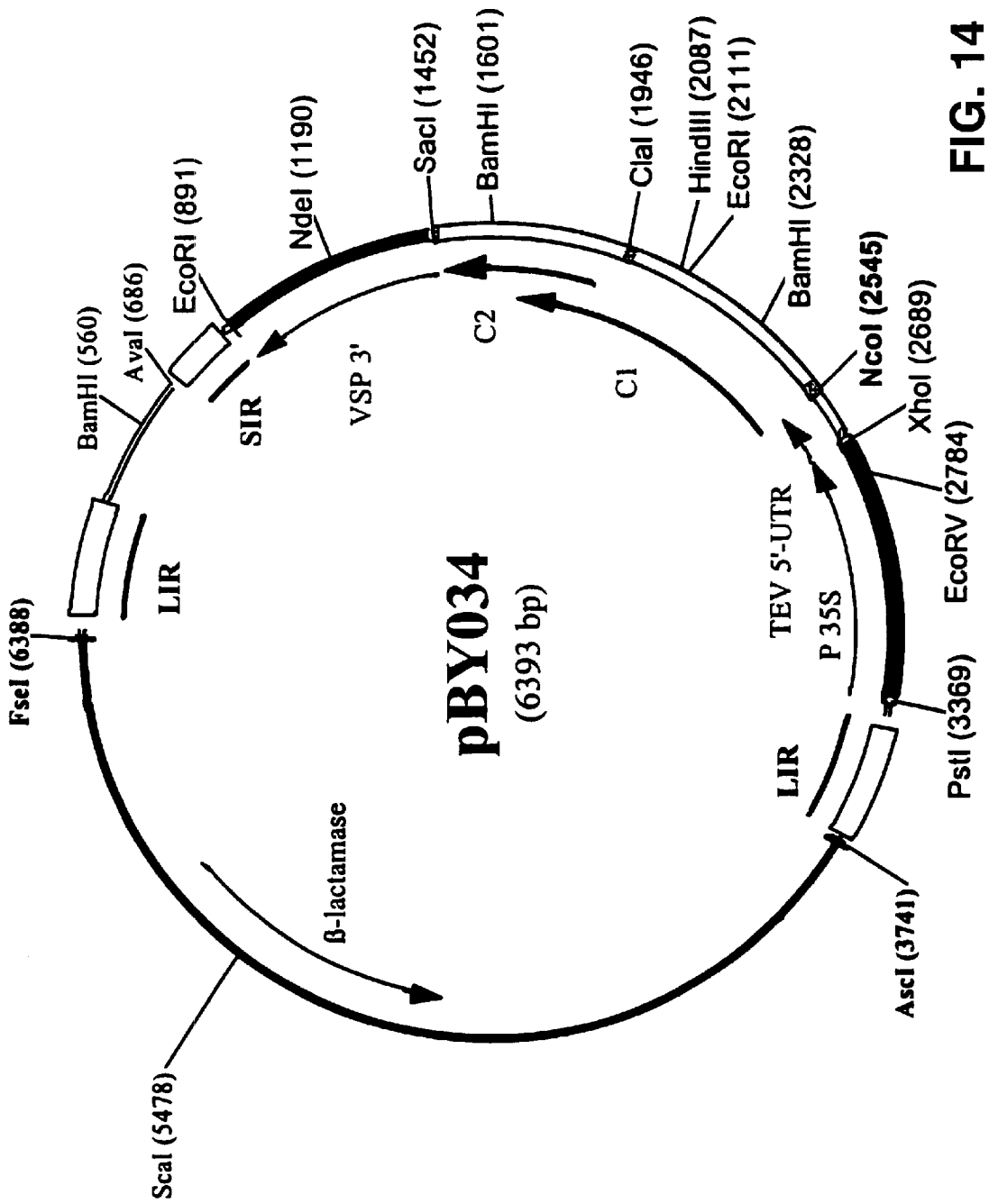
FIG. 14 is a plasmid map of pBY034.
Figure 15:
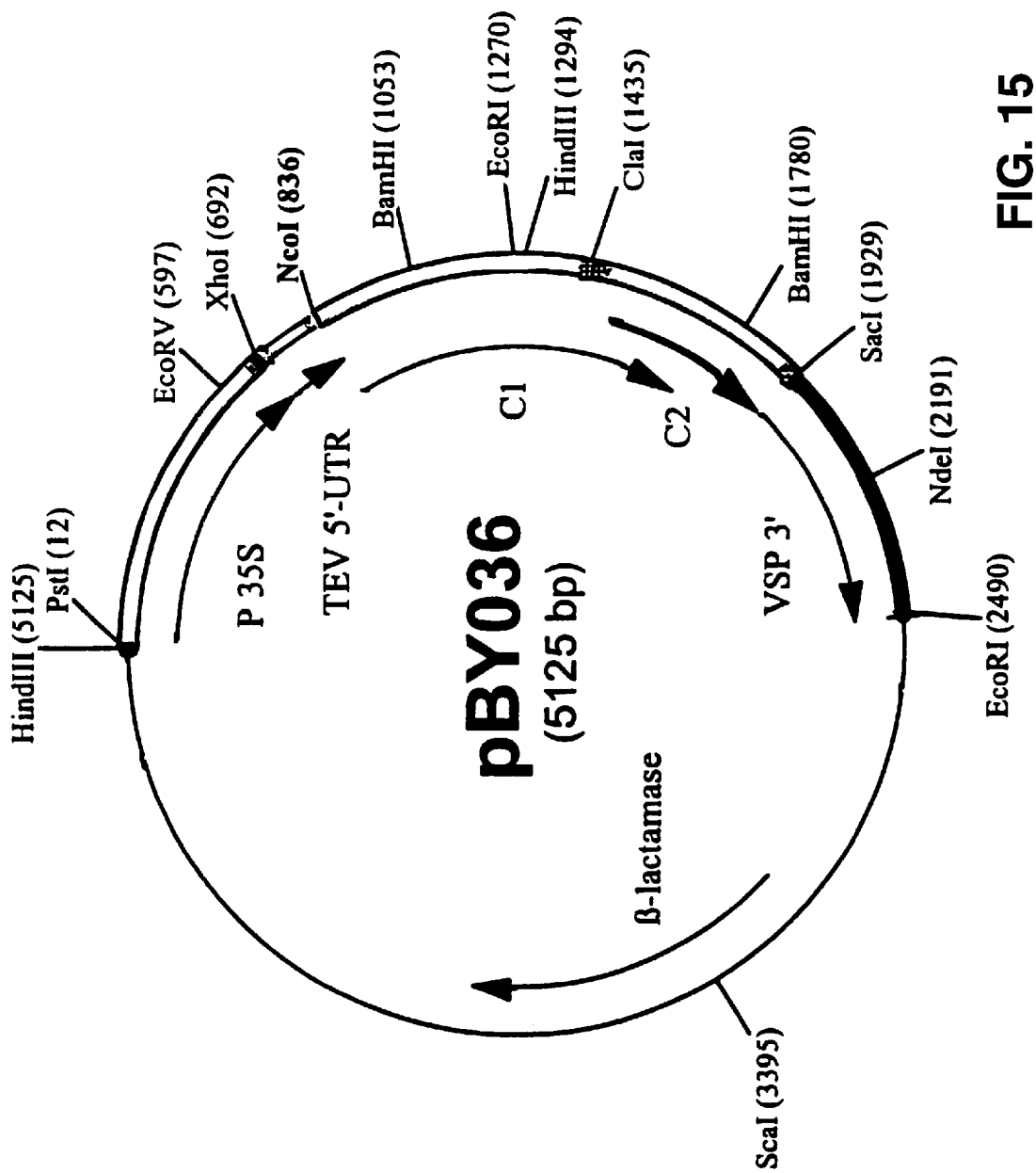
FIG. 15 is a plasmid map of pBY036.
Figure 16:
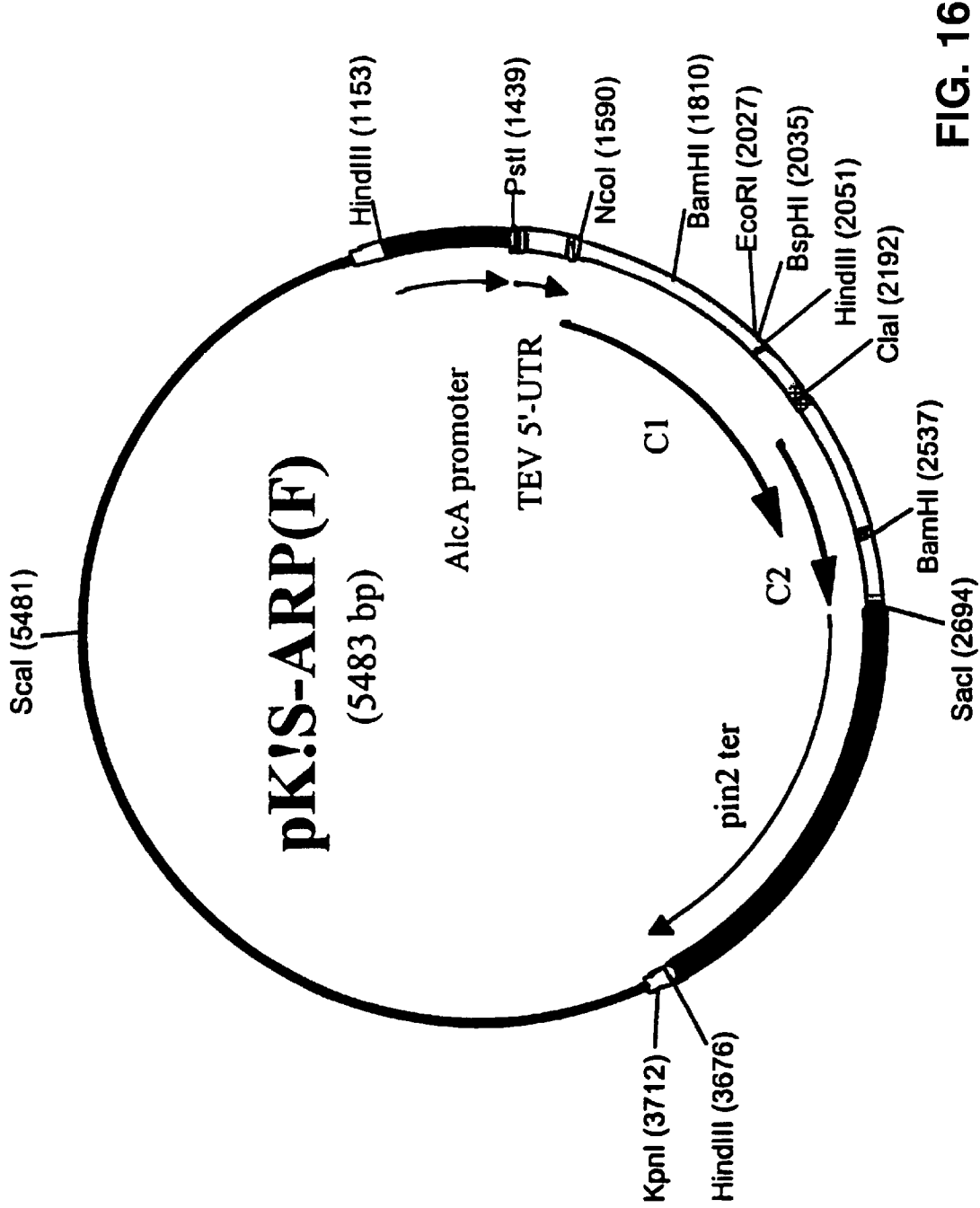
FIG. 16 is a plasmid map of pK!S-ARP(F).
Figure 17:
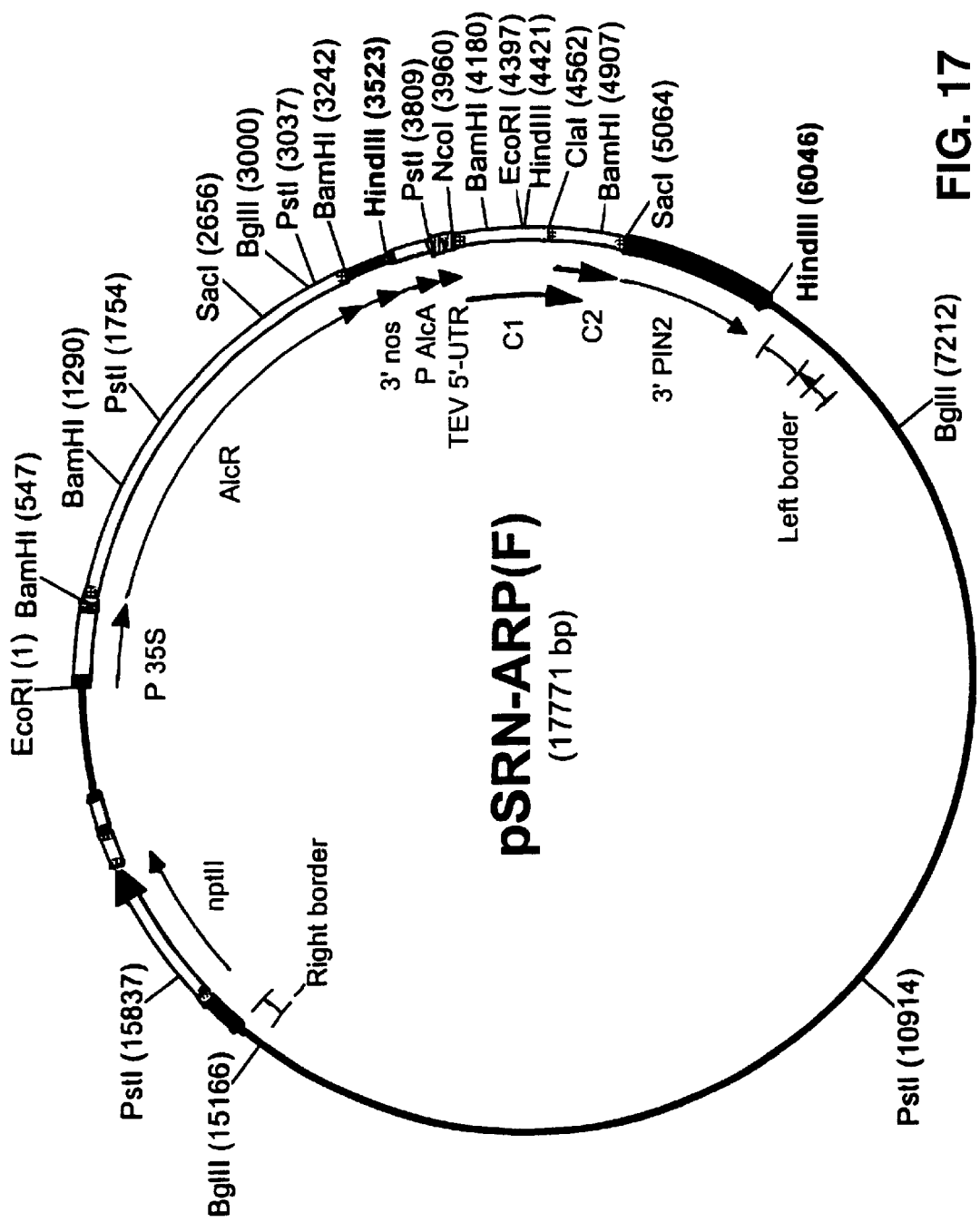
FIG. 17 is a plasmid map of SRN-ARP(F).
Figure 19:
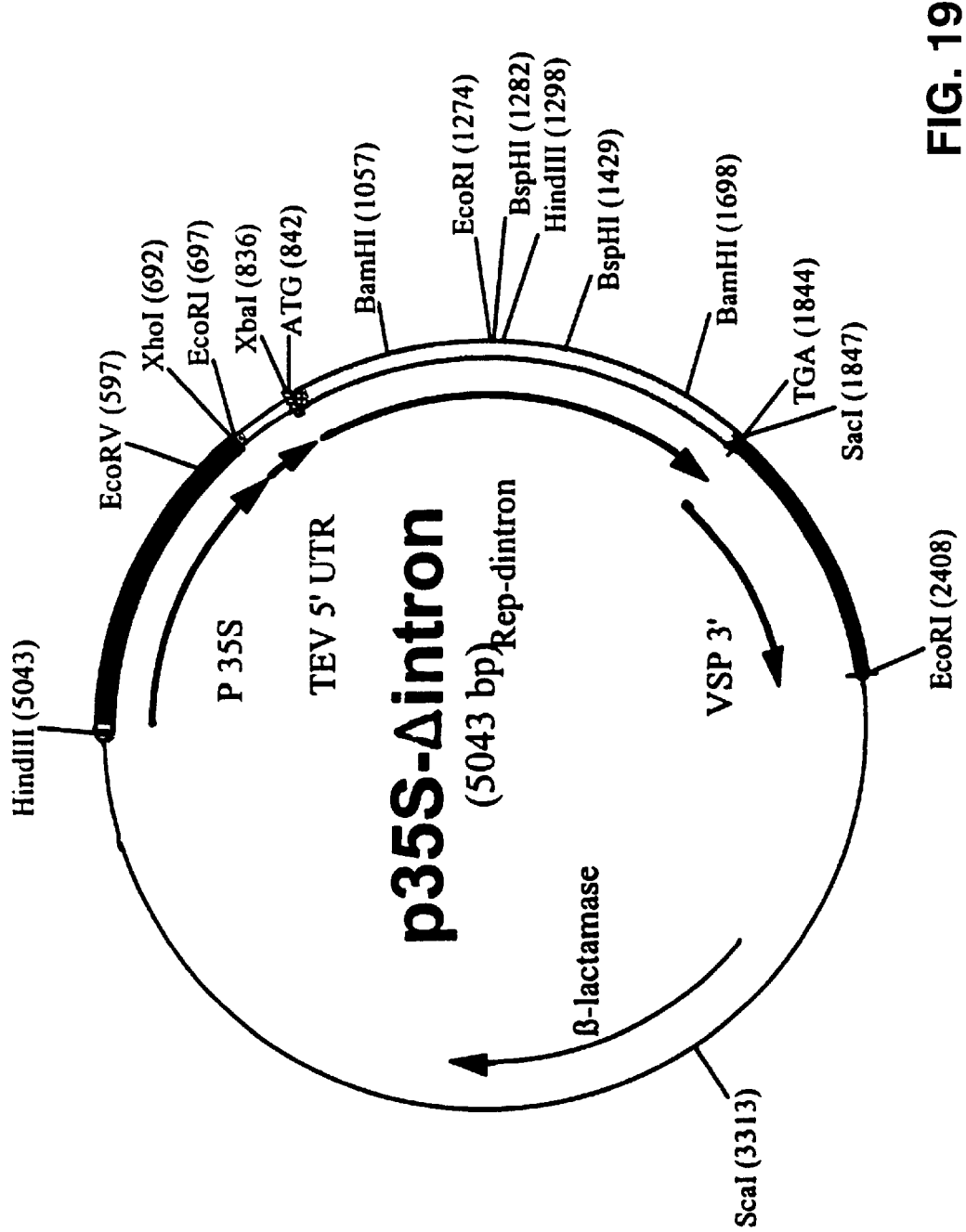
FIG. 19 is a plasmid map of p35S-Δintron.
Figure 20:
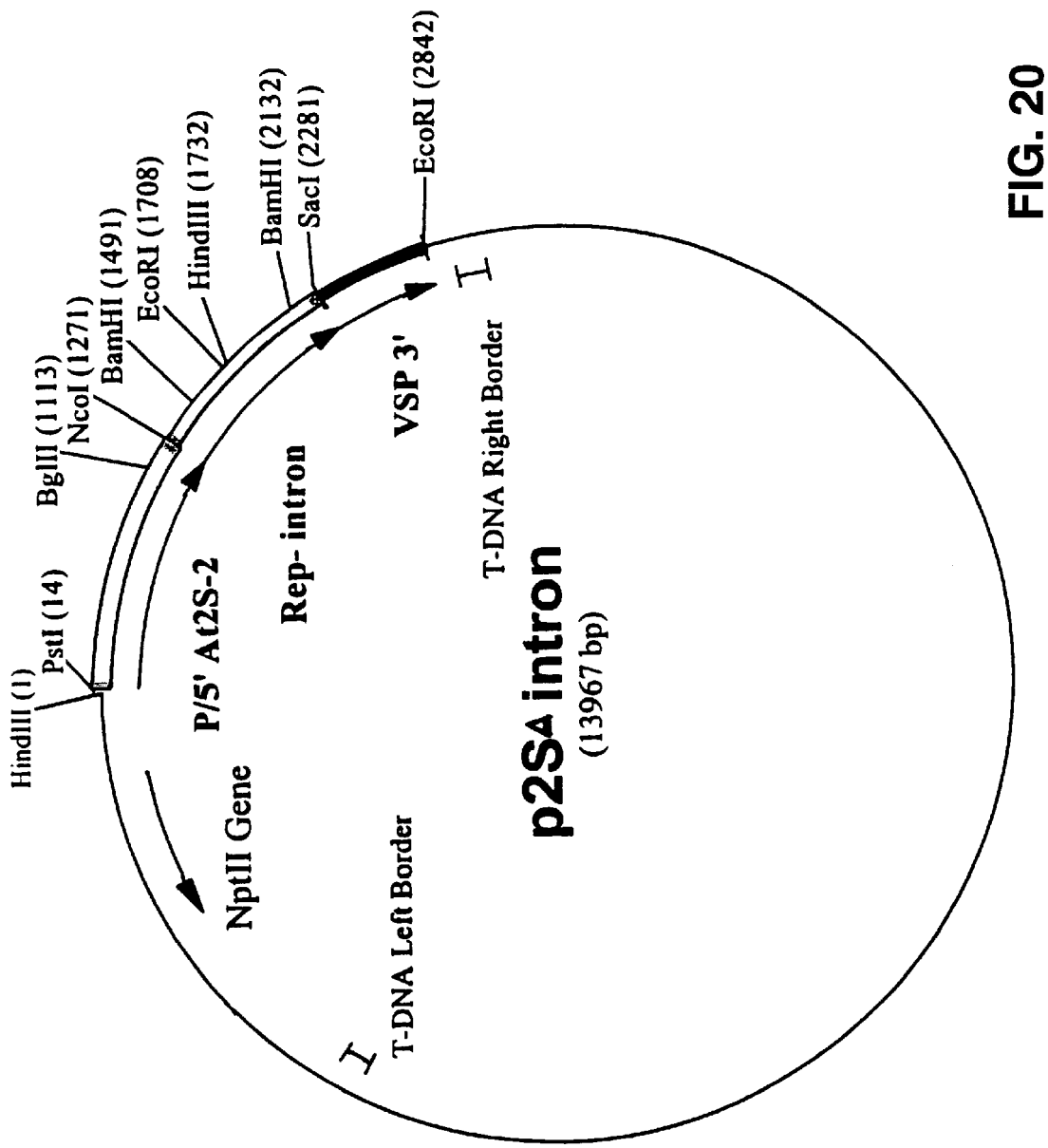
FIG. 20 is a plasmid map of p2SΔintron
Figure 21:
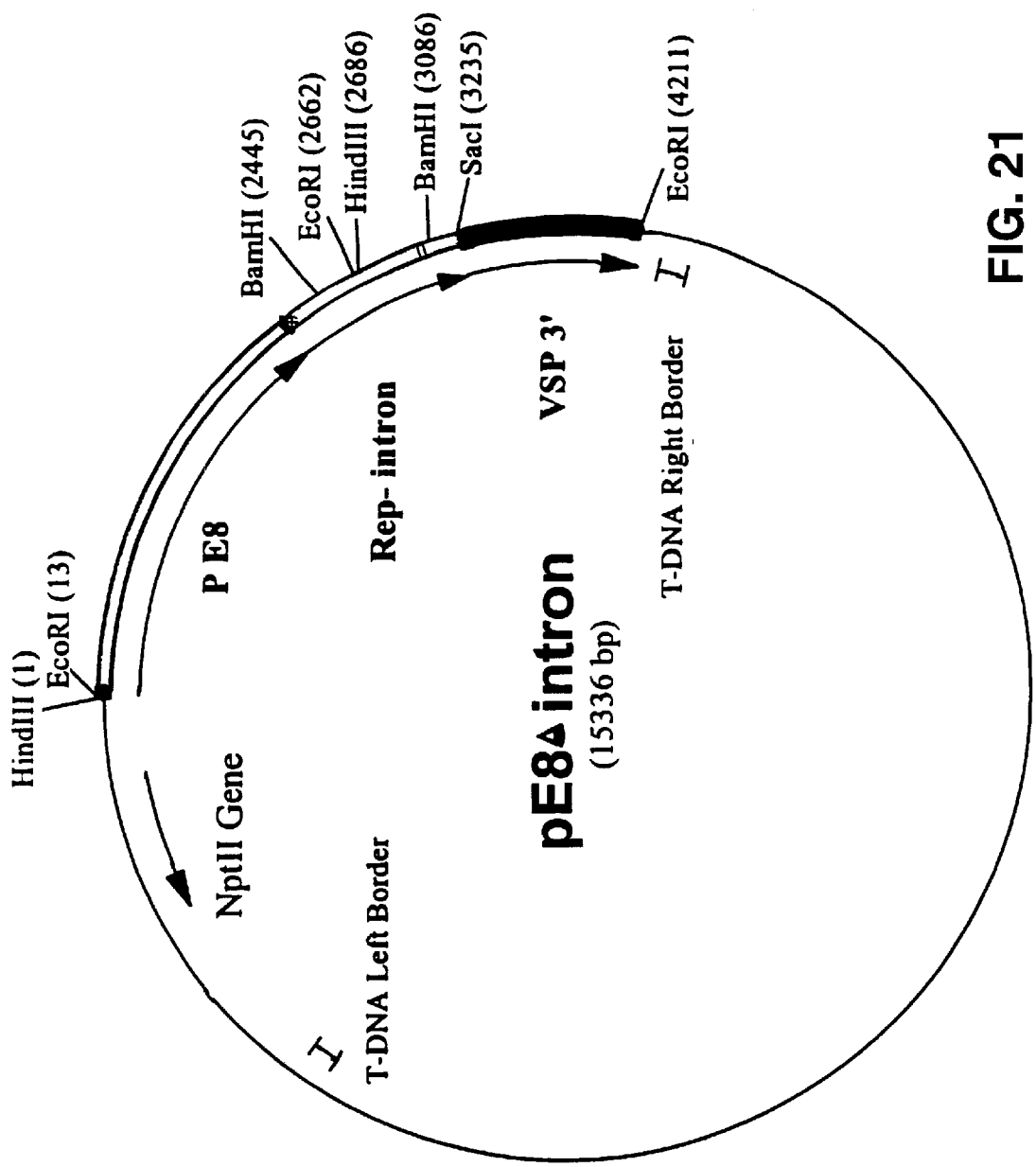
FIG. 21 is a plasmid map of pE8Δintron.
Figure 22:
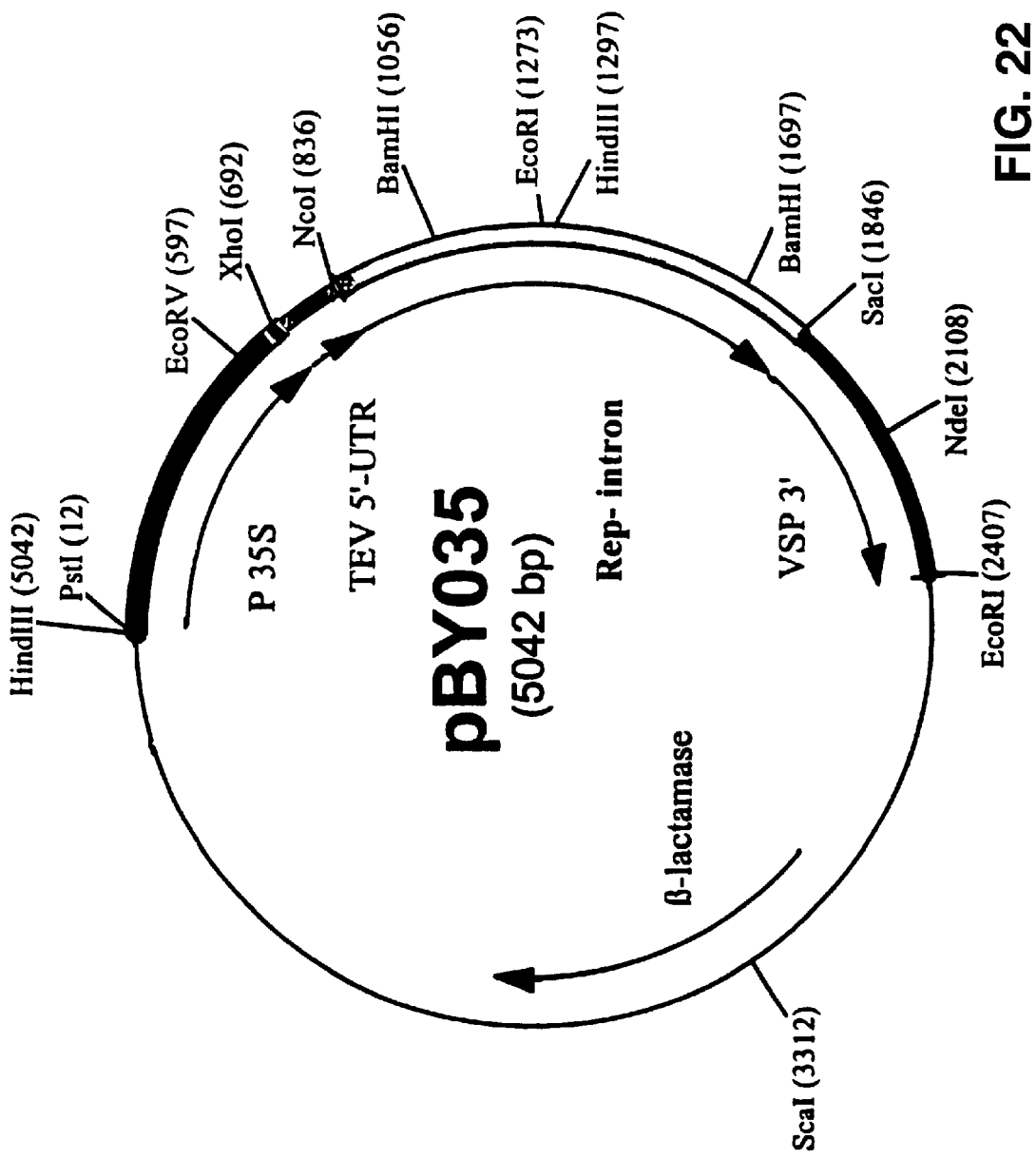
FIG. 22 is a plasmid map of pBY035.
Figure 23:
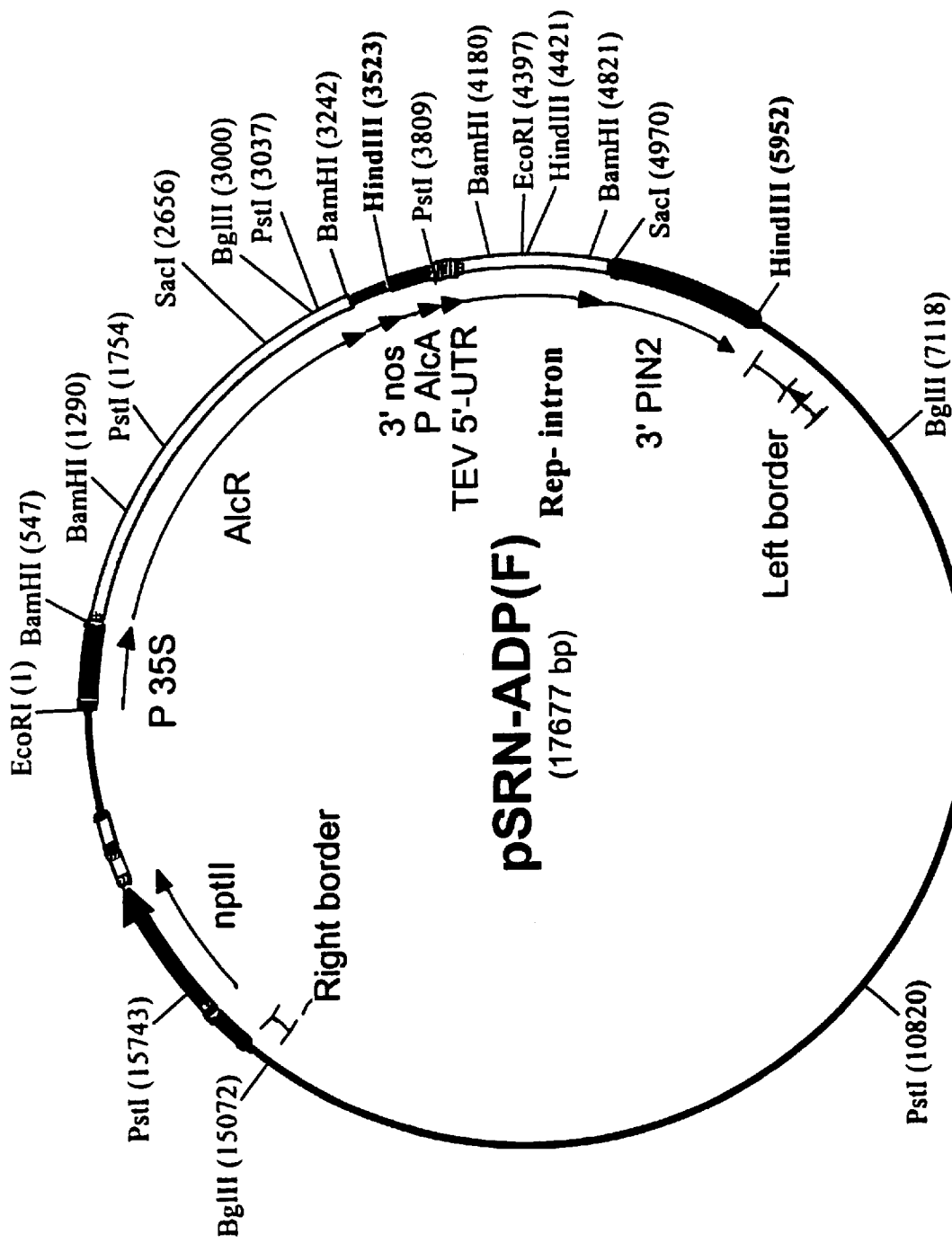
FIG. 23 is a plasmid map of pSRN-ADP(F).

Since replication of a nucleotide sequence of interest is ultimately desired it is necessary to provide a viral replicase, preferably as needed. This can be achieved by supplying a wild-type geminivirus, or more preferably, by using genetic engineering techniques to provide a geminiviral rep gene as an expression cassette or a viral replicon, which rep gene is under the control of a fruit ripening-dependent promoter. rep genes useful according to the invention are derived from any geminivirus included in the section entitled "Geminiviruses". RepA refers to the 250 amino acid translation product of the C1 open reading frame (ORF). Rep refers to the 360 amino acid translation product of the spliced C1 and C2 ORFs. Upon transcription and translation, the expressed protein replicase can act in trans to effect rescue and replication of the desired heterologous nucleotide sequence. A preferred rep gene sequence useful according to the invention is presented in FIG. 10. Useful Rep constructs include but are not limited to pBY002 (FIG. 5), p35S-REP (FIG. 11) p2S-REP (FIG. 12), pE8-REP (FIG. 13), pBY034 (FIG. 14) and pBY036 (FIG. 15). Useful Rep constructs wherein the rep gene is under the control of the alchohol inducible AlcR promoter include pK!S-ARP(F) (FIG. 16) and pSRN-ARP(F) (FIG. 17). Removal of the inton within the Mastrevirus rep gene greatly enhances BeYDV replication. A preferred intronless rep gene sequence useful according to the invention is presented in FIG. 18. DNA constructs comprising an intronless form of Mastrevirus Rep (Δintron) are also useful according to the invention. Intronless Rep constructs useful according to the invention include but are not limited to p35SΔintron (FIG. 19), p2SΔintron (FIG. 20), pE8Δintron (FIG. 21) and pBY035 (FIG. 22). A useful intronless Rep construct comprising an intronless rep gene under the control of the AlcA promoter is pSRN-ADP(F) (FIG. 23). Alternatively, the invention provides for a providing a geminiviral rep protein under the control of a fruit ripening-dependent promoter in cis.

A DNA construct according to the invention preferably has a plant-functional promoter operably linked to the 5' end of a nucleotide sequence of interest. A preferred promoter is selected from among CaMV 35S, tomato E8, patatin, ubiquitin, mannopine synthase (mas), rice actin 1, soybean seed protein glycinin (Gy1), soybean vegetative storage protein (vsp), and granule-bound starch synthase (gbss). A construct of the present invention can also include a translational enhancer region, such as tobacco etch virus (TEV) enhancer, which has been described elsewhere (Carrington, et al. (1990)). Optionally, a construct of the invention can comprise at least one vegetative storage protein (VSP) signal peptide encoding sequence, such as an αS or αL sequence (Mason et al. 1988), operably linked to the 5' end of a nucleotide sequence encoding a protein of interest.

As used herein, the term "operably linked" refers to the respective coding sequence being fused in-frame to a promoter, enhancer, termination sequence, and the like, so that the coding sequence is faithfully transcribed, spliced, and translated, and the other structural features are able to perform their respective functions.

A DNA construct useful according to the invention includes a geminiviral replicase gene encoding a Rep protein under the control of a fruit ripening-dependent promoter. A preferred fruit ripening-dependent promoter is selected from the fruit specific promoter tomato E8 (described in Deikman et al., 1992, *Plant Physiol.*, 100:2013), the seed specific promoter *Arabidopsis thaliana* 2S-2 (described in Guerche et al., 1990, *The Plant Cell*, 2:469), or the ethanol-inducible promoter (described in Caddick et al., *Nature Biotech.*, 16:177). Additional fruit ripening promoters useful according to the invention include the CaMv 35S promoter, the soybean seed protein glycinin (Gy1) promoter, the patatin tuber specific promoter and the inducible AlcA promoter. The mas, soybean vegetative storage protein (vsp), gbss, glucocorticoid, estrogen, jasmonic acid, insecticide RH5992, copper, tetracycline, and alchohol-inducible promoters are also useful fruit ripening-dependent promoters according to the invention.

A nucleotide sequence of interest of the invention is preferably operably linked at its 3' end to a plant-functional termination sequence. Preferred termination sequences include nopaline synthase (nos), vegetative storage protein (vsp), protease inhibitor 2 (pin2), and geminiviral short intergenic (sir) termination sequences.

A DNA construct of the invention can be single-stranded, as in the native geminiviral genome. Also, the DNA can be in its double-stranded replicative form, which includes a complementary strand. As used herein, the term "transgene" refers to a nucleotide sequence encoding a protein of interest together with the regulatory features necessary to effect transcription of the coding sequence. Such a transgene can be synthesized directly or derived from a genomic or cDNA library, and additionally may be amplified, such as by the polymerase chain reaction (PCR), according to methods well known in the art and described in Maniatis, supra, Ausubel, supra).

Another aspect of the present invention is an expression vector comprising an aforementioned DNA construct of the invention. Such a vector includes a selectable marker gene and a multiple cloning site into which is inserted a nucleic acid sequence comprising at least a portion of a long intergenic region (LIR) of a geminivirus genome operably linked to a nucleotide sequence encoding a protein of interest. Preferably, the nucleic acid sequence lacks a functional geminiviral coat protein encoding sequence, as produced by deleting all or part of this sequence. An expression vector of the invention also preferably has an *E. coli* origin of replication, in order to permit the use of conventional techniques in producing clones of the construct.

Marker genes useful according to the invention may include a gene encoding a selectable marker, e.g., an antibiotic resistance gene such as the bacterial tetracycline resistance gene. Incorporation of the tetracycline resistance gene permits the use of tetracycline as a selective agent in the plasmid preparation procedure according to the invention. One advantage to the use of a tetracycline resistance gene is that tetracycline is not degraded in *E. coli,* and therefore more tetracycline does not have to be added during fermentation. In addition, the tetracycline resistance gene is preferred over a gene encoding ampicillin resistance because tetracycline is prescribed less often as an antibiotic in a clinical setting, and therefore read through from the plasmid resistance gene will be less likely to interfere with the use of an antibiotic in a clinical setting.

Additional marker genes useful according to the invention include resistance to biocide, particularly an antibiotic, such as kanainycin, G418, bleomycin, hygromycin, chloramphenicol or the like. The particular marker employed will be one which allows for selection of transformed cells as compared to cells lacking the nucleic acid which has been introduced.

A vector can also have an *A. tumefaciens* origin of replication, such as when it is desired to maintain the vector in *A. tumefaciens* for later transformation with this system. In this event, the nucleotide sequence encoding a protein of interest is flanked by the left and right T-DNA border regions to effect its transfer to a host plant cell.

As used herein, the term "vector", and the like, refers to a nucleic acid construct capable of self-replication. Such a vector includes a plasmid, bacteria transformed with plasmids, phage vectors, cosmids, and bacterial and yeast artificial chromosomes. Generally, a vector of the present invention will be a plasmid, whether it is present in vitro, in *E. coli*, in *A. tumefaciens*, or as a nuclear episome of a plant. Suitable techniques for assembling the instant structural components into an expression cassette or replicon are described by Maniatis et al. (1982).

Figure 6:
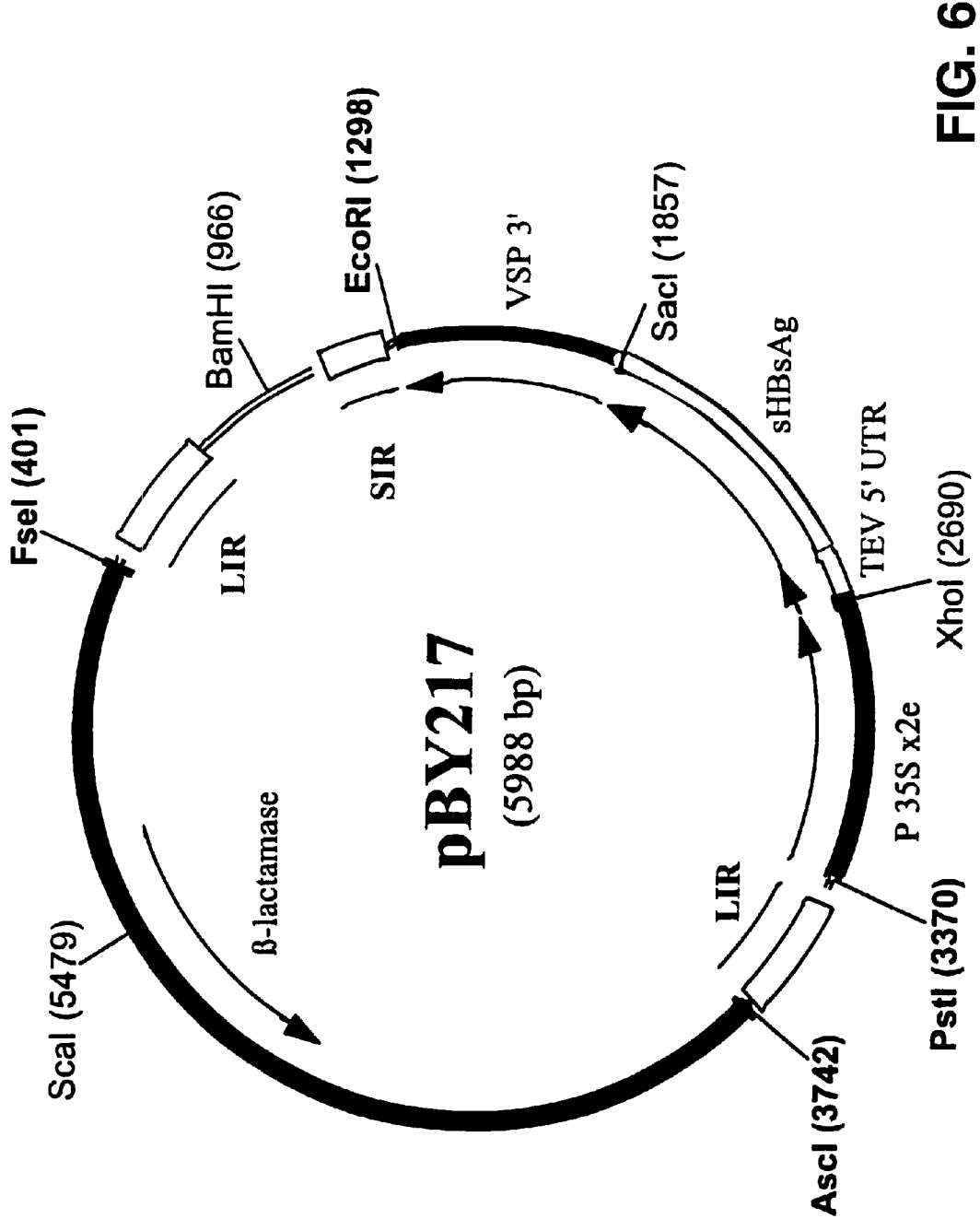
FIG. 6 is a plasmid map of pBY217.
Figure 24:
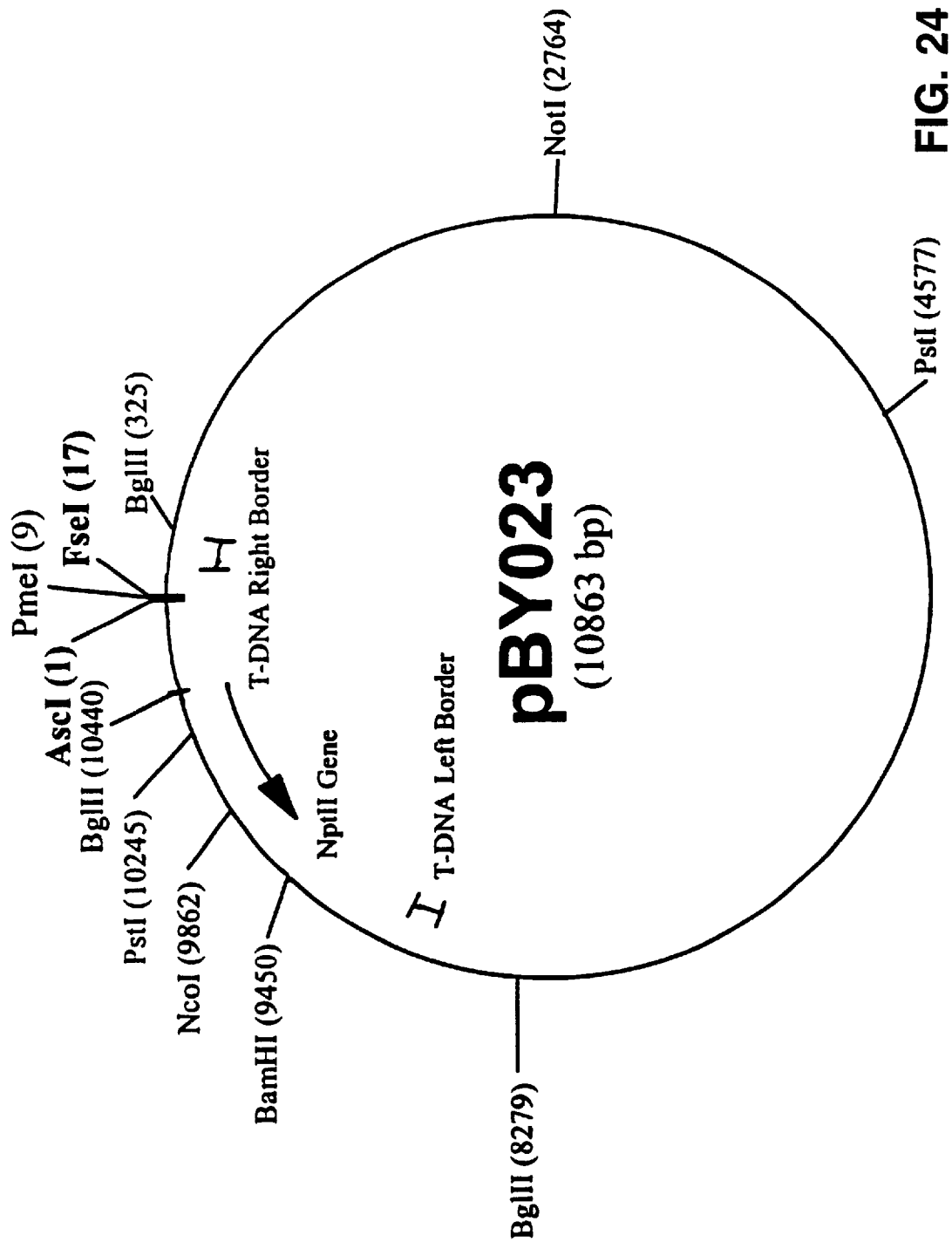
FIG. 24 is a plasmid map of pBY023.
Figure 25:
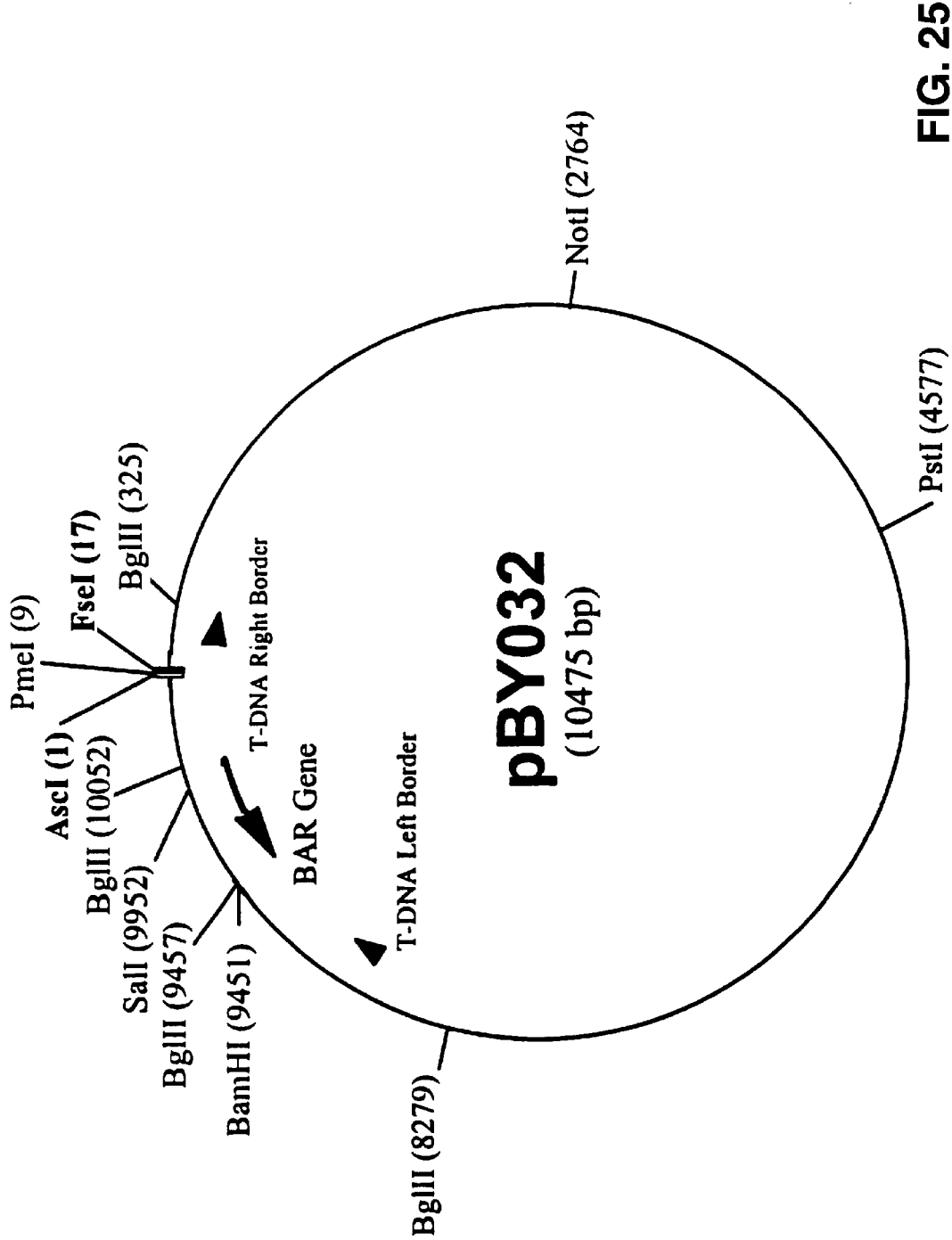
FIG. 25 is a plasmid map of pBY032.

Expression vectors useful according to the invention include pBY023 (FIG. 24) and pBY032 (FIG. 25). An expression vector comprising an expression cassette for hepatitis B surface antigen useful according to the invention is pBY217 (FIG. 6).

A strain of bacteria, such as *E. coli*, can be transfected with an expression vector of the present invention in order to grow/amplify an instant expression cassette according to methods well know in the art (Ausubel, supra, Maniatis, supra). The *E. coli* can also be mated with *A. tumefaciens* to introduce the vector therein, where it can reside intact as a shuttle vector. A helper Ti plasmid in the *A. tumefaciens* can provide the vir genes necessary to transfer the T-DNA directly from the shuttle vector to the plant cell. Alternatively, the vector can undergo homologous recombination with a tumor-inducing (Ti) plasmid and exchange the instant cassette for the T-DNA of the Ti plasmid. The invention therefore provides for producing transiently transformed plant cells wherein DNA constructs are maintained as episomes. Alternatively, the invention provides for methods of stably transforming plant cells wherein a DNA construct that is introduced into a plant cell is stably integrated into a chromosome.

Another strain of *A. tumefaciens* contains an expression vector of the present invention and a Ti plasmid that comprises a viral replicase encoding sequence, e.g., a mastrevirus rep sequence, in its T-DNA segment. Such a Ti plasmid preferably has the 5' end of the replicase encoding sequence operably linked to a fruit ripening-dependent promoter, which permits inducible replication and amplification of a gene of interest in planta. A preferred fruit ripening dependent promoter useful according to the invention includes but is not limited to tomato E8, patatin, mas, soybean seed protein glycinin (Gy1), soybean vegetative storage protein (vsp), gbss, estrogen, jasmonic acid, insecticide RH5992, copper, tetracycline, and alcohol-inducible promoters. Also, the 3' end of the replicase encoding sequence is preferably operably linked to a plant-functional termination sequence, such as a nos, vsp, pin2, or sir termination sequence.

III. Genes of Interest and Proteins of Interest According to the Invention

A. Proteins Useful According to the Invention

Preferred proteins of interest for use with the present invention include reporter molecules, such as firefly luciferase (GenBank # M15077), glucuronidase (GUS) (Genbank #AAC74698), green fluorescent protein (GFP) (GenBank #E17099), and enhanced versions thereof, particularly for use in optimizing the parameters of this expression system. Proteins of interest useful according to the invention also include antigenic proteins such as shigatoxin B (StxB) (Genbank #AJ132761), staphylococcus entero- toxin B (SEB)(GenBank #M11118), *E. coli* labile toxin B (LT-B)(GenBank#AB011677), *E. coli* labile toxin A subunit (LT-A) (GenBank #AB01 1677), Norwalk virus capsid protein (NVCP)(GenBank #AP093797), and hepatitis B surface antigen (BBsAg)(GenBank #AF090842). It is preferred that such antigenic proteins associate as antigenic particles and/or complexes when such association is necessary to impart umnunogenicity thereto. Repeats of aforementioned sequences, e.g., IR sequences, can be employed, when desired, to generate and/or stabilize larger nucleotide sequences and fusion proteins. Proteins useful according to the invention also include dimeric IgA, epithelial transport molecules, monoclonal antibodies and blood substitute proteins.

Proteins useful according to the methods of the invention also include but are not limited to proteins that are useful according to the invention, such as receptors, enzymes, ligands, regulatory factors, and structural proteins. Therapeutic proteins including nuclear proteins, cytoplasmic proteins, mitochondrial proteins, secreted proteins, plasmalemma-associated proteins, serum proteins, viral antigens and proteins, bacterial antigens, protozoal antigens and parasitic antigens are also useful according to the invention.

Therapeutic proteins useful according to the invention also include lipoproteins, glycoproteins, phosphoproteins. Proteins or polypeptides which can be expressed using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens and bacterial antigens. Specific examples of these compounds include proinsulin (GenBank #EOOO I1), growth hormone, dystrophin (GenBank # NM_007124), androgen receptors, insulin-like growth factor (GenBank #NM$_{13}$ 00875), insulin-ike growth factor II (GenBank #X07868) insulin-like growth factor binding proteins, epidermal growth factor TGF-o(GenBank #E02925), TGF-β (GenBank #AW008981), PDGF (GenBank #NM_002607), angiogenesis factors (acidic fibroblast growth factor (GenBank #E03043), basic fibroblast growth factor (GenBank #NM_002006) and angiogenin (GenBank #Ml 1567), matrix proteins (Type IV collagen (GenBank #NM_000495), Type VII collagen (GenBank #NM_000094), laminin (GenBank # J03202), phenylalanine hydroxylase (GenBank #K03020), tyrosine hydroxylase (GenBank #X05290), oncogenes (ras (GenBank #AF 22080), fos (GenBank #k00650), myc (GenBank #J00120), erb (GenBank #X03363), src (GenBank #AH002989), sis GenBank #M84453), jun (GenBank #J04111)), E6 or E7 transforming sequence, p53 protein (GenBank #AH007667), Rb gene product (GenBank #ml9701), cytokine receptor, IL-1 (GenBank #m54933), IL-6 (GenBank #e04823), IL-8 (GenBank #119591), viral capsid protein, and proteins from viral, bacterial and parasitic organisms which can be used to induce an immunologic response, and other proteins of useful significance in the body. The compounds which can be incorporated are only limited by the availability of the nucleic acid sequence for the protein or polypeptide to be incorporated. One skilled in the art will readily recognize that as more proteins and polypeptides become identified they can be integrated into the DNA constructs of the invention and used to transform plant seeds and plant cells and produce transgenic plants, useful for amplification of a gene of interest and overproduction of a protein of interest, according to the methods of the present invention.

B. Nucleotide Sequences Useful According to the Invention

1. Genes Encoding Toxins

Examples of genes useful in the invention include those encoding such agents including but not limited to genes encoding diphtheria toxin, Pseudomonas exotoxin, cholera toxin, pertussis toxin, etc., as follows. Diphtheria toxin-IL2 fusions for inhibition of HIV-1 infection (Zhang et al., 192, Jour. Acquired Immune Deficiency Syndrome 5:1181); Diphtheria toxin A chain for inhibition of HIV viral production (Harrison et al., 1992, AIDS Res. Hum. Retro. 8:39 and Curel et al., 1993, Hum. Gene Ther. 4:71); Diphtheria toxin A chain-liposome complexes for suppression of bovine leukemia virus infection (Kakidani et al., 1993, Microbiol. Immunol. 37:713); Diphtheria Toxin A chain gene coupled with immunoglobulin enhancers and promoters for B-cell toxicity (Maxwell et al., Cancer Res., 1991, 51:4299); Tat- and Rev-activated expression of a diphtheria toxin A gene (Harrison, 1991, Hum. Gene Ther. 2:53); Diphtheria toxin-CD4 fusion for killing of HIV-infected cells (Auilo et al., 1992, Eur. Mol. Biol. Org. Jour. 11:575).

Other toxins which are useful according to the invention include but are not limited to the following. Conditionally toxic retroviruses are disclosed in Brady et al., 1994, Proc. Nat. Aca. Sci. 91:365 and in Caruso et al., 1992, Bone Marrow Transplant, 9:187. Toxins against EBV infection are disclosed in Harris et al., 1991, Cell. Immunol. 134:85, and against poliovirus in Rodriguez et al., 1992, Jour. Virol. 66:1971. Toxins against influenza virus are disclosed in Bron et al., 1994, Biochemistry 33:9110.

2. Genes Encoding Immunoactive Agents

Another agent useful according to the invention includes irmunoactive agents, i.e., agents which combat viral infections or production by activating an immune response to the virus. Such agents include but are not limited to cytokines against viruses in general (Biron, 1994, Curr. Opin. Immunol. 6:530); soluble CD4 against SIV (Watanabe et al., 1991, Proc. Nat. Aca. Sci. 88:126); CD4-imnunoglobulin fusions against HIV-1 and SIV (Langner et al., 1993, Arch. Virol. 130:157); CD4(81–92)-based peptide derivatives against HIV infection (Rausch et al., 1992, Biochem. Pharmacol. 43:1785); lympho-cytotoxic antibodies against HIV infection (Szabo et al., 1992, Acta. Virol. 38:392); IL-2 against HIV infection (Bell et al., 1992, Clin Exp. Immunol. 90:6); and anti-T cell receptor antibodies against viruses in general (Newell et al., 1991, Ann. N.Y. Aca. Sci. 636:279).

3. Genes Encoding Anti-Viral Drugs

Genes encoding anti-viral agent useful according to the invention include genes encoding drugs having anti-viral activity and which are the direct product of a gene or are a product of a gene encoding a precursor of the drug, the drug then being synthesized by a biosynthetic pathway in the cell. Targets of drug intervention in the replicative cycle of, for example, a retrovirus, include (1) binding and entry, (2) reverse transcriptase, (3) transcription and translation, and (4) viral maturation and budding. Representative inhibitors of viral binding and entry for HIV include recombinant soluble CD4, immunoadhesions, peptide T, and hypericin. Nucleoside reverse transcriptase inhibitors include zidovudine, didanosine, zalcitabine, and starudine. Foscarnet, tetrahydroimidazobenzodiazepinethione compounds, and nevirapine are some non-nucleoside reverse transcriptase inhibitors. Inhibitors of transcription and translation include antagonists of the TAT gene and GLQ223. Castanospermine and protease inhibitors interfere with viral budding and maturation. Such drugs include but are not limited to nucleoside or nucleotide analogs and products of a cellular biosynthetic pathway such as described in Harrell et al., 1994, Drug Metab. Dispos. 22:124 (deoxy-guanine); Fillon et al., 1993, Clin. Invest. Med. 16:339 (dauno-rubicin); Ohrvi et al., 1990, Nucleic Acids Symp. 26:93 (anti-viral nucleosides); Hudson et al., 1993, Photochem. Photobiol. 57:675 (thiarubines); Salhany et al., 1993, Jour. Biol. Chem. 268:7643 (pyridoxal 5'-phosphate); Damaso et al., 1994, Arch. Viral. 134:303 (cyclosporin A); Gallicchio et al., 1993, Int. Jour. Immunol. 15:263 (dideoxynucleoside drugs); and Piore et al., 1990, Biol. Soc. Ital. Biol. Sper. 66:601 (AZT).

For many of these and other non-plant proteins, the nucleotide sequence encoding the protein is preferably optimized for expression in plants, e.g., by introducing one or more codons degenerate to the corresponding native codon. Other plant-optimization measures for coding sequences include removal of spurious mRNA processing signals such as polyadenylation signals, splicing sites, and transcription ternination signals, removal of mRNA destabilizing sequences, removal of the cytosine methylation motif "CCGG", modifying the translation start site and introducing a C-terminal KDEL signal (SEQ ID NO:9), such as SEKDEL (Ser-Glu-Lys-Asp-Glu-Leu) (SEQ ID NO:10), which presumably aids return of the nascent protein to the endoplasmic reticulum for processing.

A nucleotide sequence of interest of the present invention can be provided as its wild-type sequence. Alternatively, a synthetic sequence, such as a "plant-optimized" sequence mentioned above can be employed. A nucleotide sequence having a high degree of homology to these sequences, so that the encoded amino acid sequence remains substantially unchanged, are also contemplated. In particular, sequences at least 80%, more preferably 90%, homologous with an aforementioned nucleotide sequence are contemplated. It should be noted, however, that only that those epitopes of an expressed antigenic protein essential for generating the desired immune response need be present in the translated molecule. Accordingly, C- and/or N-terminal fragments, including portions of fusion proteins, presenting the essential epitopes are contemplated within the invention. Such fragments can be encoded in a vector construct of the invention or can be generated in vivo or in vitro by post-translation cleavage processes.

Additional proteins of interest useful according to the invention include Hepatitis B Surface Antigen, Norwalk Capsid Protein and *E. coli* heat-labile enterotoxin.

Hepatitis B Surface Antigen (HBsAg)

The feasibility of expressing HBsAg as virus-like particles (VLPs) in tobacco leaves has been demonstrated (Mason et al., 1992). The VLPs are similar to the recombinant yeast-derived vaccine, which is licensed for parenteral immunization. The formation of HBsAg particles requires insertion of the peptide in the endoplasmic reticulum (ER) membrane with four transmembrane domains, followed by budding of particles into the ER lumen. The plant-derived BBsAg retains both B- and T-cell epitopes when studied in a mouse model (Thanavala et al., 1995). The finding that plant cells can produce an immunogenic HBsAg VLP indicates that plants are a feasible expression system for aninal proteins that assemble into complex structures. Accordingly, the necessary genetic elements for generating immunogenic HBsAg particles have been identified. These elements, e.g., regulatory and coding regions, can be incorporated into a geminiviral vector as described herein to afford a means of amplifying expression of this antigen in plants, Norwalk Capsid Protein (NVCP)

The expression and VLP assembly in plants of NVCP, and its oral immunogenicity in mice have been reported (Mason et al., 1996). The NVCP accumulated to 0.3% of the total protein, and assembled into VLPs with about 60% efficiency in tobacco leaf and potato tuber cells. When viewed by negative staining electron microscopy, the empty capsids were virtually indistinguishable from those produced in an insect cell system. Further, the material was orally immunogenic in mice when given by gavage in 4 doses as low as 10 µg each, or when given by direct feeding of potato tuber slices in 4 doses as low as 50 µg each. Both serum IgG and gut mucosal IgA were stimulated by the plant vaccine. Thus, the means for generating immunogenic amounts of VLPs of NVCP antigens have been identified. These can be used with the present invention to generate yet higher levels of immunogen in plants according to the gene amplification methods described herein.

E. coli heat-labile enterotoxin (LT) LT is a potent mucosal immunogen and adjuvant that stimulates immune responses against co-administered antigens (Clements et al., 1988). The B-subunit of LT (LT-B) expressed in tobacco leaves assembles into active oligomers that possess ganglioside $G_{M1}$ binding capacity (Haq et al., 1995). It is found that addition of a microsomal retention sequence (SEKDEL) (SEQ ID NO:10) at the carboxyl-terminus of LT-B increases its accumulation in plant tissue, while still allowing $G_{M1}$ binding and immunogenicity. In oral tests with plant-derived LT-B given to mice, either tobacco leaf extracts administered by gavage or potato tubers fed without preparation (other than slicing) stimulated serum and gut mucosal antibodies against LT-B (Haq et al., 1995). The serum anti-LT-B from these animals showed inhibition of LT activity, indicating its potential value as a protective vaccine. In further experiments, great enhancement of LT-B expression is obtained when a plant codon-optimized gene is used (Table 1) (Mason et al. 1998). The necessary genetic machinery for expressing single copies of the LT-B gene in plants has therefore been identified. This approach can now be used in conjunction with the methods disclosed herein to achieve still higher levels of expression by way of gene amplification.

TABLE 1

Expression of different LT-B coding regions in potato leaves

| Coding region (plasmid) | Modification | Soluble LT-B, ng/mg |
| --- | --- | --- |
| Native LT-B (pLTB110) | Optimize translation start site | 70 |
| LTB-SEKDEL (pLTK110) | C-terminal SEKDEL (SEQ ID NO:10) extension | 190 |
| Synthetic LT-B (pTH110) | Plant-optimize codons, eliminate spurious polyadenylation and splicing signals | 4640 |

Oral Adjuvants

An edible vaccine of the present invention entails providing at least a portion of a transgenic plant generated as described herein. Preferably, the vaccine further comprises an immunologically acceptable adjuvant, i.e., one that promotes an immune response to the antigenic protein expressed by the plant without producing a serious deleterious effect. Preferred adjuvants include cholera toxin (CT), heat-labile enterotoxin (LT), anti-idiotypic antibody 2F10, colonization factor, shiga-like toxin, intimin, and mutants thereof.

The expression of E. coli heat-labile enterotoxin (LT) in plants as an oral adjuvant when co-expressed with other vaccine antigens has been explored. The goal is to produce assembled and active holotoxin LT ($A_1B_5$) in edible tissues. In early experiments using the native bacterial LT-A and LT-B coding sequences, potato transformants that express mRNAs (detected by Northern blot of total tuber RNA) for both LT-A and LT-B were detected, but holotoxin was not detected.

IV. Methods of Introducing Nucleic Acid into Cells

A. Transformation methods

Methods of gene transfer into plants include use of the *A. tumefaciens*—Ti plasmid system. The tumor-inducing (Ti) plasmids of *A. tumefaciens* contain a segment of plasmid DNA called transforming DNA (T-DNA), which integrates into the plant host genome. First, a plasmid vector is constructed that replicates in *E. coli* . This plasmid contains the DNA encoding the protein of interest and this DNA is flanked by T-DNA border sequences, which define the points at which the DNA integrates into the plant genome. Usually a gene encoding a selectable marker (such as a gene encoding resistance to an antibiotic such as kanamycin) is also inserted between the left border (LB) and right border (RB) sequences. The expression of this gene in transformed plant cells gives a positive selection method to identify those plants or plant cells having an integrated T-DNA region. Second, the plasmid is transferred to Agrobacterium. This can be accomplished via a conjugation mating system, or by direct uptake of plasmid DNA by the Agrobacterium. For subsequent transfer of the T-DNA to plants, the Agrobacterium strain utilized must contain a set of inducible virulence (vir) genes, which are essential for T-DNA transfer to plant cells.

The *A. tumefaciens* gene transfer system mentioned above is the etiologic agent of crown gall, a disease of a wide range of dicotyledons and gymnosperms [DeCleene, M. et. al., Bot. Rev. 42, 389 (1976)], that results in the formation of tumors or galls in plant tissue at the site the infection. The Agrobacterium system has been developed to permit routine transformation of a variety of plant tissue [see, e.g., Schell, J. et al., *Bio/Technology* 1, 175 (1983); Chilton, M-D, *Scientific American* 248, 50 (1983)]. Representative tissues transformed in this manner include tobacco [Barton, K. et al., Cell 32, 1033 (1983)]; tomato [Fillatti, J. et al., *Bio/Technology* 5, 726 (1987)]; sunflower [Everett, N. et al.,. *Bio/Technology* 5, 1201 (1987)]; cotton [Umbeck, P. et al., *Bio/Technology* 5, 263 (1987)]; rapeseed [Pua, E. et al., *Bio/Technology* 5, 815 (1987)]; potato [Facciotti D. et al., *Bio/Technology* 3, 241 (1985); poplar [Pythoud, F. et al., *Bio/Technology* 5, 1323 (1987); and soybean [Hinchee, M. et al., *Bio/Technology* 6, 915 (1988)]. Other plants can be transformed by routine extensions or modifications of these methods.

Multiple choices of Agrobacterium strains and plasmid construction strategies can be used to optimize genetic transformation of plants. For instance, *A. tumefaciens* may not be the only Agrobacterium strain used. Other Agrobacterium strains such as *A. rhizogenes* may be more suitable in some applications. *A. rhizogenes,* which incites root hair formation in many dicotyledonous plant species, carries a large extra-chromosomal element called an Ri (root-including) plasmid, which functions in a manner analogous to the Ti plasmid of *A. tumefaciens.* Transformation using *A. rhizogenes* has developed analogously to that of *A. tumefaciens* and has been successfully utilized to transform, for example, alfalfa, [Sukhapinda, K. et al., *Plant Mol. Biol.* 8, 209 (1987)].

Methods of inoculation of the plant tissue vary depending upon the plant species and the Agrobacterium delivery system. A convenient approach is the leaf disc procedure which can be performed with any tissue explant that provides a good source for initiation of whole plant differentiation. The addition of nurse tissue may be desirable under certain conditions. Other procedures such as in vitro transformation of regenerating protoplasts with *A. tumefaciens* may be followed to obtain transformed plant cells as well.

Several so-called "direct" gene transfer procedures have been developed to transform plants and plant tissues without the use of an Agrobacterium intermediate. Plant regeneration from protoplasts is a particularly useful technique [Evans, D. A. et al., *Handbook of Plant Cell Culture* 1, 124 (1983)]. When a plant species can be regenerated from protoplasts, direct gene transfer procedures can be utilized and transformation is not dependent on the use of *A. tumefaciens*. In the direct transformation of protoplasts the uptake of exogenous genetic material into a protoplast may be enhanced by use of a chemical agent or electric field. The exogenous material may then be integrated into the nuclear genome.

Early work has been conducted in the dicot *Nicotiana tabacum* (tobacco) where it was shown that the foreign DNA was incorporated and transmitted to progeny plants [Paszkowski, J. et al., *EMBO J,* 3: 2717 (1984); Potrykus, I. et al., *Mol. Gen. Genet.* 199: 169 (1985)]. Monocot protoplasts have also been transformed by this procedure: for example, *Triticum monococum* [Lorz H. et al., *Mol. Gen. Genet.* 199: 178 (1985)]; *Lolium multiflorum* (Italian ryegrass), Potrykus, I. et. al., *Mol. Gen. Genet* 199, 183 (1985); maize [Rhodes, C., et al., *Bio/Technology* 5, 56 (1988)]; and Black Mexican sweet corn [Fromm, M. et al., *Nature* 319, 719 (1986)]. Other plants that have been regenerated from protoplasts include rice [Abdulah, R. et al., *Bio/Technology* 4, 1987 (1987)]; rapeseed [Kansha, et al., *Plant Cell Reports* 5, 101 (1986)]; potato [Tavazza, R. et al., *Plant Cell Reports* 5, 243 (1986)]; eggplant, Sihachaki, D. et al., *Plant Cell, Tissue, Organ Culture* 11, 179 (1987); and cucumber [Jia, S-R., et al., J. Plant Physiol. 124, 393 (1986)]. Methods for directly transforming protoplasts of other varieties are evident.

Introduction of DNA into protoplasts of a plant can be effected by treatment of the protoplasts with an electric pulse in the presence of the appropriate DNA in a process called electroporation. In this method, the protoplasts are isolated and suspended in a mannitol solution. Supercoiled or circular plasmid DNA is added. The solution is mixed and subjected to a pulse of about 400 V/cm at room temperature for less than 10 to 100 microseconds. A reversible physical breakdown of the membrane occurs to permit DNA uptake into the protoplasts.

DNA viruses have been used as gene vectors in plants. A cauliflower mosaic virus carrying a modified bacterial methotrexate-resistance gene was used to infect a plant. The foreign gene was systematically spread in the plant [Brisson, N. et al., *Nature* 310, 511 (1984)]. The advantages of this system are the ease of infection, systematic spread within the plant, and multiple copies of the gene per cell.

Liposome fusion has also been shown to be a method for transformation of plant cells. In this method, protoplasts are brought together with liposomes carrying the desired gene. As membranes merge, the foreign gene is transferred to the protoplasts [Dehayes, A. et al., *EMBO J.* 4, 2731 (1985)].

Polyethylene glycol (PEG) mediated transformation has been carried out in *N. tabacum* (a dicot) and *Lolium multiflorum* (a monocot). It is a chemical procedure of direct gene transfer based on synergistic interaction between $Mg^{2+}$, PEG, and possibly $Ca^{2+}$ [ Negrutiu, R. et al., *Plant Mol. Biol.* 8, 363 (1987)]. Alternatively, exogenous DNA can be introduced into cells or protoplasts by microinjection. A solution of plasmid DNA is injected directly into the cell with a finely pulled glass needle.

A recently developed procedure for direct gene transfer involves bombardment of cells by microprojectiles carrying DNA [Klein, T. M. et al., *Nature* 327, 70 (1987)]. In this "biolistic" procedure, tungsten or gold particles coated with the exogenous DNA are accelerated toward the target cells. At least transient expression has been achieved in onion. This procedure has been utilized to introduce DNA into Black Mexican sweet corn cells in suspension culture and maize immature embryos and also into soybean protoplasts [Klein, T. M. et al., *Bio/Technology* 6, 559 (1988)]. Stably transformed cultures of maize and tobacco have been obtained by microprojectile bombardment. Stably transformed soybean plants have been obtained by this procedure [McCabe, D. E. et al., *Bio/Technology* 6, 923 (1988)].

To produce transformed seeds, flowers of Arabidopsis are transformedaccording to the following method. The Agrobacterium is vacuum-infiltrated into developing flowers, and the resulting seed are then screened for marker resistance and foreign gene expression. Presumably, stamens/pollen, ovary/egg, or even the developing zygote if fertilization has already occurred are transformed. This method (described in Clough & Bent, 1998, *Plant J.,* 16:735) is used to transform Arabidopsis with a construct comprising a rep gene under the transcriptional regulation of the At2S-2 seed promoter.

V. Plants, Cells and Seeds Useful According to the Invention

Plants that can be used for practice of the present invention include any dicotyledon and monocotyledon. These include, but are not limited to, tobacco, carrot, spinach, pepper, potato, tomato, apple, wheat, rye, soybean, rice, maize, corn, berries such as strawberries, raspberries, alfalfa and banana. Since many edible plants used by humans for food or as components of animal feed are dicotyledenous plants, dicotyledons are typically employed, although monocotyledon transformation is also applicable especially in the production of certain grains useful for animal feed. It is particularly advantageous in certain disease prevention for human infants to produce a vaccine in a juice for ease of administration to humans such as juice of tomato, soybean, and carrot, or milk. Cells and seeds derived from these plant vaccines are also useful according to the invention.

A transgenic plant transformed with a vector described hereinabove is another aspect of the present invention. Particularly preferred plant hosts for the vector include banana, tomato, potato and carrot.

Potato varieties FL 1607 ("Frito Lay 1607") and Desiree, and tomato variety Tanksley TA234TM2R are particularly preferred varieties, which have been transformed with binary vectors using the methods described herein. Of these transformed varieties, Desiree is the only commercial variety; the other varieties can be obtained from Frito-Lay (Rhinelander, Wis.) and Steve Tanksley (Dept. of Plant Breeding, Cornell Univ.). Potato variety FL1607 allows rapid transformation but is not a good agronomic variety as it suffers from hollow heart.

Tomato is preferred as a model system for expression of foreign proteins because of its ease of genetic transformation, and because fruit-specific, ripening dependent promoters are available for regulated expression (Giovannoni et al., 1989). The E8 promoter has been used to mediate high level production of polygalacturonase protein in mutant tomato fruit (Giovannoni et al., 1989) and monellin in wild-type tomato fruit (Penairubia et al., 1992). Tomato is a host for BeYDV (Palmer & Rybicki, 1997) and will therefore support Rep-mediated replication of viral DNA.

The important points for virus-mediated gene amplification in tomato, before developing the system in a more appropriate high-protein system such as soybeans, can be demonstrated. Soybean transformation is much more difficult than tomato, so it is prudent to show feasibility in the more tractable system. Upon showing the salient features of the system in soybeans, i.e., Rep protein expression in seeds and rescue of a vaccine antigen gene in a viral replicon, amplification of the transgene in soybean is established.

VI. Methods of Detecting Nucleic Acid and Protein According to the Invention

The invention provides for methods of detecting rescue and replication including but not limited to Southern and northern blot analysis, PCR-based methods of detection, as well as immunological methods of detecting a protein of interest according to the invention.

A. Detection of a Nucleotide Sequence of Interest

1. Southern Blot Analysis

Southern blot analysis can be used to detect a nucleotide sequence of interest from a PCR amplified product or from a total genomic DNA test sample via a non-PCR based assay. The method of Southern blot analysis is well known in the art (Ausubel et al., supra, Sambrook et al., 1989, *Molecular Cloning. A Laboratory Manual., 2nd Edition,* Cold Spring Harbor Laboratory Press, Cold Spring Harbor, N.Y.). This technique involves the transfer of DNA fragments from an electrophoresis gel to a membrane support resulting in the immobilization of the DNA fragments. The resulting membrane carries a semipermanent reproduction of the banding pattern of the gel.

Southern blot analysis is performed according to the following method. Genomic DNA (5–20 μg) is digested with the appropriate restriction enzyme and separated on a 0.6–1.0% agarose gel in TAE buffer. The DNA is transferred to a commercially available nylon or nitrocellulose membrane (e.g. Hybond-N membrane, Amersham, Arlington Heights, Ill.) by methods well known in the art (Ausubel et al., supra, Sambrook et al., supra). Following transfer and UV cross linking, the membrane is hybridized with a radiolabeled probe in hybridization solution (e.g. under stringent conditions in 5×SSC, 5×Denhardt solution, 1% SDS) at 65° C. Alternatively, high stringency hybridization can be performed at 68° C. or in a hybridization buffer containing a decreased concentration of salt, for example 0.1×SSC. The hybridization conditions can be varied as necessary according to the parameters known in the art. Following hybridization, the membrane is washed at room temperature in 2×SSC/0.1% SDS and at 65° C. in 0.2×SSC/0.1% SDS, and exposed to film. The stringency of the wash buffers can also be varied depending on the amount of the background signal (Ausubel et al., supra).

Detection of a nucleic acid probe-target nucleic acid hybrid will include the step of hybridizing a nucleic acid probe to the DNA target. This probe may be radioactively labeled or covalently linked to an enzyme such that the covalent linkage does not interfere with the specificity of the hybridization. A resulting hybrid can be detected with a labeled probe. Methods for radioactively labeling a probe include random oligonucleotide primed synthesis, nick translation or kinase reactions (see Ausubel et al., supra). Alternatively, a hybrid can be detected via non-isotopic methods. Non-isotopically labeled probes can be produced by the addition of biotin or digoxigenin, fluorescent groups, chemiluminescent groups (e.g. dioxetanes, particularly triggered dioxetanes), enzymes or antibodies. Typically, non-isotopic probes are detected by fluorescence or enzymatic methods. Detection of a radiolabeled probe-target nucleic acid complex can be accomplished by separating the complex from free probe and measuring the level of complex by autoradiography or scintillation counting. If the probe is covalently linked to an enzyme, the enzyme-probe-conjugate-target nucleic acid complex will be isolated away from the free probe enzyme conjugate and a substrate will be added for enzyme detection. Enzymatic activity will be observed as a change in color development or luminescent output resulting in a $10^3$–$10^6$ increase in sensitivity. An example of the preparation and use of nucleic acid probe-enzyme conjugates as hybridization probes (wherein the enzyme is alkaline phosphatase) is described in (Jablonski et al., 1986, *Nuc. Acids Res.,* 14:6115)

Two-step label amplification methodologies are known in the art. These assays are based on the principle that a small ligand (such as digoxigenin, biotin, or the like) is attached to a nucleic acid probe capable of specifically binding to a gene of interest.

According to the method of two-step label amplification, the small ligand attached to the nucleic acid probe will be specifically recognized by an antibody-enzyme conjugate. For example, digoxigenin will be attached to the nucleic acid probe and hybridization will be detected by an antibody-alkaline phosphatase conjugate wherein the alkaline phosphatase reacts with a chemiluminescent substrate. For methods of preparing nucleic acid probe-small ligand conjugates, see (Martin et al., 1990, *BioTechniques,* 9:762). Alternatively, the small ligand will be recognized by a second ligand-enzyme conjugate that is capable of specifically complexing to the first ligand. A well known example of this manner of small ligand interaction is the biotin avidin interaction. Methods for labeling nucleic acid probes and their use in biotin-avidin based assays are described in Rigby et al., 1977, *J. Mol. Biol.,* 113:237 and Nguyen et al., 1992, *BioTechniques,* 13:116).

Variations of the basic hybrid detection protocol are known in the art, and include modifications that facilitate separation of the hybrids to be detected from extraneous materials and/or that employ the signal from the labeled moiety. A number of these modifications are reviewed in, e.g., Matthews & Kricka, 1988, *Anal. Biochem.,* 169:1; Landegren et al., 1988, *Science,* 242:229; Mittlin, 1989, *Clinical Chem.* 35:1819; U.S. Pat. No. 4,868,105, and in EPO Publication No. 225,807.

2. Northern Blot Analysis

The method of Northern blotting is well known in the art. This technique involves the transfer of RNA from an electrophoresis gel to a membrane support to allow the detection of specific sequences in RNA preparations.

Northern blot analysis is performed according to the following method. An RNA sample (prepared by the addition of MOPS buffer, formaldehyde and formamide) is separated on an agarose/formaldehyde gel in 1×MOPS buffer. Following staining with ethidium bromide and visualization under ultra violet light to determine the integrity of the RNA, the RNA is hydrolyzed by treatment with 0.05M NaOH/1.5MNaCl followed by incubation with 0.5M Tris-Cl (pH 7.4)/1.5M NaCl. The RNA is transferred to a commercially available nylon or nitrocellulose membrane (e.g. Hybond-N membrane, Amersham, Arlington Heights, Ill.) by methods well known in the art (Ausubel et al., supra, Sambrook et al., supra). Following transfer and UV cross linking, the membrane is hybridized with a radiolabeled probe in hybridization solution (e.g. in 50% formamide/2.5% Denhardt's/100–200 mg denatured salmon sperm DNA/0.1% SDS/5×SSPE) at 42° C. The hybridization conditions can be varied as necessary as described in Ausubel et al., supra and Sambrook et al., supra. Following hybridization, the membrane is washed at room temperature in 2×SSC/0.1% SDS, at 42° C. in 1×SSC/0.1% SDS, at 65° C. in 0.2×SSC/0.1% SDS, and exposed to film. The stringency of the wash buffers can also be varied depending on the amount of background signal (Ausubel et al., supra).

3. PCR

Nucleic acid sequences of interest of the invention are amplified from genomic DNA or other natural sources by the polymerase chain reaction (PCR). PCR methods are well-known to those skilled in the art.

PCR provides a method for rapidly amplifying a particular DNA sequence by using multiple cycles of DNA replication catalyzed by a thermostable, DNA-dependent DNA polymerase to amplify the target sequence of interest. PCR requires the presence of a nucleic acid to be amplified, two single stranded oligonucleotide primers flanking the sequence to be amplified, a DNA polymerase, deoxyribonucleoside triphosphates, a buffer and salts.

The method of PCR is well known in the art. PCR, is performed as described in Mullis and Faloona, 1987, *Methods Enzymol.*, 155: 335, herein incorporated by reference.

PCR is performed using template DNA (at least 1 fg; more usefully, 1–1000 ng) and at least 25 pmol of oligonucleotide primers. A typical reaction mixture includes: 2 μl of DNA, 25 pmol of oligonucleotide primer, 2.5 μl of 10×PCR buffer 1 (Perkin-Elmer, Foster City, Calif. ), 0.4 μl of 1.25 μM dNTP, 0.15 μl (or 2.5 units) of Taq DNA polymerase (Perkin Elmer, Foster City, Calif.) and deionized water to a total volume of 25 μl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20–40 cycles consisting of denaturation (94–99° C. for 15 seconds to 1 minute), annealing (temperature determined as discussed above; 1–2 minutes), and extension (72° C. for 1 minute). The final extension step is generally carried out for 4 minutes at 72° C., and may be followed by an indefinite (0–24 hour) step at 4° C.

Several techniques for detecting PCR products quantitatively without electrophoresis may be useful according to the invention. One of these techniques, for which there are commercially available kits such as Taqman™ (Perkin Elmer, Foster City, Calif.), is performed with a transcript-specific antisense probe. This probe is specific for the PCR product (e.g. a nucleic acid fragment derived from a gene of interest) and is prepared with a quencher and fluorescent reporter probe complexed to the 5' end of the oligonucleotide. Different fluorescent markers can be attached to different reporters, allowing for measurement of two products in one reaction. When Taq DNA polymerase is activated, it cleaves off the fluorescent reporters of the probe bound to the template by virtue of its 5'-to-3' nucleolytic activity. In the absence of the quenchers, the reporters now fluoresce. The color change in the reporters is proportional to the amount of each specific product and is measured by a fluorometer; therefore, the amount of each color can be measured and the PCR product can be quantified. The PCR reactions can be performed in 96 well plates so that multiple samples can be processed and measured simultaneously. The Taqman™ system has the additional advantage of not requiring gel electrophoresis and allows for quantification when used with a standard curve.

B. Detection of a Protein Sequence of Interest

1. Preparation of Antibodies

Antibodies specific for the proteins of interest of the invention are useful for protein purification and detection. By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

Although a protein product (or fragment or oligopeptide thereof of a gene of interest of the invention that is useful for the production of antibodies does not require biological activity, it must be antigenic. Peptides used to induce specific antibodies may have an amino acid sequence consisting of at least five amino acids and preferably at least 10 amino acids. Preferably, they should be identical to a region of the natural protein and may contain the entire amino acid sequence of a small, naturally occurring molecule. Short stretches of amino acids corresponding to the protein of interest of the invention may be fused with amino acids from another protein such as keyhole limpet hemocyanin or GST, and antibody will be produced against the chimeric molecule. Procedures well known in the art can be used for the production of antibodies to the proteins of interest of the invention.

For the production of antibodies, various hosts including goats, rabbits, rats, mice etc . . . may be immunized by injection with the protein products (or any portion, fragment, or oligonucleotide thereof which retains immunogenic properties) of the genes of interest of the invention. Depending on the host species, various adjuvants may be used to increase the immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calnette-Guerin) and Corynebacterium parvum are potentially useful human adjuvants.

a. Polyclonal antibodies.

The antigen protein may be conjugated to a conventional carrier in order to increase its immunogenicity, and an antiserum to the peptide-carrier conjugate will be raised. Coupling of a peptide to a carrier protein and immunizations may be performed as described (Dymecki et al., 1992, *J. Biol. Chem.*, 267: 4815). The serum can be titered against protein antigen by ELISA (below) or alternatively by dot or spot blotting (Boersma and Van Leeuwen, 1994, *J. Neurosci. Mehtods*, 51: 317). At the same time, the antiserum may be used in tissue sections prepared as described. A usefull serum will react strongly with the appropriate peptides by ELISA, for example, following the procedures of Green et al., 1982, *Cell*, 28: 477.

b. Monoclonal antibodies.

Techniques for preparing monoclonal antibodies are well known, and monoclonal antibodies may be prepared using a candidate antigen whose level is to be measured or which is to be either inactivated or affinity-purified, preferably bound to a carrier, as described by Arnheiter et al., 1981, *Nature*, 294;278.

Monoclonal antibodies are typically obtained from hybridoma tissue cultures or from ascites fluid obtained from animals into which the hybridoma tissue was introduced.

Monoclonal antibody-producing hybridomas (or polyclonal sera) can be screened for antibody binding to the target protein.

2. Antibody Detection Methods

Particularly preferred immunological tests rely on the use of either monoclonal or polyclonal antibodies and include enzyme-linked immunoassays (ELISA), immunoblotting and immunoprecipitation (see Voller, 1978, *Diagnostic Horizons*, 2:1, Microbiological Associates Quarterly Publication, Walkersville, Md.; Voller et al., 1978, *J. Clin. Pathol.*, 31: 507; U.S. Reissue Pat. No. 31,006; UK Patent 2,019,408; Butler, 1981, *Methods Enzymol.*, 73: 482; Maggio, E. (ed.), 1980, *Enzyme Immunoassay*, CRC Press, Boca Raton, Fla.) or radioimmunoassays (RIA) (Weintraub, B., *Principles of radioimmunoassys*, Seventh Training Course on Radioligand Assay Techniques, The Endocrine Society, March 1986, pp. 1–5, 46–49 and 68–78). For analysing plants for the presence or absence of a protein of interest according to the present invention, immunohistochemistry techniques may be used. It will be apparent to one skilled in the art that the antibody molecule may have to be labelled to facilitate easy detection of a target protein. Techniques for labelling antibody molecules are well known to those skilled in the art (see Harlow and Lane, 1989, *Antihoies*, Cold Spring Harbor Laboratory).

VII. Uses

A. Gene Amplification

The constructs of the present invention can be used to amplify a gene of interest. According to the method of the invention, a gene of interest is amplified in the presence of a Rep protein, preferably about 10-fold, more preferably about 30-fold and most preferably about 100-fold, as compared to a gene of interest in the absence of a Rep protein.

B. Protein Production

The constructs of the present invention can be used to overproduce a protein of interest. According to the method of the invention, a protein of interest is overproduced in the presence of a Rep protein such that the amount of protein produced is preferably about 2%, more preferably about 10% and most preferably about 30% of the total protein of a cell comprising a construct of the invention that includes a nucleotide sequence encoding the protein of interest, and wherein the cell further comprises a Rep protein.

The invention will now be described with reference to certain examples, which illustrate but do not limit it.

EXAMPLES

Example 1

Verification of Rescue and Replication of a Chromosome-integrated rep-defective Viral Genome with BeYDV Rep Protein in trans Transgenic tobacco (*Nicotiana benthamian, Nicotiana tabacum*) plant lines are created by transformation with wild-type BeYDV partial dimer in a T-DNA binary vector (pBin19) using *A. tumefaciens* LBA4404. The plasmid pBeYDV1.4/Bin19 is described in Liu et al., 1998, *J. Gen. Virol.*, 79:2265. This plasmid includes the BeYDV 1.4-mer genome containing two LIR regions inserted into pBin19 (Bevan, 1984, Nuc. Acids. Res., 12:8711. As expected, the BeYDV genome integrates into the nuclear genomes of the plant cells. Some of the kanamycin-resistant transgenic plants displayed a stunty phenotype suggesting virus infection, while other lines appeared normal. DNA was isolated from plant leaves.

A Southern blot of plant leaf DNA was probed with labeled BeYDV genomic DNA, which revealed the presence of replicative forms of BeYDV DNA in the stunty plants. Normal plants, as well as plants transformed with the pBin19 vector, showed an absence of replicative forms of the DNA. It is believed that in those non-replicating transgenic lines, the site of insertion into the plant chromosome may limit expression of the Rep protein. Electron microscopy of thin sections of the leaves from stunty transgenic lines revealed the presence of crystalline arrays of virions characteristic of geminivirus-infected plants, and negatively stained leaf extracts showed geminate virus particles. These results demonstrate that integrated BeYDV genomic DNA can be rescued and replicated in some transgenic lines.

Example 2

Plant-optimized Genes for Shigatoxin B Subunit (StxB) and Staphylococcal Enterotoxin B (SEB)

StxB and SEB native sequences were scanned for codon use and for potential problem sequences, including spurious mRNA processing signals such as polyadenylation signals, splice sites, transcription termination signals, mRNA destabilizing sequences such as "ATTTA" [Ohme-Takagi M. et al. (1993) "The effect of sequences with high AU content on mRNA stability in tobacco," *Proc. Natl. Acad. Sci. USA* 90:11811–11815], "DST" sequences [Newman TC and Ohme-Takagi M, (1993) "DST sequences, highly conserved among plant SAUR genes, target reporter transcripts for rapid decay in tobacco" *Plant Cell* 5:701–714], and the cytosine methylation motif "CCGG". Plant-optimized genes were designed that use plant-preferred codons and lack the potential problem sequences. The designed genes for StxB and SEB were then assembled from overlapping oligonucleotides using the method described by Stemmer et al. [Stemmer WPC, et al. (1995) "Single-step assembly of a gene and entire plasmid from large numbers of oligodexoyribonucleotides," *Gene* 164:49–53]. The synthetic genes were cloned and sequenced to verify the desired nucleotide sequence.

Example 3

Assembly of StxB and SEB Genes into Expression Cassette with Enhanced 35S Promoter and TEV Leader; Transfer into pSK-BDY1.4H Vector and Transformation of Tobacco The verified synthetic StxB and SEB genes were cloned into the plant expression cassette pIBT210 [Haq TA, et al. (1995) "Oral immunization with a recombinant bacterial antigen produced in transgenic plants," *Science* 268:714–716], where they are flanked 5' by the enhanced CaMV 35S promoter and TEV leader. The HindIII/SacI fragments from these constructs, containing the enhanced CaMV 35S promoter and TEV leader fused to the coding sequence, are ligated separately with the BeYDV elements from a modified pSK-BYD1.4 [Liu L, et al. (1998) "Mutational analysis of bean yellow dwarf virus, a geminivirus of the genus Mastrevirus that is adapted to dicotyledonous plants," *J. Gen. Virol.* 79:2265–2274]. Plasmid pSK-BYD1.4 is modified by filling the HindIII site within the rep gene and re-ligating to introduce a frameshift in the rep coding sequence, and then introducing a HindIII site within the movement protein gene by site-directed mutagenesis, to form pSK-BDY1.4H. Digestion of pSK-BDY1.4H with HindIII and SacI removes the coat protein gene and part of the movement protein gene, and ligation of the HindIII/SacI fragments described above (35S-TEV-StxB or 35S-TEV-SEB) causes fusion of the cassettes within the BeYDV replicon such that the coat protein gene polyadenylation signal downstream of the SacI site is utilized. The recombinant replicons are then removed from these constructs using SpeI digestion, and these fragments are ligated into pBin19 digested with XbaI to yield T-DNA vectors for use with Agrobacterium. These T-DNA constructs in Agrobacterium are used to transform tobacco as described [Mason H, et al. (1993) "Identification of a methyl jasmonate responsive domain in the soybean vspB promoter," *Plant Cell* 5:241–251].

Example 4

Transformation of Tomato with Tandem Repeat of Mutant Viral Genome

Transgenic tomatoes containing a tandemly repeated copy (partial dimer) of the viral genome, which contains a marker gene (GUS) in place of the viral coat protein gene (FIG. 3A), are produced. In this case, transcription of GUS is driven by the BeYDV coat protein promoter. In another application, the coat protein gene can be replaced by an entire expression cassette containing GUS operably linked 5' to a promoter such as CaMV 35S and 3' to a polyadenylation signal such as soybean vsp. The rep gene is inactivated by site-directed mutagenesis. The transgenic plants generated therefore contain a chromosomally integrated, replication-defective and GUS-encoding copy of the viral genome. Initially, superinfection of the transgenic plants as a model system is used to establish whether tissue specific expression of the viral rep protein will induce amplification of expression of transgenes linked to the viral origin of replication. The wild type virus can be tested for its ability to rescue and amplify an integrated copy of a disarmed viral genome by infecting the transgenic plants with wild type BeYDV using either agroinfection or biolistic inoculation of virus DNA. The infected plants are monitored for appearance of viral symptoms. Amplification of the integrated viral genome in infected plants is monitored by Southern hybridization, and the expression of the GUS gene is monitored by the standard fluorometric assay (Jefferson et al., 1987).

Example 5

Demonstration of Fruit-specific and Ripening Dependent Expression of BeYDV Rep Protein in Trangenic Tomato Plants, Using the E8 Promoter Tissue-specific expression of Rep is preferred, because it may be toxic to plant cells and interfere with growth and development if constitutively expressed. Transgenic tomato plants are therefore produced that contain the BeYDV rep gene under the control of the E8 promoter, which is known to be strongly expressed during fruit ripening and is shut off in vegetative tissues. These plants are grown to maturity and tested for rep expression in different tissues at different developmental stages by Northern blot. The activity of the Rep protein in ripening fruit is demonstrated by biolistic delivery of the replication-defective GUS-encoding replicon from Example 4, and replication is monitored by Southern blot and GUS assay.

Example 6

Transgenic Tomato Plants with the ES-rep Cassette and a Reporter Gene (GUS) Expression Cassette Linked to a MeYDV Replicon Transgenic tomato plants that contain a viral replicon (with the rep gene inactivated) linked to a GUS-encoding cassette are produced. These plants are sexually crossed with the E8-rep plants from Example 5 to obtain plants transgenic for both cassettes. Double transgenic lines in the progeny are selected by PCR and Southern blot of genomic DNA. When these plants are grown to maturity, expression of the Rep protein during fruit ripening is expected to result in rescue of the recombinant viral replicon from the chromosome in fruit tissues, and enhanced expression of the linked GUS gene should be observed.

Example 7

Demonstration of Fruit-specific and Ripening Dependent Enancement of Expression of GUS in Transgenic Tomato The double transgenic lines generated in Example 6 are probed by Northern blot to verify fruit-specific and ripening-dependent expression of rep. GUS activity is examined at different stages of fruit ripening, and the results are compared to the GUS-only lines of Example 6 to determine the level of enhancement of expression mediated by co-expression of rep.

Example 8

Demonstration of Speed-specific and Ripening Dependent Expression of BeYDV Rep Protein in Transgenic Soybean Plants Using the Glycinin Gy1 Promoter The production of large amounts of a protein of interest is more practical in a crop like soybean, where substantial amounts of protein are stored in seeds. It is important to show seed-specific rep gene expression and its ability to amplify a gene of interest-BeYDV replicon in seeds of soybean.

An expression cassette is constructed with the BeYDV rep expression driven by a all soybean seed storage protein (glycinin) Gy1 promoter (Iida et al., 1995), linked to a hygromycin selectable marker (Stewart et al., 1996). This construct is used to produce transgenic soybean lines by biolistic DNA delivery (Christou et al., 1990; Stewart et al., 1996). A soybean cultivar with high embryogenic capacity, Glycine max L. Merrill "Jack" is used in order to facilitate transformation. Embryogenic cultures are induced by plating immature cotyledons on a Murashige and Skoog-based medium supplemented with 40 mg/liter of 2,4-dichlorophenoxyacetic acid (2,4-D). The embryogenic cultures are maintained in liquid medium containing 5 mg/liter 2,4-D. These cultures are used for microprojectile delivery of the transformation construct. The explants are then cultured for selection on 25 mg/liter hygromycin. Resistant embryogenic cell lines are transferred to growth regulator-free medium to permit recovery of mature somatic embryos. After a desiccation period, the somatic embryos are returned to growth regulator-free medium for conversion into plants. The transformed lines are examined for foreign DNA copy number and integrity by PCR and Southern blot. Transformants are grown to maturity to verify seed specific expression of Rep, after extraction of proteins as described (Vitale et al., 1984). It is important to determine whether the seeds produced in these plants are viable, so that the plants can be used as parental lines in sexual crosses; however, it is possible to produce double transgenic lines by incorporating two different cassettes into a single vector plasmid.

Example 9

Production of Transgenic Soybean Plants with a Model Vaccine Antigen Expression Cassette Linked to a BeYDV Replicon A tandemly repeated (partial dimer) BeYDV replicon containing the Norwalk virus capsid protein gene (NVCP) (Mason et al., 1996) in place of the BeYDV capsid gene is constructed, as described in Example 4 for the GUS-containing replicon. This DNA is used to transform soybean plants by biolistic DNA delivery (Stewart et al., 1996). Those plants containing a single copy of the replicon using PCR and Southern blot analysis are selected.

Example 10
Sexual Crossing of Transgenic Soybean Lines

The soybean lines obtained in Examples 8 and 9 are sexually crossed and seed-specific enhancement of expression of NVCP is demonstrated. The NVCP-BeYDV plants are grown to maturity and sexually crossed with the Rep-expressing plants described in Example 8. Progeny plants are screened for chromosomal copies of the NVCP replicon and the Rep gene cassette by PCR and Southern blot. Lines containing both of the foreign DNAs or the NVCP replicon only can be grown to maturity to compare expression of NVCP in seeds by ELISA as described elsewhere (Mason et al., 1996).

Example 11

Transformation of Potato Plants with *A. tumefaciens*

With potato, it is preferred to express the rep gene with a tuber specific promoter such as patatin or gbss. In plants containing an integrated rep-deficient BeYDV replicon, initiation of rep expression in tubers will promote rescue and replication of the integrated replicon. The stable transformation of potato (*Solanum tuberosum* "Frito-Lay 1607") is achieved by axenic leaf disc co-cultivation as described elsewhere [Haq, T. et al. (1995) *Science,* 268:714–716; Wenzler, H. et al. (1989), *Plant Science* 63: 79–85].

Precultivation—explants are cut and put abaxial side up on LCI plates for 3–4 days;

Inoculation—explants are placed in agro dilution for 10 minutes (agitation by hand), then blotted on sterile paper towel;

Cocultivation—after blotting, explants are put abaxial side up back on LCI plates for 3–4 days Selection: Callus induction—after cocultivation, explants are put on LC1CK plates containing kanamycin and carbenicillin for 5–7 days until callus is developed;

Shooting—explants with well developed callus are placed in LC2CK boxes for 2 weeks; after 2 weeks explants are placed on fresh LC2CK media and shoots are developed.

When the shoots are about 1.5 cm in length, they should be transferred to cm media for root formation. Carbenicillin is added to cm media to prevent bacterial growth in excess.

Growing Agrobacterium—LB stock: one colony is cultured overnight in presence of kanamycin; YM stock: one colony is cultured over a 36–48 hour period in the presence of kanamycin.

Because some variation in expression among independent transformation events is expected due to random site of insertion, independent transgenic lines are screened by Northern blot using coding region-specific probes. When a 35S promoter is used, the total RNA from leaves is screened. When the patatin promoter is used, RNA is obtained from microtubers developed in axenic culture. The patatin promoter constructs are screened from microtubers generated by subculture of stem node cuttings from nascent transformed shoots on media high in sucrose. The most promising transformed lines are propagated by axenic culture of node cuttings; and rooted plantlets are transplanted to soil and grown in the greenhouse.

To obtain tubers, the plants are grown in a two-stage protocol: (1) for the first 1.5–2 months, or until sufficient vegetative growth develops, using long day (16 h) lighting with supplemental lighting in winter, and (2) for an additional 1.5–2 months under short day (12 h) conditions. The tubers are typically recovered in yields of 600–800 g per 3-gallon pot after this 3–4 month regime. Tubers harvested from the first crop can be used to initiate new plants after a 1-month dormancy period.

Example 12

Transformaton of Tomato Plants (as modified from Frary/Fillati et al. (1987) *Biotechnology* 5:726–730)

Preparation of Plant Material

Sterilize seed a.) Immerse seed (Tanksley TA234TM2R) in 20% CHLOROX bleach for 20 min. (100 seeds~380 mg)

b.) Rinse well with sterile milli-Q water (2 or more times.)

Sow seed in Magenta boxes containing ½ MSO (approximately 30 seeds/box)

Prepare feeder layer (one day prior to cutting cotyledons).

a.) Pipet 2 mL of a one week old NT-1 suspension culture onto a KCMS media plate. (NT-1 cells are subcultured weekly (2:48) in KCMS liquid medium.)

b.) Cover suspension with a sterile 7 mc. Whatman filter c.) Culture in dark, overnight 4.) Cut cotyledons 8 days after sowing.

Place seedling on a sterile paper towel moistened with sterile water

Excise cotyledon at petiole and cut tips off. Cut in half again if size of cotyledon is >1 cm.

c.) Place explants on feeder plates adaxial side down d.) Culture 25° C., 16 hour photoperiod, overnight Transformation 1.) Streak Agrobacterium onto LB selective media plate about 1 week prior to transformation. Incubate at 30° C.

2.) Inoculate liquid selective medium.

Pick a single colony off of streaked plate, put into 3 mL YM medium with 150 $\mu$g Kanamycin Sulfate. Shake vigorously at 30° C. for 48 hours.

Pipette 1 mL of inoculate into 49 mL YM medium with 2.5 mg Kanamycin Sulfate and culture in 250 mL flask shaking vigorously at 30° C. for 24 h.

Measure O.D. of Agro culture using a spectrophotometer at 600 nm. Optimum O.D. equals 0.5 to 0.6.

Prepare Agro culture for transformation.

Centrifuge Agro culture at 8,000 rpm (Sorvall centrifuge, ss34 rotor) for 10 min.

Pour off YM and resuspend in MS—O, 2%. Final O.D. should be between 0.5 and 0.6.

5.) Incubate explants in Agro culture/MS—O,2% a.) Pipette 25 mL of Agro culture into a sterile Magenta box.

b.) Transfer explants from 2 to 3 plates into inoculum in magenta box.

c.) Incubate for 5 min. with occasional shaking.

d.) Remove explants to a sterile paper towel.

e.) Return explants to feeder plates, adaxial side down.

Seal plates with Nesco film.

6.) Cocultivate explants, 16-hour photoperiod, 25° C., for approximately 24 h.

Transfer explants to selection media (2Z) adaxial side up. Seal plates with micropore tape. Return to 25° C., 16-hour photoperiod.

Transfer explants to new IZ selection medium plates every 3 weeks. When shoots begin to appear transfer to IZ Magenta boxes.

Regeneration/Rooting
 Within 4 to 6 weeks initial shoots should appear.
 Excise shoots from explants when shoots are at least 2 cm. and include at least 1 node.
  Place in Magenta boxes (4/box) containing Tomato Rooting Media with selective agents.
 Roots should begin to appear in about 2 weeks.

Example 13

Regeneration of Transgenic Tomatoes
Standard Greenhouse Growth Conditions
16 hour day
average Temperature: 24.5° C.
fertilized each time watered: 100 ppm. EXCELL (15–5–15) with extra Calcium and Magnesium
Potatoes grown in METRO-MIX 360
Tomatoes grown in Cornell Mix+OSMO
Biological controls are used whenever possible to improve overall plant quality The present invention has been described with reference to particular examples for purposes of clarity and understanding. It should be appreciated that certain improvements and modifications of the invention can be practiced within the scope of the appended claims and equivalents thereto.

Example 14

Creation of Transgenic Plants with pBeYDV1.4/Bin19

Transgenic tobacco (*Nicotiana benthamiana, Nicotiana tabacum*) plant lines were created using the BeYDV genome in the vector pBeYDV1.4/Bin19 (Liu et al., supra) according to the methods described above, in order to demonstrate that an integrated viral genome can be excised and replicated.

Some of these transgenic tobacco plants displayed a stunty phenotype suggesting virus infection, while other transgenic tobacco lines appeared normal. Southern blot analysis of plant leaf DNA probed with BeYDV genomic DNA demonstrates the presence of replicative forms of BeYDV DNA in the stunty plants, and the absence of replicative forms in normal plants or plants transformed with the vector alone (data not shown). These data demonstrate that integrated BeYDV genomic DNA can be rescued and replicated in some transgenic lines.

In the nonreplicating transgenic lines, the site of insertion into the plant chromosomal DNA may limit expression of the Rep protein, which is needed for excision and replication of the viral DNA.

Further, electron microscopy of thin sections of leaves from transgenic lines demonstrating a stunty phenotype revealed the presence of crystalline arrays of virions characteristic of geminivirus-infected plants. Negatively stained leaf extracts showed geminate virus particles (data not shown).

Example 15

Use of BeYDV Cassettes in Transient Assays with Tobacco Cells

To produce transgenic plants expressing the Rep gene in trans, a series of constructs containing the Rep gene under constitutive (35S), inducible (AlcA) and developmental (E8) promoters were prepared.

Figure 26:
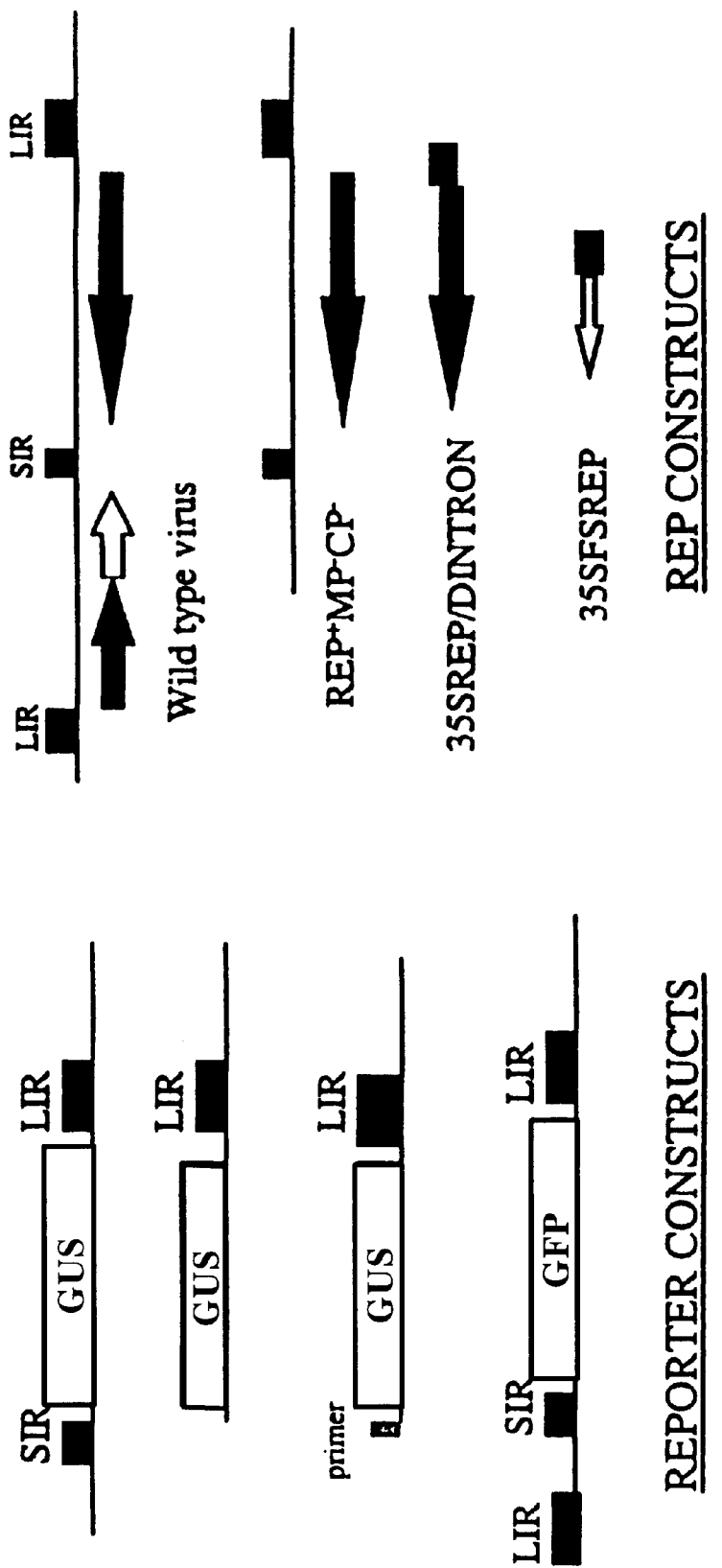
FIG. 26 illustrates BeYDV constructs.

It has been demonstrated that removal of the intron within the Rep gene greatly enhances BeYDV replication. Therefore, a series of clones containing this intronless form of Rep (Δintron) were also constructed. Reporter gene cassettes and Rep expression cassettes were constructed to test the replication of recombinant replicons in tobacco cells (FIG. 26).

Preliminary assessment of the ability of the BYDV based Green fluorescent protein (GFP) expression construct to replicate in-vivo when supplied with a Rep protein was tested by transient assays in tobacco NT-1 cell cultures. The GFP cassette was introduced into the cells by particle bombardment, either alone or in the presence of the self-replicating wild-type virus (FIG. 26).

Two days after bombardment, a high proportion of the cells in cultures bombarded with the GFP construct alone or with both constructs, exhibited a high level of GFP fluorescence (data not shown). The fluorescent signal in the cells bombarded with the GFP construct alone decreased rapidly as evident by a low number of residual cells that exhibited fluorescence and a low level of fluorescence after four days (data not shown). Six days after the bombardment, GFP could not be visualized in these cultures (data not shown). However, a high level of GFP was maintained in cultures of cells bombarded with both the replicating reporter construct and the Rep producing construct for at least 6 days (FIG. 24b and 24c). These results demonstrate replication of the GFP construct in the presence of trans-acting Rep protein, but not in the absence of Rep.

Primers designed in opposing orientations (GFP5': 5'-AGCTCGACCAGGATGG (SEQ ID NO:11) and GFP3': 5=-GTCCTGCTGGAGTTCG) (SEQ ID NO:12) were used to determine whether Rep expression in trans is capable of promoting nicking and religation of the GFP expression cassette, indicative of the occurrence of Rep-mediated replication. PCR products of the predicted 2 kb size were detected from total DNA isolated from cells bombarded with the GFP cassette in the presence of any of three different Rep producing plasmids that produce Rep, but not from DNA isolated from cells bombarded with the GFP cassette alone (data not shown). These data confirm that a Rep protein provided in trans can excise and replicate a replicon present on a different segment of DNA.

Figure 27:
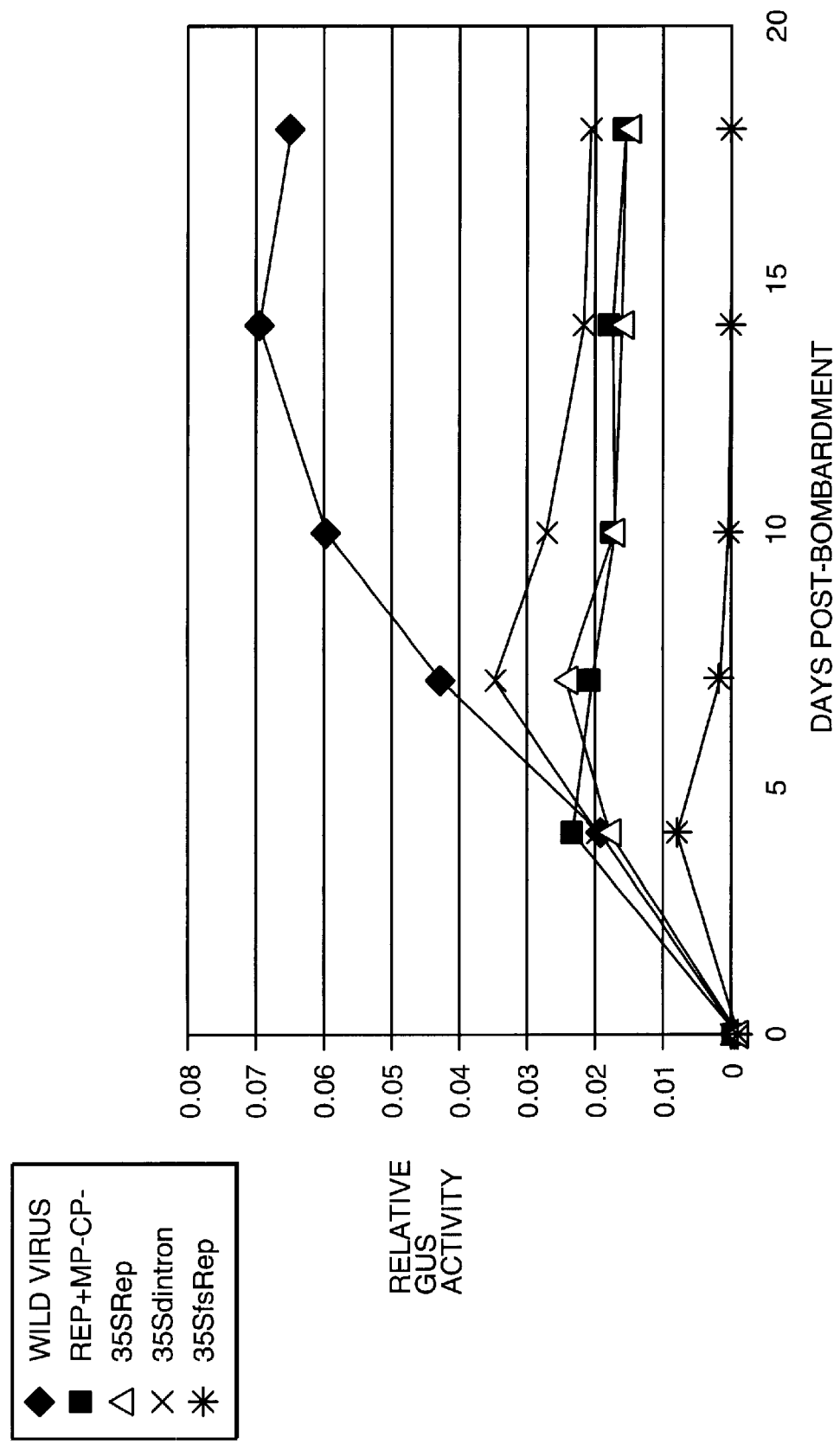
FIG. 27 is a graph illustrating the time course of GUS expression in NT1 cells.
Figure 28:
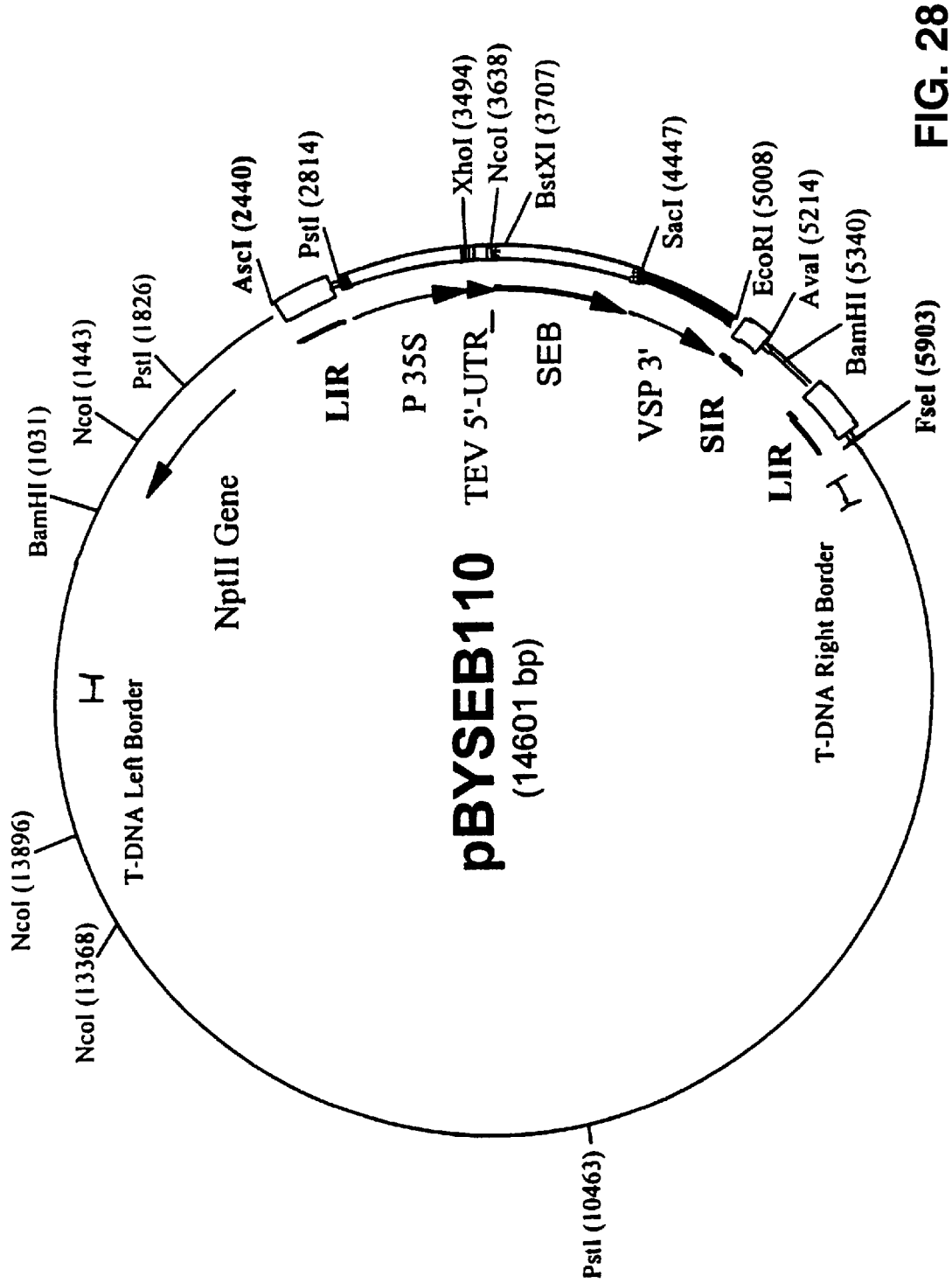
FIG. 28 is a plasmid map of pBYSEB110.

To gain a more quantitative estimate of the level of reporter gene expression from different constructs, a series of Rep constructs and GUS reporter cassettes were designed and cobombarded into NT-1 cells. Relative GUS activity was determined (FIG. 27). In FIG. 27, GUS expression is shown as a function of days after transfection wherein a GUS cassette was delivered with wild type virus (closed diamonds), 35SΔintron (X), REP+MP-CP-(closed squares), 35SRep (closed triangles) and 35SfsRep(*).

One week post-bombardment, GUS activity from cells cobombarded with both wild-type virus and the GUS expression cassette was found to be 8 times higher than cells bombarded with the GUS expression cassette alone. Similarly, GUS activity was found to be several fold higher in cells cobombarded with the expression cassette in the presence of the 35SRep construct, the Δintron constructs, or the Rep+MP-CP-construct, as compared to cells bombarded with the GUS expression cassette alone. No GUS activity could be detected from cells cobombarded with a frameshift version of 35Srep (35SfsRep) or from a GUS cassette containing an LIR but lacking an SIR (data not shown).

Over a three week period GUS activity was greatest in cells cobombarded with wild type virus; GUS levels increased for two weeks, then slowly declined, most likely due to the age of the cells. GUS activity in cells transfected with 35SRep and 35SΔintron was comparable to that obtained with the Rep+MP-CP-construct. In all cases, levels were greatest by 1 week post cobombardment and were maintained, demonstrating only a moderate decrease for the next two weeks. Cells cobombarded with 35SfsRep and the reporter cassette expressed GUS transiently at low levels for the first 4 days; by one week post-cobombardment, this activity was lost completely.

Example 16

Replication of a BYDV Based GFP Expression Construct in the Presence of a Rep Protein Producing Construct Construction of a Replicatable Expression Cassette The PstI-BamHI fragment containing the long intergenic region (LIR) of the Bean Yellow Dwarf Virus (BeYDV, cloned as a partial dimer in pBluescript (Stratagene), BY002. See FIG. 4) was cloned into pBlueScriptKS (Stratagene) to give pBY017 (FIG. 4). A fragment containing the short intergenic region (SIR) of BYDV was PCR amplified from the same plasmid using the primers SIRfor and SIRrev (see box 1, below) and cloned into pBY017 by replacing the short HindIII-EcoRI fragment to give BY019 (FIG. 4). The NheI-BamHI fragment of this plasmid that contains the LIR and the SIR, was cloned into pBY017 replacing the XbaI-BamHl fragment thus yielding pBY020 (FIG. 4). The insert that contains a tandem array of LIR-SIR-LIR was amplified from pBY020 by a two-step PCR by using the primers LIRAscI and SIRrev (Box 1, below). The resultant PCR fragment was used as a megaprimer together with the primer LIRFseI (Box 1, below) to amplify the full length LIR-SIR-LIR, now flanked by sites for the 8-base restrictases, AscI and FseI. This fragment was then cloned into a pUC19 derivative (pBY022, not shown), the multiple cloning region of which was replaced by a linker containing the restriction sites for AscI, FseI and PmeI. The resultant plasmid, pBY024 (FIG. 4), was sequenced and will serve as an intermediate vector for cloning of genes of interest between the PstI site and the EcoRI sites. The replicatable expression cassette is excised with AscI and FseI and cloned into a binary vector, a derivative of pGPTV-Kan (Becker et al., 1992, *Plant Mol. Biol.,* 20:1195) in which the HindIII-EcoRI fragment was replaced by the same linker described above (pBY023, not shown).

Box 1. Oligonucleotides used in this study.

```
Name: Sequence (SEQ ID NO:13)
SIRfor   5'-GGAATTCCGAGTGTACTTCAAGTCAGTTGG-3'

(SEQ ID NO:14)
SIRrev   5'-GGAAGCTTGGGATCCCTTCTATAATTCTTTGG-3'

(SEQ ID NO:15)
LIRAscI  5'-TGGCGCGCCGCTCTAGCAGAAGGCATGTTG-3'

(SEQ ID NO:16)
LIRFseI  5'-TTGGCCGGCCGTACGAATAATTCGTATCCGAC-3'

(SEQ ID NO:17)
LinkUP   5'-AGCTGGCGCGCCGTTTAAACGGCCGGCC-3'

(SEQ ID NO:18)
LinkDown 5'-TTAACCGGCCGGCAAATTTGCCGCGCGG-3'
```

Construction of reporter constructs

Two reporter gene expression cassettes were inserted into the replicatable pBY024 plasmid described above. First, the gene encoding the green fluorescence protein (GFP) containing the TEV-5'UTR and the nos-3'UTR, under the control of the Cauliflower Mosaic Virus 35S promoter with double enhancer (35S) was cloned between the PstI and EcoRI restriction sites of pBY024 to yield pBY027 (FIG. 4). This construct was used in a transient expression study to verify its replicatability (see below). Another reporter gene, UidA (under the control of the 35S promoter with the TEV-5'UTR and the 35S-3'UTR) was cloned into the PstI site (pBY028, FIG. 4). This construct is used to produce more quantifiable assessments (by the GUS assay) of the level of expression with the gemivirus construct. These constructs are cloned into binary vectors (by methods well known in the art) for the creation of transgenic plants.

Replication of the plasmid pBY027 by an infectious clone of BYDV

Preliminary assessment of the BYDV based GFP expression construct, pBY027, to replicate in-vivo when supplied with the replication associated protein of BYDV (Rep/RepA) was tested by transient assays in NT-1 cell cultures. The plasmid pBY027 was introduced into the cells by particle bombardment, either alone or with the self-replicating BYDV construct pBY003 (alias pBeYDV1.4/Bin19, Liu et al., supra).

Two days after bombardment, a high proportion of the cells in culture that were bombarded with the pBY027 alone or with both plasmids, exhibited a high level of GFP expression (data not shown). The levels of GFP in the cells bombarded with the expression construct alone decreased rapidly as demonstrated by the residual number of cells that exhibited fluorescence and the level of the fluorescence after four days (FIG. 27*a*). Six days after the bombardment, GFP could not be visualized in these cultures (data not shown). However, high levels of GFP was maintained in cultures of cells bombarded with both the replicating reporter construct and the Rep/RepA producing construct for at least 6 days (FIGS. 27*b* and 27*c*). These results indicate that replication of the reporter construct occurs in the presence of trans-acting Rep protein and not in its absence.

Exanple 17

Production of Transgenic Plants with SEB-F44S Gene

An expression cassette for the plant-optimized SEB-F44S gene under the control of the constitutive 35S promoter was constructed (FIG. 28), and used to transform potato. The expression cassette for SEB-F44S is driven by the constitutive Cauliflower Mosaic Virus 35S promoter linked to the Tobacco Etch Virus 5'-UTR, and flanked 3' by the soybean vspB 3' element.

Plants are regenerated on selective medium and screened for SEB expression by ELISA two weeks later when the potato plantlets are large enough. An ELISA assay is carried out in the presence of a positive control, SEB obtained from SIGMA. Selected lines are grown to maturity in the greenhouse.

Example 18

Construction and Testing of a BeYDV Construct

A BeYDV construct for insertion of expression cassettes that can form replication-competent episomes was constructed. This BeYDV construct contains 2 copies of the long intergenic region (LIR) flanking the short intergenic region (SIR) and a polylinker site for insertion of expression cassettes (FIG. 5, pBY024). We have inserted cassettes for expression of SEB-F44S (FIG. 28), hepatitis B surface antigen (HbsAg)(pBY217, FIG. 20), and reporter genes GUS (pBY028, FIG. 8 and pBY029, FIG. 9) and GFP (pBY027, FIG. 7).

The HBsAg construct was tested by codelivery to tobacco NT1 cells in the presence or absence of pBY002 (FIG. 5) as a source of Rep expression. Cells were incubated either for 3 days or for 6 days. The cellular DNA of the transformed tobacco cells was analyzed by Southern blot (data not shown) either undigested (U) or after digestion with BamIHi (B) or DpnI (D). The Southern blot was probed with a $^{32}$P-labeled HBsAg sequence.

Undigested DNA isolated from cells transformed with pBY217 and pBY002 shows a strong signal at 2.3 kb that is entirely shifted to 3.0 kb after digestion with BamHI, which site is unique in pBY217. Since pBY217 is approx. 6.0 kb, the data shows that the cassette was excised and replicated as the 3.0 kb size expected. Cells transformed with pBY217 alone showed no signal, indicating that the plasmid concentration was too low to detect (data not shown). These data demonstrate that a construct comprising two copies of the long intergenic region (LIR) flanking the short intergenic region (SIR) and a polylinker site for insertion of expression cassette can be replicated when Rep is provided in trans.

Example 19
Production of Polyclonal Antiserum Against Rep and Detection of Rep During BeYDV Infection or Transient Expression in NT1 Cells Generation of antiserum against BeYDV Rep An intronless form of the Rep gene in pΔintron (Liu et al., supra) was PCR amplified using the primers 5'NcoRep CGG ATA ACA ATT TCA CAC AG (SEQ ID NO:19) and 3'BglIIRep CTC AGC TAA TTA AGC TTA (SEQ ID NO:20), and cloned into the NcoI and BglII sites of the plasmid QE60 (Qiagen) to produce the construct QE60Rep. This 6His-tagged version of Rep was purified using the standard Qiagen QIAExpress Kit and injected subcutaneously into a rabbit in a series of four doses of 0.5 mg of purified protein in PBS. The first dose was emulsified in Freund's complete adjuvant, followed 5 weeks later by a second dose in Freund's incomplete adjuvant, and third and fourth doses in Freund's incomplete adjuvant at 3-week intervals. The serum was obtain 3 weeks after the last dose and stored at −20° C.

Detection of Rep During BeYDV Infection or Transient Expression in NT1 cells

Tobacco NT1 cells were bombarded with various plasmids including pBY002 (native virus), pΔintron (virus with C1/C2 intron deleted), p35SRep, p35Sdintron, and p35SRepA. At 2, 4, 6, and 8 days after DNA delivery, cells were extracted and assayed by Western blot using the rabbit polyclonal antiserum against Rep, diluted at 1:1000. Low amounts of Rep and RepA was detected in cells bombarded with wild type virus DNA (pBY002). A similar expression pattern was observed when Rep was placed under the control of the 35S promoter (p35SRep), although levels were somewhat higher. The amount of Rep protein produced from an intronless construct (pΔintron) was higher than the amount of protein produced by a wild type construct and an even greater amount of Rep protein was produced from a construct wherein the intronless rep gene is under the control of the promoter 35S (p35SΔintron) (data not shown). These data demonstrate that the antiserum against Rep is a valuable reagent for determination of Rep expression and the relative levels of Rep and RepA in plant tissues.

Example 20
Use of BeYDV "LTR-STR-LIR" Replicons to Enhance Protein Expression in the Presence of Alcohol-inducible Expression of Rep Protein This example describes the use of a BeYDV LIR-SIR-LIR (LSL) replicon (a derivative of pBY024) to achieve amplification of the cassette only in the tissues of plants that are treated with a chemical inducer of Rep gene expression.

Figure 29:
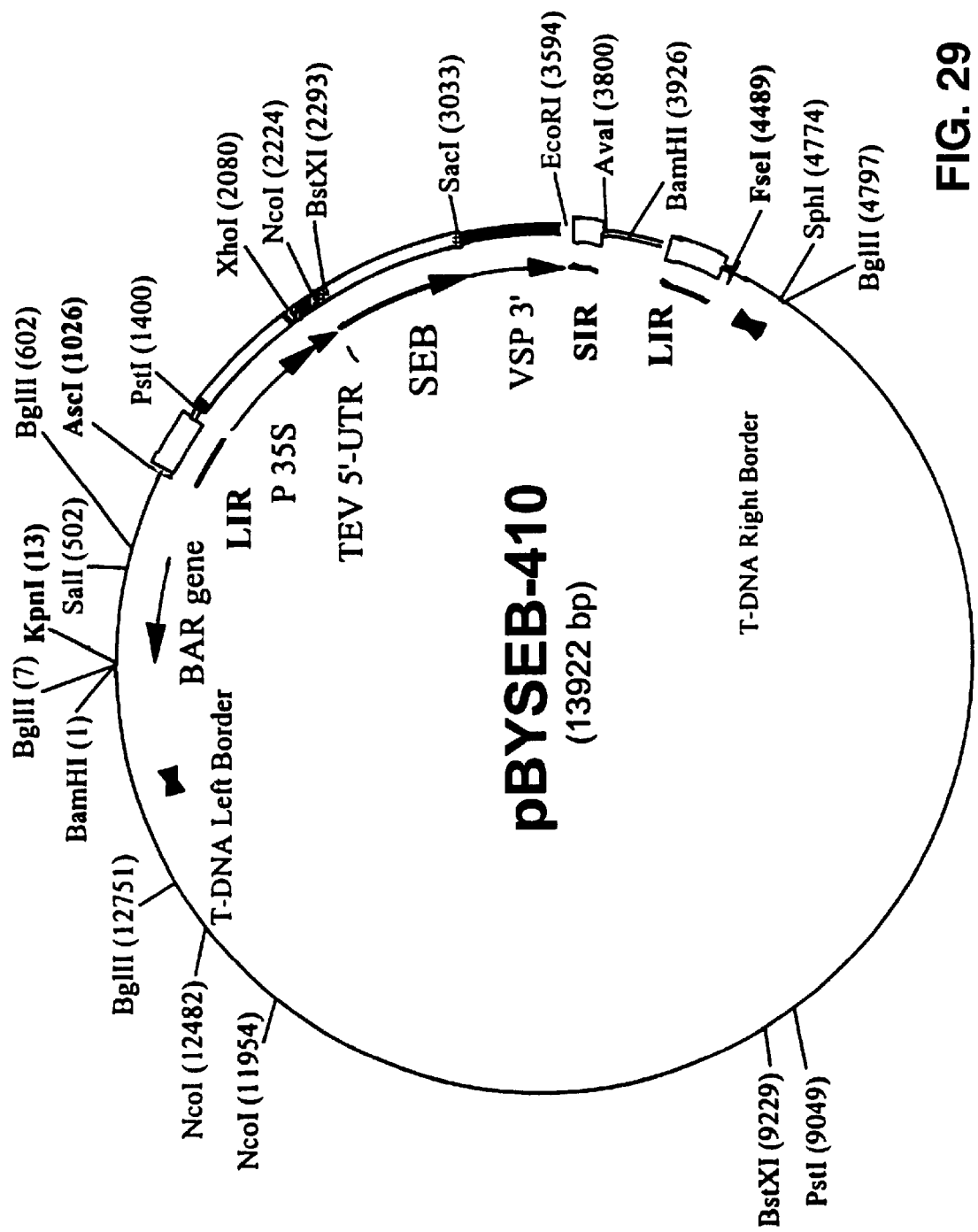
FIG. 29 is a plasmid map of pBYSEB410.
Figure 30:
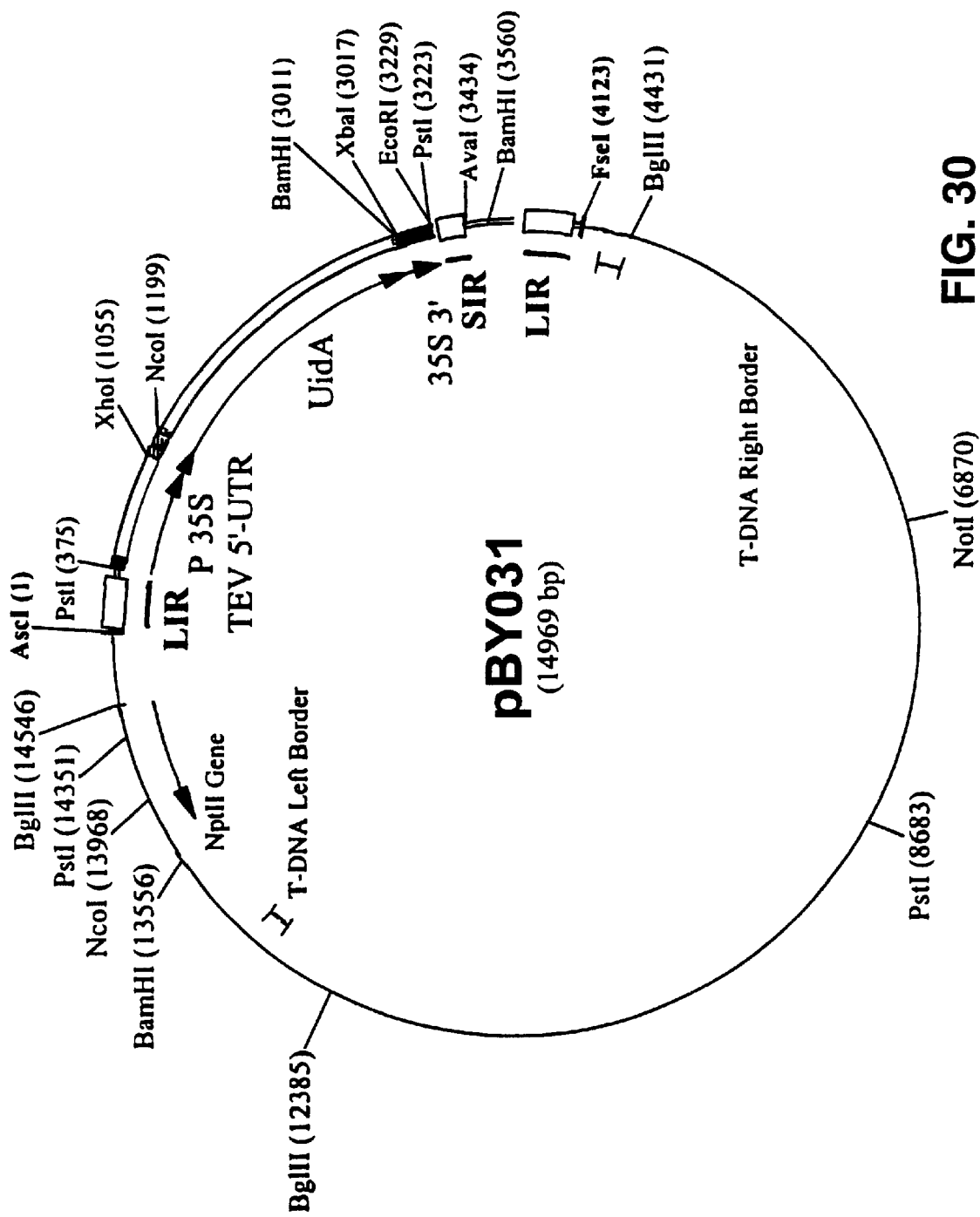
FIG. 30 is a plasmid map of pBY031.
Figure 31:
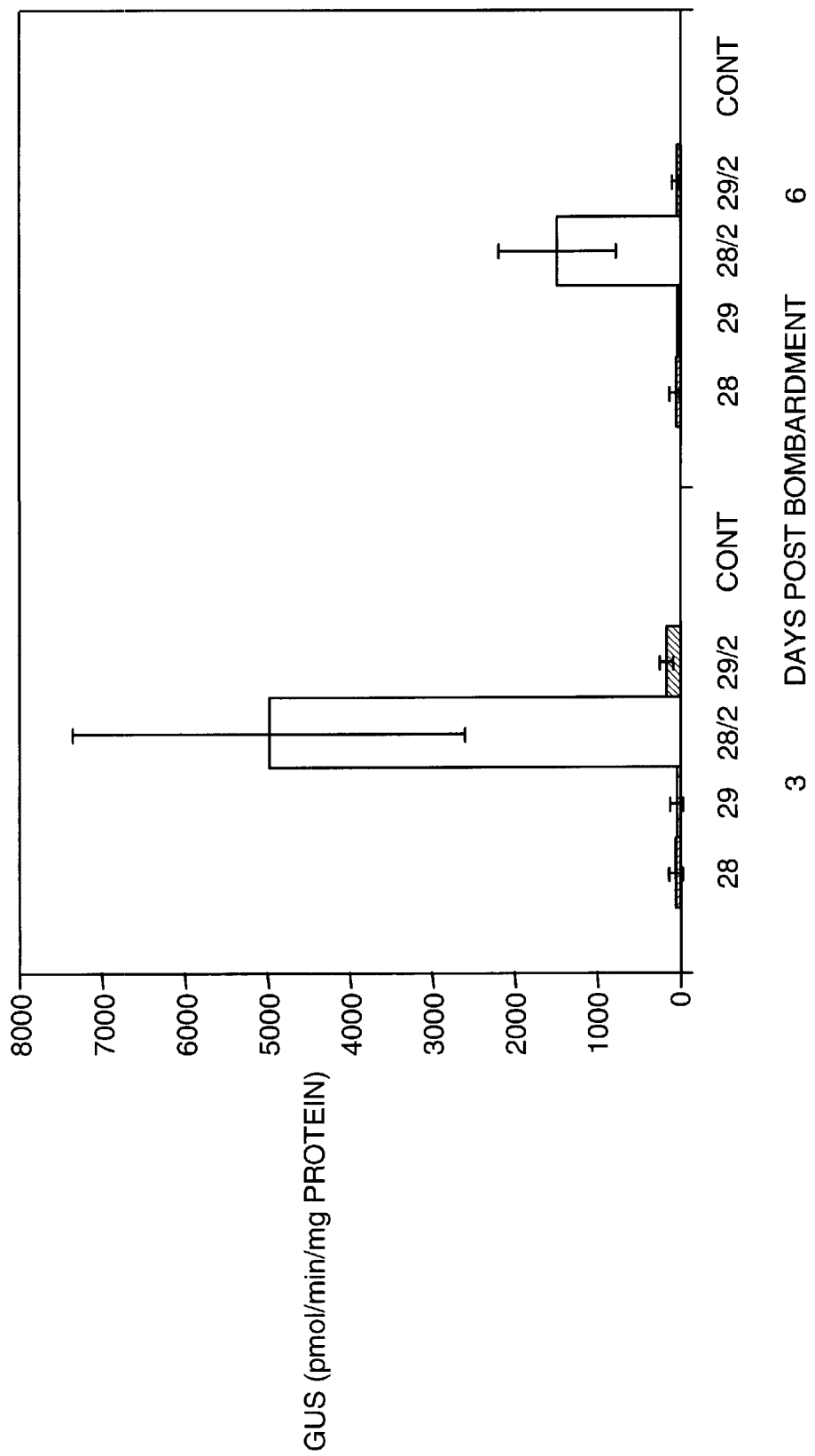
FIG. 31 is a graph illustrating enhancement of GUS expression in tobacco NT1 cells.

The binary T-DNA plasmid vector pBYSEB-410 (FIG. 29) contains an expression cassette for SEB-F44S in a replication-competent context (i.e., linked to an SIR element and flanked by both the duplicated LIR regions of BeYDV) and a (bialaphos resistance gene) BAR selection marker. Thus pBYSEB-410 is used to transform *Arabidopsis thaliana* using the method of *A. tumefaciens*-mediated DNA delivery to flowers as (described in Clough and Bent, supra).

The binary T-DNA plasmid vector pSRN-ADP(F) contains an expression cassette for Rep-Δintron (a rep gene with the intron deleted) under the control of the AlcA alcohol-inducible promoter, the alcohol-responsive AlcR gene driven by the constitutive 35S promoter, and a NptII selection marker. Thus pSRN-ADP(F) (FIG. 23) is used to transform *A. thaliana* using the method of *A. tumefaciens*-mediated DNA delivery to flowers. Transformation of flowers using both vectors can be achieved simultaneously using two *A. tumefaciens*-stains transformed with either plasmid.

Progeny seeds are gerrninated and selected on media containing 50 mg/L kanamycin and 1 mg/L phosphinothricin, in order to obtain plants that contain both the NptII and BAR selection markers. Southern blot analysis or PCR analysis with gene-specific primers is used to confirm the presence of the foreign DNA from either vector in the progeny. Plants that are demonstrated to be transgenic for both pBYSEB-410 and pSRN-ADP(F) are propagated and grown in soil. Seeds are also selected on 1 mg/L phosphinothricin alone in order to obtain control plants transgenic only for pBYSEB-410. After selection for the BAR marker, leaf explants are tested for kanamycin sensitivity to identify plants transgenic only for pBYSEB-410 and not for pSRN-ADP(F).

In order to induce the AlcA promoter controlling Rep expression, the plants are watered with a solution of 1% ethanol. Leaf tissues are sampled on successive days after ethanol induction to verify appropriate expression of Rep using Western blot and SEB expression by ELISA or Western blot. Copy number of the replicating episome is examined by Southern blot. It is expected that the SEB expression will be at least 10-fold higher in the pBYSEB-410/pSRN-ADP(F) plants than in the pBYSEB-410 plants.

Other dicotyledon plants are also co-transformed with pBYSEB-410 (or similar vectors containing alternative expression cassettes, described herein) and pSRN-ADP(F). For example, potato plants are used as hosts, and the resulting tubers of double transgenic lines are treated with ethanol to induce Rep expression and thus replication of the BeYDV LSL replicon.

Example 21

Use of BeYDV LSL Replicons to Enhance Expression in a Fruit-specific Manner

This example describes the use of a BeYDV "LSL" replicon (derivative of pBY024) to achieve amplification of the cassette only in ripening fut tissues of tomato. The binary T-DNA plasmid vector pBY031 contains a GUS expression cassette in a replication-competent context (i.e., linked to a SIR element and between the duplicated LIR regions of BeYDV). Thus pBY031 is used to transform tomato (Lycopersicon esculentum) using *A. tumefaciens*-mediated DNA delivery. Transformed plants expressing GUS in the fruit are selected by histochemical stain for GUS or by fluorometric assay for GUS (as described in Jefferson, 1987, *Plant Mol. Biol. Report,* 5:387) and seeds are obtained, washed, and dried. To measure expression of other proteins useful according to the invention to be expressed in this manner Western blot analysis or ELISA is performed with an appropriate antibody to identify the optimal transgenic lines. Transgenic lines with single-locus insertions are identified from this group of expressing lines by Southern blot of genomic DNA from leaves.

The binary T-DNA plasmid vectors pE8-Rep (FIG. 13) and pE8-Δintron (FIG. 21) each contain a fruit-ripening specific E8 promoter driving transcription of either RepC1/C2 (with intron) or Rep-Δintron (with intron deleted), and are used to transform tomato using the method of *A. tumefaciens*-mediated DNA delivery.

Transgenic plants expressing Rep in ripening fruit are identified using Western blot with the rabbit antiserum against Rep described in Example 19. Transgenic lines with single-locus insertions are identified from this group of expressing lines by Southern blot of genomic DNA from leaves. Seeds of single-locus Rep-expressing lines are obtained, washed, and dried.

The seeds of lines transgenic for pBY031, pE8-Rep, and pE8-Δintron are stored at 4° C. for one month, and then germinated and selected on medium containing 50 mg/L kanamycin. Potential homozygous lines are selected by Southern blot of genomic DNA from leaves, and candidates are grown to the stage of flowering. The flowers are self-pollinated, and seeds obtained from ripe fruit are washed and dried. After storage at 4° C. for one month, 25 seeds from candidate homozygous lines are germinated and selected on medium containing 50 mg/L kanamycin. Those lines that yield 100% kanamycin-resistant progeny are considered homozygous.

The homozygous lines are grown to the stage of flowering, and pBY031 plants are crossed with either pE8-Rep or pE8-Δintron plants. The use of pE8-Δintron is preferred, because a higher proportion of double-stranded replicating episomal DNA is expected, based on the results of Liu et al. (1998, supra). The cross is performed either by placing pollen from pBY031 plants on the stigma of Rep plants, or by placing pollen from Rep plants on the stigma of pBY031 plants. In either case, 100% of the progeny will carry a single-locus transgene from pBY031 and either pE8-Rep or pE8-Δintron. Seeds from ripe fruit are obtained, washed, and dried.

After storage at 4° C. for one month, seeds of pBY031/pE8-Rep plants are germinated and plants are grown to maturity, with either self-pollination or pollination from a non-transgenic donor. Since the maternal tissues comprise the fruit, the fruit of pBY031/pE8-Rep plants should behave similarly with regard to GUS expression regardless of the pollen donor. pBY031 plants are grown separately as baseline controls. During fruit ripening, as the color of the fruit begins to change from green to yellow, orange, and then red, the E8 promoter will become more and more active, driving transcription of the Rep gene and leading to expression of the Rep protein. Fruits are sampled at different ripening stages to verify appropriate expression of Rep using Western blot and to examine GUS expression by enzymatic assay. Copy number of the replicating episome is examined by Southern blot. It is expected that the GUS expression will be at least 10-fold higher in the pBY031/pE8-Rep fruits than in the pBY031 fruits.

An alternative to the sexual crossing strategy to obtain pBY031/pE8-Rep plants is as follows. A binary T-DNA vector that contains the cassettes for both the GUS/LSL and the E8-Rep linked between right and left T-DNA border elements is constructed. This construct is used to transform plants and examine episomal replication and enhancement of expression in the primary transformed lines.

Such a system can be used in other dicotyledon plants by regulating the expression of RepC1/C2 or Rep-Δintron with a homologous fruit ripening-specific promoter.

Example 22
Use of BeYDV "LSL" Replicons to Enhance Protein Expression in Seeds

This example describes the use of a BeYDV "LSL" replicon (derivative of pBY024) to achieve amplification of the cassette only in seeds of *Arabidopsis thaliana* plants. The binary T-DNA plasmid vector pBYSEB-410 (FIG. 29) contains an expression cassette for SEB-F44S in a replication-competent context (i.e., linked to a SIR element and between the duplicated LIR regions of BeYDV) and a BAR selection marker. The binary T-DNA plasmid vector p2S-Δintron contains an expression cassette for Rep-Δintron (with intron deleted) under the control of the *A. thaliana* 2S2 seed protein promoter and a NptII selection marker. Thus pBYSEB-410 and p2S-Δintron are used to transform *A. thaliana* using *A. tumefaciens*-mediated DNA delivery to flowers. Transformation of flowers using both vectors can be achieved simultaneously using two *A. tumefaciens*-stains transformed with either plasmid.

Progeny seeds are then germinated and selected on media containing 50 mg/L kanamycin and 1 mg/L phosphinotlricin, in order to obtain plants that carry both the NptII and BAR selection markers. Southern blot or PCR with gene-specific primers is used to confirm the presence of the foreign DNA from either vector in the progeny. Plants that are confirmed transgenic for both pBYSEB-410 and p2S-Δintron are propagated and grown in soil. Seeds are also selected on 1 mg/L phosphinoibricin alone in order to obtain control plants transgenic only for pBYSEB-410. After selection for the BAR marker, leaf explants are tested for kanamycin sensitivity to identify plants transgenic only for pBYSEB-410 and not for p2S-Δintron.

Plants are grown to maturity and during seed maturation, the seeds are extracted to verify appropriate expression of Rep using Western blot analysis and to examine SEB expression by ELISA or Western blot analysis. Copy number of the replicating episome is examined by Southern blot analysis. It is expected that the SEB expression will be at least 10-fold higher in the pBYSEB-410/p2S-Δintron plants than in the pBYSEB-410 plants.

Other dicotyledon plants are co-transformed with pBYSEB-410 (or similar vectors containing alternative expression cassettes) and p2S-Δintron. For example, soybean plants are used as hosts, and Rep expression is controlled by fusion to a glycinin seed specific promoter (Iida et al., 1995, *Plant Cell Reports,* 14: 539).

Example 23

Enhancment of Expression of GUS using a Replicating BeYDV "LSL" Cassette

This experiment demonstrates that transient expression of GUS in tobacco NT-1 cells can be enhanced greatly by inclusion of the GUS expression cassette in the "LSL" cassette exemplified in pBY024.

Mid-logarithmic NT-1 cell cultures (about $10^6$ cells/ml) were let to settle and resuspended in half of the original volume of culture medium. One ml of this suspension was plated on NT solid medium in patches of about 2.5 cm in diameter. Gold particles (1 μm, BioRad) were coated with plasmid DNA as described by Sanford et al. (Methods in Enzymol. 1993; 217, 483–509). Each plate was bombarded by gold particle particles coated with 0.25 nmol plasmid DNA (in case of co-delivery, 0.25 nmol of each of the two constructs) of either pBY028, pBY029 with or without pBY002. On days three and six after bombardment half of the cell mass from three different plate was harvested and total soluble proteins were extracted as described by Jefferson (Jefferson, Plant Mol. Biol. Report. 1987; 5:387). GUS activity was assayed according to Jefferson (supra). The results demonstrated in FIG. 31 clearly show that for pBY028+pBY002, GUS activity at 3 days after bombardment is approximately 50 to 100 times higher than for pBY028 alone. At 6 days after bombardment, the enhancement is less striking, but still 15 to 30 fold higher than for pBY028 alone. It is likely that the enhanced expression is a result of amplification of the expression cassette when pBY002 is present to provide Rep protein to mediate the excision and replication of the "LSL" replicon of pBY028. pBY029, which is similar to pBY028 but wherein the GUS expression cassette is inserted in reverse orientation within the LSL cassette, showed substantially less enhancement when co-delivered with pBY002, but still showed approximately 3-fold enhancement at day 3. It is not clear whether the lower enhancement with pBY029+pBY002 (relative to pBY028+pBY002) is a result of inpaired replication or transcription.

Example 24
Divergent PCR Confirms Replication of LSL Constructs

Figure 32A:
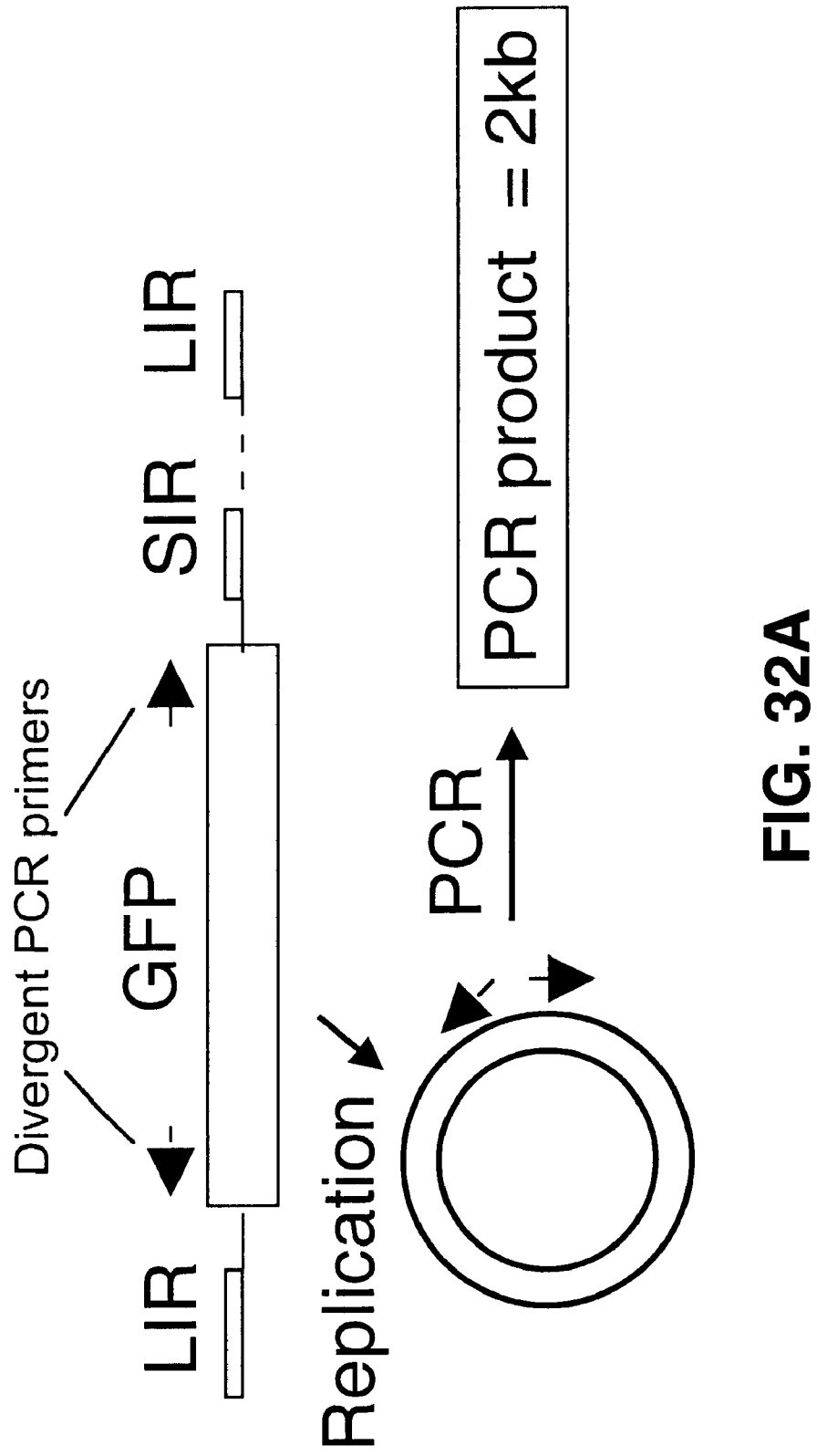
FIG. 32A illustrates the strategy for divergent PCR.
Figure 32B:
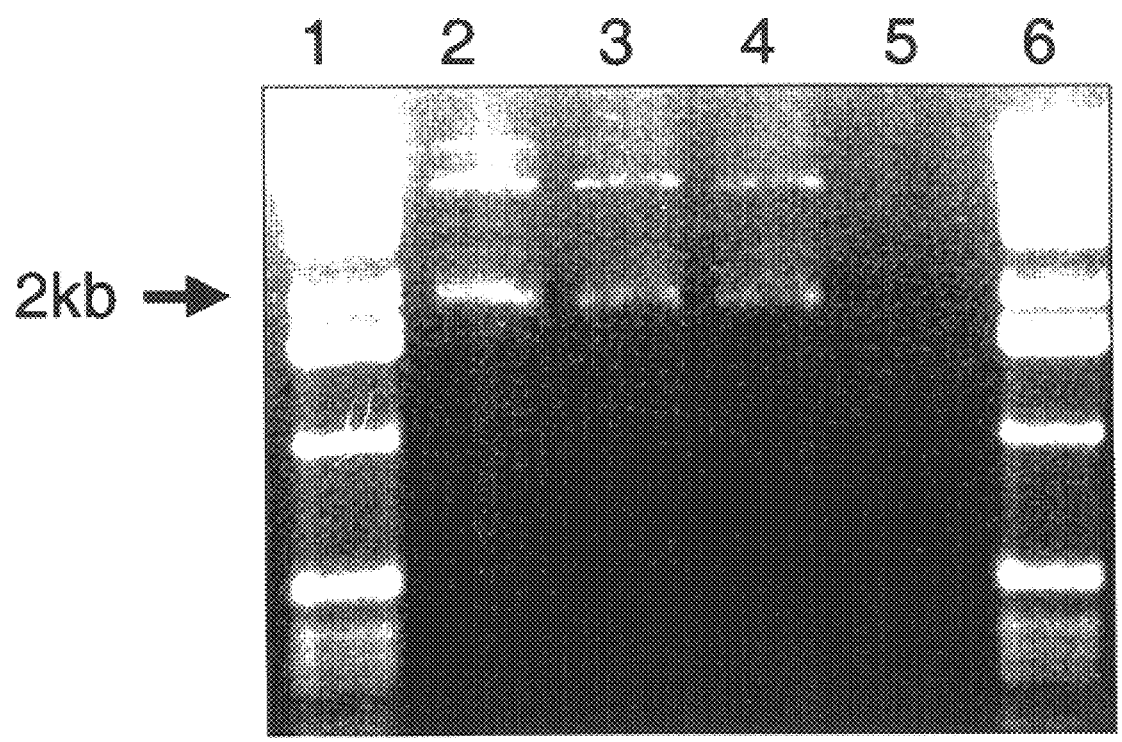
FIG. 32B is gel demonstrating PCR products of a divergent PCR reaction.

Divergent PCR is used to confirm replication of a construct according to the invention (for example LIR-GFP-SIR-LIR). Tobacco NT1 cells were bombarded with the reporter construct containing green fluorescent protein gene (GFP) inserted between LIR and SIR, with a second downstream LIR. When such constructs that contain duplicated LIR elements are present in cells with Rep protein, recombination between the LIR elements to release the intervening DNA allows replication of the episome. Thus divergent primers are used to amplify the predicted sized recombinant fragment only when replication occurs. FIG. 32 indicates that the predicted 2 kb DNA fragment is amplified by PCR in samples from cells co-bombarded with Rep-producing constructs, but not with the reporter construct alone. In FIG. 32 lane 1 is a DNA ladder, lane 2 is BeYDV (pBY002), lane 3 is p35SRep, lane 4 is p35SΔintron, lane 5 is cassette alone and lane 6 is a DNA ladder.

Example 25
SIR is Required for Episomal Replication

Figure 33:
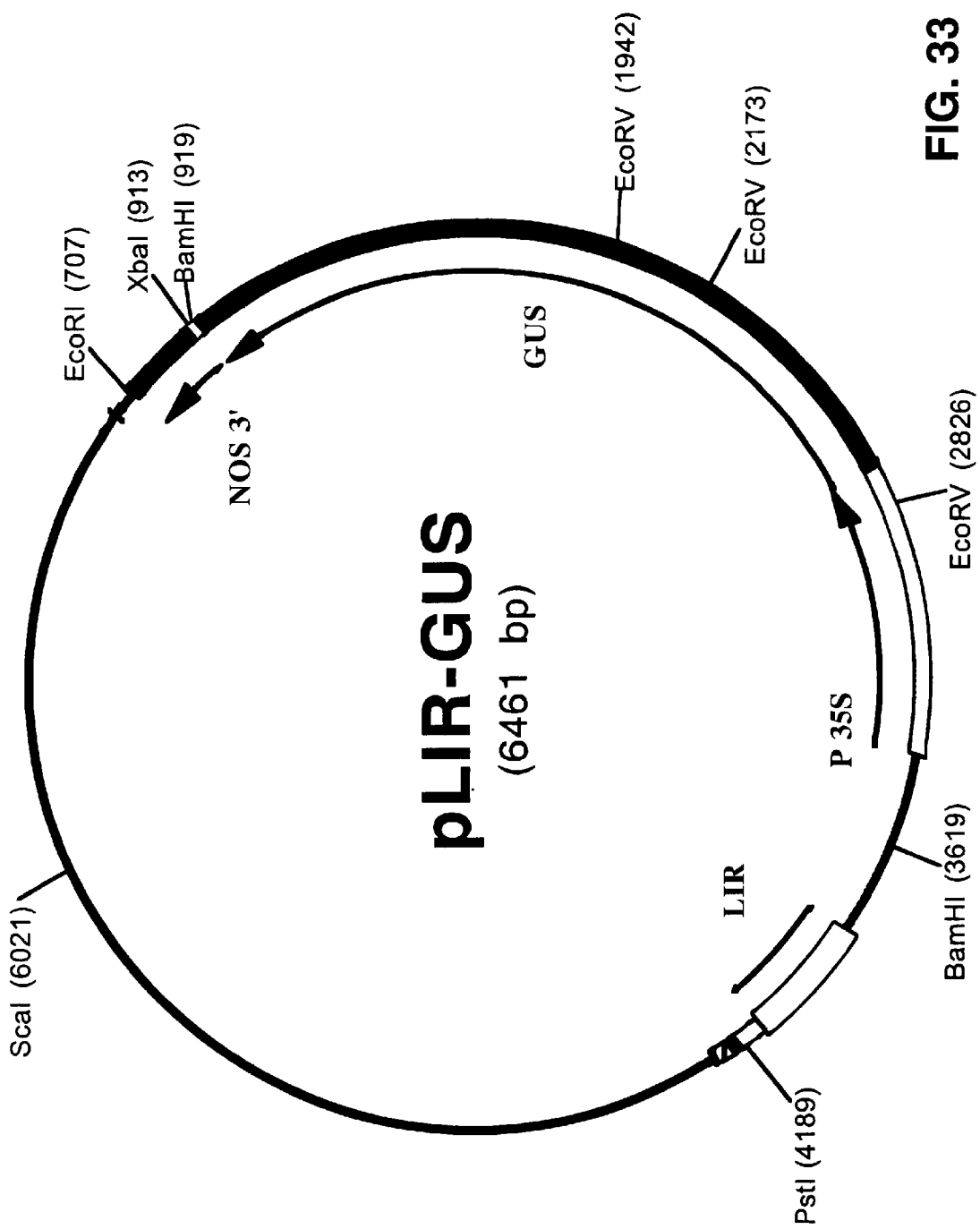
FIG. 33 is a plasmid map of pLIR-GUS.
Figure 34:
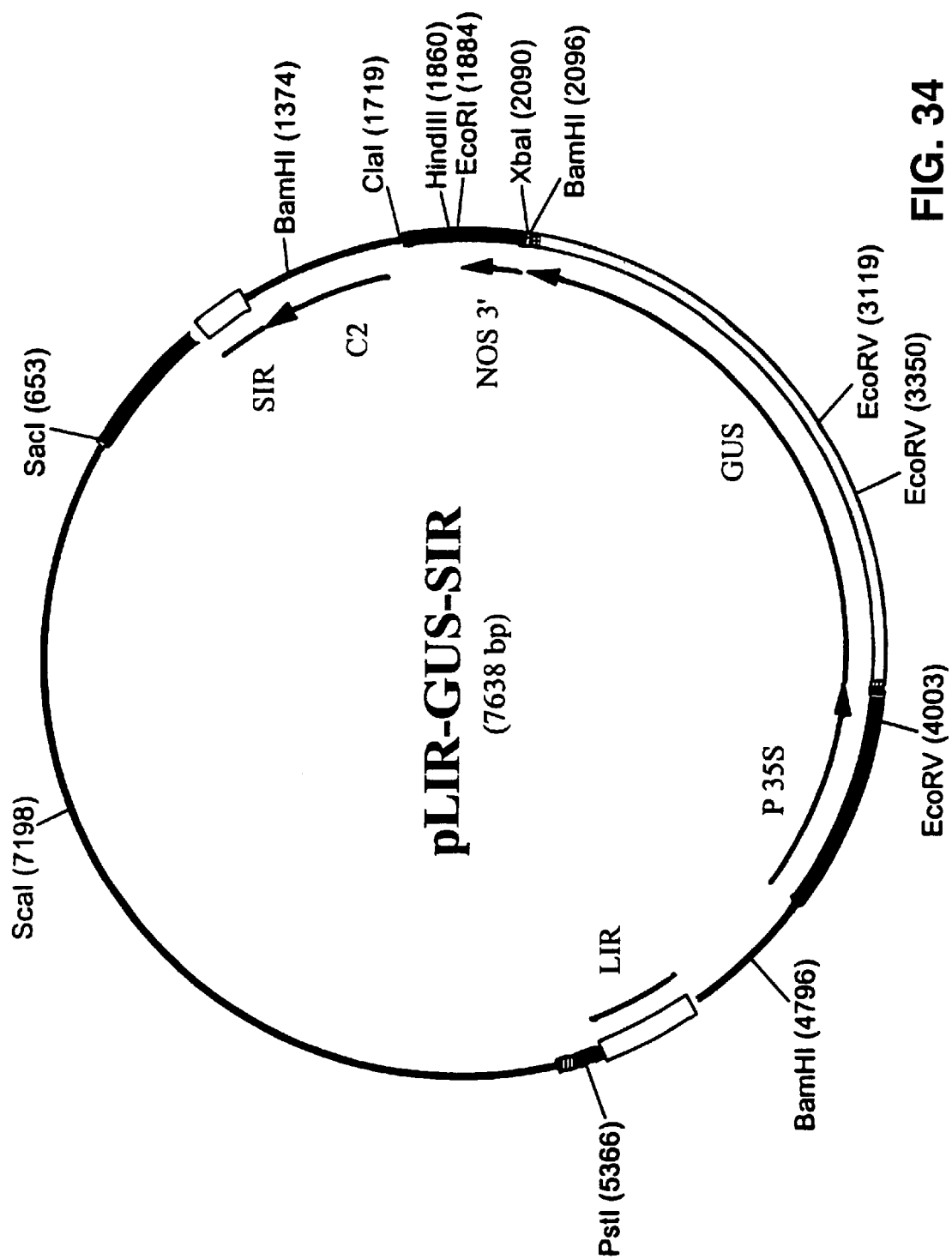
FIG. 34 is a plasmid map of pLIR-GUS-SIR

NT-1 cells were bombarded with pLIR-GUS-SIR (FIG. 33) (in the presence or absence of a Rep protein provided by pBY002) or with pLIR-GUS (FIG. 34) (in the presence or absence of a Rep protein provided by pBY002). Southern blot analysis demonstrates that the GUS containing replicon fails to replicate in the absence of an SIR element (data not shown).

Example 26
Use of a Chimeric Oligonucleotide to Induce Replication of Recombinant Genorne-integrated BeYDV Replicons This example illustrates how a novel mechanism can be used to obtain a genetic mutation in a plant that will induce replication of genome-integrated BeYDV replicons. Self-complimentary chimeric oligonucleotides (COs) composed of DNA and modified RNA residues have been used to perform gene-specific mutations in plant cells (Beetham et al., 1999, *Proc. Natl. Acad. Sci. USA*, 96:8774; and Zhu et al., 1999, *Proc. Natl. Acad. Sci. USA*, 96: 8768).

Figure 35:
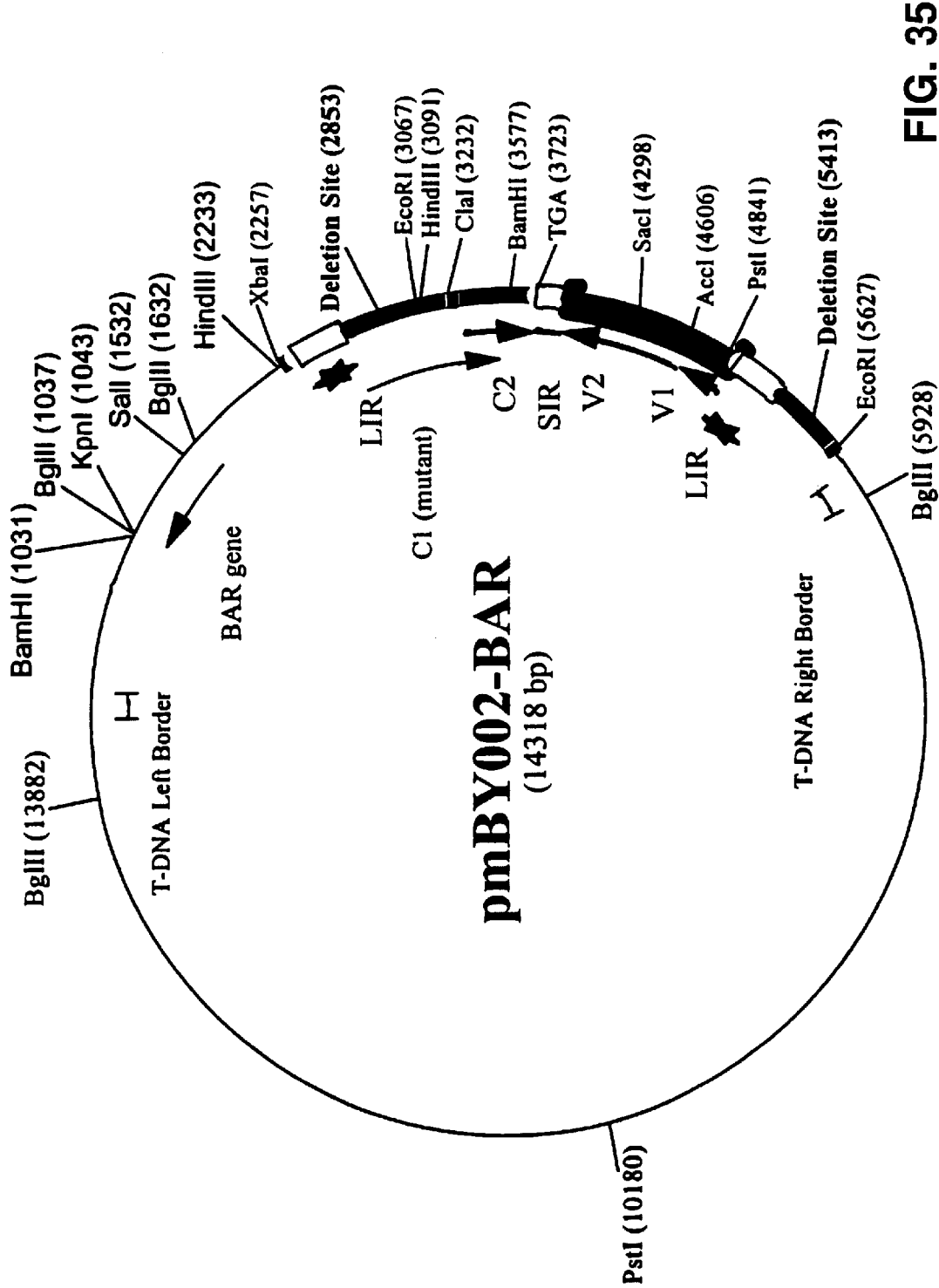
FIG. 35 is a plasmid map of pmBY002-BAR.

A mutated form of pBY002 (pmBY002) is constructed using the QuickChange (Stratagene) mutagenesis kit and the complimentary oligonucleotides:
5'-CCTTGTATTAGGGTCCTTCTTTTTTCG (SEQ ID NO:21) and
5'-CGAAAAAAGAAGGACCCTAATACAAGG (SEQ ID NO:22). This mutation causes deletion of a single "A" nucleotide within the 5' BamHI site in the C1 portion of the coding sequence of RepC1/C2, and thus a reading frameshift that prevents production of Rep. Since pBY002 contains a whole BeYDV genome and duplicated LIR elements, a reversion in the mutation described by insertion of the deleted "A" nucleotide would restore the infectivity of the mutant clone in pmBY002. The mutant BeYDV 1.4-mer is obtained by digestion of pmBY002 with XbaI and partial digestion with EcoRI, inserted into pGPTV-BAR (Becker et al., 1992, *Plant Mol. Biol.*, 20:1195) and digested with XbaI and EcoRI to form pmBY002-BAR (FIG. 35).

pmBY002-BAR is used to transform tomato (Lycopersicon esculentum) using A. tumefaciens-mediated DNA delivery. Transforned lines are selected on media containing 1 mg/L phosphinothricin, and the presence of the transgene is confimed by Southern blot using BeYDV sequence probes and PCR using BeYDV-specific primers with genomic DNA from leaves. Positive lines are grown to maturity, and seeds are obtained, washed, and dried.

pBY031 contains a GUS expression cassette in a replication-competent context (i.e., linked to a SIR element and between the duplicated LIR regions of BeYDV), and a NptII selection marker within T-DNA borders. Thus pBY031 is used to transform tomato (Lycopersicon esculentum) using *A. tumefaciens*-mediated DNA delivery. Transformed plants expressing GUS in the fruit are selected by histochemical stain for GUS or by fluorometric assay for GUS (Jefferson, 1987, *Plant Mol. Biol. Report*, 5:387) and seeds are obtained, washed, and dried.

The seeds of lines transgenic for pBY031, and pmBY002-BAR are stored at 4° C. for one month, and then germinated and selected on medium containing either 50 mg/L kanamycin (pBY031) or 1 mg/L phosphinothricin (pmBY002-BAR). Potential homozygous lines are selected by Southern blot of genomic DNA from leaves, and candidates are grown to the stage of flowering. The flowers are self-pollinated, and seeds obtained from ripe fruit are washed and dried. After storage at 4° C. for one month, 25 seeds from candidate homozygous lines are germinated and selected on medium containing 50 mg/L kanamycin (pBY031) or 1 mg/L phosphinothricin (pmBY002-BAR). Those lines that yield 100% resistant progeny are considered homozygous.

The homozygous lines are grown to the stage of flowering, and pBY031 plants are crossed with pmBY002-BAR plants. The cross is performed either by placing pollen from pBY031 plants on the stigma of pmBY002-BAR plants, or by placing pollen from pmBY002-BAR plants on the stigma of pBY031 plants. In either case, 100% of the progeny should carry a single-locus transgene from pBY031 and pmBY002-BAR. Seeds from ripe fruit are obtained, washed, and dried. After storage at 4° C. for one month, seeds of pBY031/pmBY002-BAR plants are germinated and plants are grown in soil.

A chimeric oligonucleotide (CO) designed to insert the deleted "A" nucleotide into the mutated C1 sequence in pmBY002-BAR is created as described (Beetham et al., supra). The CO is delivered into leaves of either pBY031 or pBY031/pmBY002-BAR plants by microprojectile bombardment as described (Beetham et al., supra). The mutation allows the BeYDV replicon to become active by acquisition of the capacity to produce an active Rep protein. The Rep protein present in cells harboring the virus mediates the excision and replication of the GUS replicon in the transgene delivered by pBY031. The virus moves systemically throughout the plant, producing Rep and replicating itself and the GUS replicon in the process.

Leaves are sampled at different times after delivery of the CO to verify appropriate expression of Rep by Western blot and GUS expression by enzymatic assay. The copy number of the replicating episome is determined by Southern blot. It is expected that the GUS expression will be at least 10-fold higher in the pBY031/pmBY002-BAR plants than in the pBY031 plants.

REFERENCES

The pertinent portions of the following references are incorporated herein by reference.

Arntzen et al. (1997) "Oral vaccine production in the edible tissues of transgenic plants." In: *New Generation Vaccines,* Second Edition (Eds. Levine M M, Woodrow G C, Kaper J B, Cobon G S) Marcel Dekker, New York, pp 263–277.

Carrington et al. (1990) "Cap-independent enhancement of translation by a plant potyvirus 5' nontranslated region," *J. Virol.* 64:1590–1597.

Christou et al. (1990) "Soybean genetic engineering—commercial production of transgenic plants," *Trends Biotechnol.* 8:145–151.

Clements et al. (1988) "Adjuvant activity of *Escherichia coli* heat-labile enterotoxin and effect on the induction of oral tolerance in mice to unrelated protein antigens," *Vaccine* 6:269–277.

Cregg et al. (1987) "High level expression and efficient assembly of hepatitis B surface antigenin the methulotrophic yeast *Pichia pastoris,*" *Bio/Technology* 5:479–485.

Di Tommaso et al. (1996) "Induction of antigen-specific antibodies in vaginal secretions by using a nontoxic mutant of heat-labile enterotoxin as a mucosal adjuvant," *Infect. Immun.* 64:974–979.

Doyle et al. (1986) "The glycosylated seed storage proteins of *Glycine max* and *Phaseolus vulgaris*. Structural homologies of genes and proteins," *J. Biol. Chem.* 261:9228–9238.

Giovannoni, et al. (1989) "Expression of a chimeric polygalacturonase gene in transgenic rin (ripening inhibitor) tomato fruit results in polyuronide degradation but not fruit softening," *Plant Cell* 1, 53–63.

Goddijn et al. (1995) "Plants as bioreactors," *Trends Biotechnol.* 13:379–387.

Hanley-Bowdoin et al. (1988) "Transient expression of heterologous RNAs using tomato golden mosaic virus," *Nucl. Acids Res.* 16: 10511.

Hanley-Bowdoin et al. (1990) "Expression of functional replication protein from tomato golden mosaic virus in transgenic tobacco plants," *Proc. Natl. Acad. Sci. USA* 87: 1446–1450.

Haq et al. (1995) "Oral immunization with a recombinant bacterial antigen produced in transgenic plants," *Science* 268:714–716.

Hayes et al. (1988) "Gene amplification and expression in plants," *Nature* 334: 179–182.

Hayes et al. (1989) "Stability and expression of bacterial genes in replicating geminivirus ectors in plants," *Nucl. Acids Res.* 17: 2391–2403.

Hiatt et al. (1989) "Production of antibodies in transgenic plants," *Nature* 342:76–78.

Hood et al. (1997) "Commercial production of avidin from transgenic maize: haracterization of transformant, production, processing, extraction and purification," *Molecular Breeding* 3:291–306.

Iida et al. (1995) "Positive and negative cis-regulatory regions in the soybean glycinin promoter identified by quantitative transient gene expression," *Plant Cell Reports* 14: 539–544.

Jefferson et al. (1987) "GUS fusions: β-glucuronidase as a sensitive and versatile gene fusion marker in higher plants," *EMBO J.* 13:3901–3907.

Jiang et al. (1992) "Expression, self-assembly, and antigenicity of the Norwalk virus capsid protein," *J. Virol.* 66:6527–6532.

Kanevski et al. (1992) "Tobacco lines with high copy numbers of replicating recombinant geminivirus vectors after biolistic delivery," *Plant J.* 2: 457–463.

Kuntz et al. (1997) "Polymeric controlled delivery for immunization," *Trends Biotechnol.* 15:364–369.

Kusnadi et al. (1997) "Production of recombinant proteins in transgenic plants: practical considerations," *Biotechnol. Bioeng.* 56: 473–484.

Liu et al. (1997) "Molecular characterization of a Subgroup I geminivirus from a legume in South Africa," *J. Gen. Virol.,* 78: 2113–2117.

Ma et al. (1995a) "Generation and assembly of secretory antibodies in plants," *Science* 268: 716–719.

Ma et al. (1995b) "Plant antibodies for immunotherapy," *Plant Physiol.* 109:341–346.

Maniatis et al. (1982) *Molecular Cloning: A Laboratory Manual.* Cold Spring Harbor Laboratory, 1982.

Mason et al. (1988) "Proteins homologous to leaf storage proteins are abundant in stems of soybean seedlings. Analysis of proteins and cDNAs," *Plant Mol. Biol.* 11;845–856.

Mason et al. (1992) "Expression of hepatitis B surface antigen in transgenic plants," *Proc. Natl. Acad. Sci. USA* 89:11745–11749.

Mason et al. (1995) "Transgenic plants as vaccine production systems," *Trends Biotechnol.* 13:388–392.

Mason et al. (1996) "Expression of Norwalk virus capsid protein in transgenic tobacco and potato and its oral immunogenicity in mice," *Proc. Natl. Acad. Sci. USA* 93:5335–5340.

Mason et al. (1998) "Edible vaccine protects mice against *E. coli* heat-labile enterotoxin (LT): potatoes expressing a synthetic LT-B gene," *Vaccine,* 16:1336–1343.

McElroy et al. (1994) "Foreign gene expression in transgenic cereals," *Trends Biotechnol.* 12:62–68.

Palmer K. (1997) "Investigations into the use of maize streak virus as a gene vector" PhD Thesis, University of Cape Town, South Africa.

Palmer K. (1997a) "The use of geminiviruses in biotechnology and plant molecular biology, with particular focus on Mastreviruses," *Plant Science* 129:115–130.

Palmer et al. (1 997b) "Molecular biology of Mastreviruses". *Advances in Virus Research* 50: 183–234.

Palmer et al. (1997c) "Geminivirus isolation and DNA extraction". In: *Plant Virology Protocols* (Series: Methods in Molecular Biology). (S. Taylor and G. Foster (Eds)) Totowa, N.J.: Humana Press.

Palmer et al. (1997d) "Generation of transgenic maize lines with autonomously replicating MSV gene vectors," *Plant Molecular Biology,.*

Penarrubia et al. (1992), *Bio/Technology* 10:561–564.

Shah et al. (1995) "Resistance to diseases and insects in transgenic plants: progress and applications to agriculture," *Trends Biotechnol.* 13:362–368.

Sijmons et al. (1990) "Production of correctly processed human serum albumin in transgenic plants," *Bio/Technology* 8:217–220.

Stanley et al. (1990) "Defective viral DNA ameliorates symptoms of geminivirus infection in transgenic plants," *Proc. Natl. Acad. Sci. USA* 87: 6291–6295.

Stenger et al. (1991) "Replicational release of geminivirus genomes from tandemly repeated copies: evidence for rolling-circle replication of a plant viral DNA," *Proc. Natl. Acad. Sci. USA* 88:8029–8033.

Stewart et al. (1996) "Genetic transformation, recovery, and characterization of fertile soybean transgenic for a synthetic *Bacillus thuringiensis* cryIAc gene," *Plant Physiol.* 112: 121–129.

Sugrue et al. (1997) "Expression of the dengue virus structural proteins in *Pichia pastoris* leads to the generation of virus-like particles," *J. Gen. Virol.* 78:1861–1866.

Thanavala et al. (1995) "Immunogencity of transgenic plant-derived hepatitis B surface antigen,"*Proc. Natl. Acad. Sci. USA* 92: 3358–3361.

Timmermans et al. (1994) "Geminiviruses and their uses as extrachromosomal replicons," *Annu. Rev. Plant Physiol. Plant Mol. Biol.* 45: 79–112.

Vitale et al. (1984) "Biosynthesis and processing of phytohemagglutinin in developing bean cotyledons," *Eur. J. Biochem.* 141:97–104.

Xi et al. (1990) "Norwalk virus genome cloning and characterization," *Science,* 250:1580–1583.

Zambryski P. (1988) "Basic processes underlying Agrobacterium-mediated DNA transfer to plant cells," *Annu. Rev. Genet.* 22:1–30.

---

SEQUENCE LISTING

<160> NUMBER OF SEQ ID NOS: 22

<210> SEQ ID NO 1
<211> LENGTH: 303
<212> TYPE: DNA
<213> ORGANISM: bean yellow dwarf virus

<400> SEQUENCE: 1

```
aggcatgttg ttgtgactcc gaggggttgc ctcaaactct atcttataac cggcgtggag     60
gcatggaggc aagggcattt tggtaattta agtagttagt ggaaaatgac gtcatttact    120
taaagacgaa gtcttgcgac aagggggggcc cacgccgaat tttaatatta ccggcgtggc    180
cccaccttat cgcgagtgct ttagcacgag cggtccagat ttaaagtaga aaagttcccg    240
cccactaggg ttaaaggtgt tcacactata aaagcatata cgatgtgatg gtatttgatg    300
gag                                                                  303
```

<210> SEQ ID NO 2
<211> LENGTH: 1110
<212> TYPE: DNA
<213> ORGANISM: bean yellow dwarf virus

<400> SEQUENCE: 2

```
ccatgggacc ttctgctagc aagaacttca gactccaatc taaatatgtt ttccttacct     60
accccaagtg ctcatctcaa agagatgatt tattccagtt tctctgggag aaactcacac    120
cttttcttat tttcttcctt ggtgttgctt ctgagcttca tcaagatggc actacccact    180
atcatgctct tatccagctt gataaaaaac cttgtattag ggatccttct tttttcgatt    240
ttgaaggaaa tcaccctaat atccagccag ctagaaactc taaacaagtc cttgattaca    300
tatcaaagga cggagatatt aaaaccagag gagatttccg agatcataag gtctctcctc    360
gcaaatctga cgcacgatgg cgaactatta tccagactgc aacgtctaag gaggagtatc    420
ttgacatgat caaagaagaa ttccctcatg aatgggcaac aaagcttcaa tggctggaat    480
attcagccaa caaattattt cctccacaac ctgagcagta cgtgtcgccc ttcacagaat    540
cagatctccg ctgccacgaa gatctgcaca actggagaga gacgcaccta tatcatgtaa    600
gcatcgatgc ctacactttc atacatcctg tctcctacga tcaagcacaa tctgaccttg    660
agtggatggc cgatctaacc aggatgaggg aaggactggg gtcagacacc ccagcctcta    720
catctgcgga ccaactcgta ccggaaagac cacctgggct agaagtctcg ggcgacacaa    780
ctactggaac gggaccatcg acttcaccaa ctacgatgaa cacgccacct ataatatcat    840
cgacgacatc cccttcaagt tcgtcccatt gtggaagcaa ttaataggtt gccagtctga    900
tttcactgtc aaccctaaat atggaaaaaa gaagaaaata aaaggtggga tcccttctat    960
```

-continued

```
aattctttgg aatcctgacg aagactggat gttatcaatg acaagtcaac agaaggatta   1020
ctttgaagat aattgcgtca cccactatat gtgtgacggg gagacttttt ttgctcggga   1080
atcgtcgagt cactgaacgt gcctgagctc                                    1110

<210> SEQ ID NO 3
<211> LENGTH: 293
<212> TYPE: PRT
<213> ORGANISM: bean yellow dwarf virus

<400> SEQUENCE: 3

Met Gly Pro Ser Ala Ser Lys Asn Phe Arg Leu Gln Ser Lys Tyr Val
  1               5                  10                  15

Phe Leu Thr Tyr Pro Lys Cys Ser Ser Gln Arg Asp Asp Leu Phe Gln
             20                  25                  30

Phe Leu Trp Glu Lys Leu Thr Pro Phe Leu Ile Phe Phe Leu Gly Val
         35                  40                  45

Ala Ser Glu Leu His Gln Asp Gly Thr Thr His Tyr His Ala Leu Ile
     50                  55                  60

Gln Leu Asp Lys Lys Pro Cys Ile Arg Asp Pro Ser Phe Phe Asp Phe
 65                  70                  75                  80

Glu Gly Asn His Pro Asn Ile Gln Pro Ala Arg Asn Ser Lys Gln Val
                 85                  90                  95

Leu Asp Tyr Ile Ser Lys Asp Gly Asp Ile Lys Thr Arg Gly Asp Phe
            100                 105                 110

Arg Asp His Lys Val Ser Pro Arg Lys Ser Asp Ala Arg Trp Arg Thr
        115                 120                 125

Ile Ile Gln Thr Ala Thr Ser Lys Glu Glu Tyr Leu Asp Met Ile Lys
    130                 135                 140

Glu Glu Phe Pro His Glu Trp Ala Thr Lys Leu Gln Trp Leu Glu Tyr
145                 150                 155                 160

Ser Ala Asn Lys Leu Phe Pro Pro Gln Pro Glu Gln Tyr Val Ser Pro
                165                 170                 175

Phe Thr Glu Ser Asp Leu Arg Cys His Glu Asp Leu His Asn Trp Arg
            180                 185                 190

Glu Thr His Leu Tyr His Val Ser Ile Asp Ala Tyr Thr Phe Ile His
        195                 200                 205

Pro Val Ser Tyr Asp Gln Ala Gln Ser Asp Leu Glu Trp Met Ala Asp
    210                 215                 220

Leu Thr Arg Met Arg Glu Gly Leu Gly Ser Asp Thr Pro Ala Ser Thr
225                 230                 235                 240

Ser Ala Asp Gln Leu Val Pro Glu Arg Pro Pro Gly Leu Glu Val Ser
                245                 250                 255

Gly Asp Thr Thr Thr Gly Thr Gly Pro Ser Thr Ser Pro Thr Thr Met
            260                 265                 270

Asn Thr Pro Pro Ile Ile Ser Ser Thr Thr Ser Pro Ser Ser Ser Ser
        275                 280                 285

His Cys Gly Ser Asn
    290

<210> SEQ ID NO 4
<211> LENGTH: 143
<212> TYPE: PRT
<213> ORGANISM: bean yellow dwarf virus

<400> SEQUENCE: 4
```

-continued

```
Asp Gly Arg Ser Asn Gln Asp Glu Gly Arg Thr Gly Val Arg His Pro
 1               5                  10                  15

Ser Leu Tyr Ile Cys Gly Pro Thr Arg Thr Gly Lys Thr Thr Trp Ala
             20                  25                  30

Arg Ser Leu Gly Arg His Asn Tyr Trp Asn Gly Thr Ile Asp Phe Thr
         35                  40                  45

Asn Tyr Asp Glu His Ala Thr Tyr Asn Ile Ile Asp Asp Ile Pro Phe
     50                  55                  60

Lys Phe Val Pro Leu Trp Lys Gln Leu Ile Gly Cys Gln Ser Asp Phe
 65                  70                  75                  80

Thr Val Asn Pro Lys Tyr Gly Lys Lys Lys Ile Lys Gly Gly Ile
                 85                  90                  95

Pro Ser Ile Ile Leu Trp Asn Pro Asp Glu Asp Trp Met Leu Ser Met
             100                 105                 110

Thr Ser Gln Gln Lys Asp Tyr Phe Glu Asp Asn Cys Val Thr His Tyr
         115                 120                 125

Met Cys Asp Gly Glu Thr Phe Phe Ala Arg Glu Ser Ser His
     130                 135                 140
```

<210> SEQ ID NO 5
<211> LENGTH: 1024
<212> TYPE: DNA
<213> ORGANISM: bean yellow dwarf virus
<220> FEATURE:
<221> NAME/KEY: CDS
<222> LOCATION: (3)..(1010)

<400> SEQUENCE: 5

```
cc atg gga cct tct gct agc aag aac ttc aga ctc caa tct aaa tat      47
   Met Gly Pro Ser Ala Ser Lys Asn Phe Arg Leu Gln Ser Lys Tyr
    1               5                  10                  15 gtt ttc ctt acc tac ccc aag tgc tca tct caa aga gat gat tta ttc     95
Val Phe Leu Thr Tyr Pro Lys Cys Ser Ser Gln Arg Asp Asp Leu Phe
             20                  25                  30 cag ttt ctc tgg gag aaa ctc aca cct ttt ctt att ttc ttc ctt ggt    143
Gln Phe Leu Trp Glu Lys Leu Thr Pro Phe Leu Ile Phe Phe Leu Gly
         35                  40                  45 gtt gct tct gag ctt cat caa gat ggc act acc cac tat cat gct ctt    191
Val Ala Ser Glu Leu His Gln Asp Gly Thr Thr His Tyr His Ala Leu
     50                  55                  60 atc cag ctt gat aaa aaa cct tgt att agg gat cct tct ttt ttc gat    239
Ile Gln Leu Asp Lys Lys Pro Cys Ile Arg Asp Pro Ser Phe Phe Asp
 65                  70                  75 ttt gaa gga aat cac cct aat atc cag cca gct aga aac tct aaa caa    287
Phe Glu Gly Asn His Pro Asn Ile Gln Pro Ala Arg Asn Ser Lys Gln
 80                  85                  90                  95 gtc ctt gat tac ata tca aag gac gga gat att aaa acc aga gga gat    335
Val Leu Asp Tyr Ile Ser Lys Asp Gly Asp Ile Lys Thr Arg Gly Asp
             100                 105                 110 ttc cga gat cat aag gtc tct cct cgc aaa tct gac gca cga tgg cga    383
Phe Arg Asp His Lys Val Ser Pro Arg Lys Ser Asp Ala Arg Trp Arg
         115                 120                 125 act att atc cag act gca acg tct aag gag gag tat ctt gac atg atc    431
Thr Ile Ile Gln Thr Ala Thr Ser Lys Glu Glu Tyr Leu Asp Met Ile
     130                 135                 140 aaa gaa gaa ttc cct cat gaa tgg gca aca aag ctt caa tgg ctg gaa    479
Lys Glu Glu Phe Pro His Glu Trp Ala Thr Lys Leu Gln Trp Leu Glu
 145                 150                 155 tat tca gcc aac aaa tta ttt cct cca caa cct gag cag tac gtg tcg   527
```

```
Tyr Ser Ala Asn Lys Leu Phe Pro Pro Gln Pro Glu Gln Tyr Val Ser
160                 165                 170                 175 ccc ttc aca gaa tca gat ctc cgc tgc cac gaa gat ctg cac aac tgg      575
Pro Phe Thr Glu Ser Asp Leu Arg Cys His Glu Asp Leu His Asn Trp
                180                 185                 190 aga gag acg cac cta tat cat gat gag gga agg act ggg gtc aga cac      623
Arg Glu Thr His Leu Tyr His Asp Glu Gly Arg Thr Gly Val Arg His
            195                 200                 205 ccc agc ctc tac atc tgc gga cca act cgt acc gga aag acc acc tgg      671
Pro Ser Leu Tyr Ile Cys Gly Pro Thr Arg Thr Gly Lys Thr Thr Trp
        210                 215                 220 gct aga agt ctc ggg cga cac aac tac tgg aac ggg acc atc gac ttc      719
Ala Arg Ser Leu Gly Arg His Asn Tyr Trp Asn Gly Thr Ile Asp Phe
    225                 230                 235 acc aac tac gat gaa cac gcc acc tat aat atc atc gac gac atc ccc      767
Thr Asn Tyr Asp Glu His Ala Thr Tyr Asn Ile Ile Asp Asp Ile Pro
240                 245                 250                 255 ttc aag ttc gtc cca ttg tgg aag caa tta ata ggt tgc cag tct gat      815
Phe Lys Phe Val Pro Leu Trp Lys Gln Leu Ile Gly Cys Gln Ser Asp
                260                 265                 270 ttc act gtc aac cct aaa tat gga aaa aag aag aaa ata aaa ggt ggg      863
Phe Thr Val Asn Pro Lys Tyr Gly Lys Lys Lys Ile Lys Gly Gly
                275                 280                 285 atc cct tct ata att ctt tgg aat cct gac gaa gac tgg atg tta tca      911
Ile Pro Ser Ile Ile Leu Trp Asn Pro Asp Glu Asp Trp Met Leu Ser
        290                 295                 300 atg aca agt caa cag aag gat tac ttt gaa gat aat tgc gtc acc cac      959
Met Thr Ser Gln Gln Lys Asp Tyr Phe Glu Asp Asn Cys Val Thr His
    305                 310                 315 tat atg tgt gac ggg gag act ttt ttt gct cgg gaa tcg tcg agt cac     1007
Tyr Met Cys Asp Gly Glu Thr Phe Phe Ala Arg Glu Ser Ser Ser His
320                 325                 330                 335 tga acgtgcctga gctc                                                 1024

<210> SEQ ID NO 6
<211> LENGTH: 335
<212> TYPE: PRT
<213> ORGANISM: bean yellow dwarf virus

<400> SEQUENCE: 6

Met Gly Pro Ser Ala Ser Lys Asn Phe Arg Leu Gln Ser Lys Tyr Val
  1               5                  10                  15

Phe Leu Thr Tyr Pro Lys Cys Ser Ser Gln Arg Asp Asp Leu Phe Gln
                 20                  25                  30

Phe Leu Trp Glu Lys Leu Thr Pro Phe Leu Ile Phe Phe Leu Gly Val
             35                  40                  45

Ala Ser Glu Leu His Gln Asp Gly Thr Thr His Tyr His Ala Leu Ile
         50                  55                  60

Gln Leu Asp Lys Lys Pro Cys Ile Arg Asp Pro Ser Phe Phe Asp Phe
 65                  70                  75                  80

Glu Gly Asn His Pro Asn Ile Gln Pro Ala Arg Asn Ser Lys Gln Val
                 85                  90                  95

Leu Asp Tyr Ile Ser Lys Asp Gly Asp Ile Lys Thr Arg Gly Asp Phe
            100                 105                 110

Arg Asp His Lys Val Ser Pro Arg Lys Ser Asp Ala Arg Trp Arg Thr
        115                 120                 125

Ile Ile Gln Thr Ala Thr Ser Lys Glu Glu Tyr Leu Asp Met Ile Lys
    130                 135                 140
```

```
Glu Glu Phe Pro His Glu Trp Ala Thr Lys Leu Gln Trp Leu Glu Tyr
145                 150                 155                 160

Ser Ala Asn Lys Leu Phe Pro Pro Gln Pro Glu Gln Tyr Val Ser Pro
            165                 170                 175

Phe Thr Glu Ser Asp Leu Arg Cys His Glu Asp Leu His Asn Trp Arg
        180                 185                 190

Glu Thr His Leu Tyr His Asp Glu Gly Arg Thr Gly Val Arg His Pro
    195                 200                 205

Ser Leu Tyr Ile Cys Gly Pro Thr Arg Thr Gly Lys Thr Thr Trp Ala
    210                 215                 220

Arg Ser Leu Gly Arg His Asn Tyr Trp Asn Gly Thr Ile Asp Phe Thr
225                 230                 235                 240

Asn Tyr Asp Glu His Ala Thr Tyr Asn Ile Ile Asp Asp Ile Pro Phe
                245                 250                 255

Lys Phe Val Pro Leu Trp Lys Gln Leu Ile Gly Cys Gln Ser Asp Phe
                260                 265                 270

Thr Val Asn Pro Lys Tyr Gly Lys Lys Lys Ile Lys Gly Gly Ile
            275                 280                 285

Pro Ser Ile Ile Leu Trp Asn Pro Asp Glu Asp Trp Met Leu Ser Met
290                 295                 300

Thr Ser Gln Gln Lys Asp Tyr Phe Glu Asp Asn Cys Val Thr His Tyr
305                 310                 315                 320

Met Cys Asp Gly Glu Thr Phe Phe Ala Arg Glu Ser Ser His
                325                 330                 335

<210> SEQ ID NO 7
<211> LENGTH: 815
<212> TYPE: DNA
<213> ORGANISM: bean yellow dwarf virus
<220> FEATURE:
<221> NAME/KEY: CDS
<222> LOCATION: (3)..(803)

<400> SEQUENCE: 7 cc atg gac aag agg ctc ttc atc tcc cat gtg atc ctc atc ttt gca        47
   Met Asp Lys Arg Leu Phe Ile Ser His Val Ile Leu Ile Phe Ala
   1               5                   10                  15 ctc atc ttg gtg atc tct acc ccc aat gtg ttg gca gag agc caa cca       95
Leu Ile Leu Val Ile Ser Thr Pro Asn Val Leu Ala Glu Ser Gln Pro
            20                  25                  30 gac cct aag cca gat gag ttg cat aag agc agc aag ttc act ggt ctc      143
Asp Pro Lys Pro Asp Glu Leu His Lys Ser Ser Lys Phe Thr Gly Leu
        35                  40                  45 atg gag aac atg aag gtg ctc tat gat gac aac cat gtg tca gca atc      191
Met Glu Asn Met Lys Val Leu Tyr Asp Asp Asn His Val Ser Ala Ile
    50                  55                  60 aat gtg aag tct att gac caa tcc ctc tac ttt gac ctc atc tac tct      239
Asn Val Lys Ser Ile Asp Gln Ser Leu Tyr Phe Asp Leu Ile Tyr Ser
65                  70                  75 atc aag gac act aag ttg gga aac tat gac aat gtg agg gtg gag ttc      287
Ile Lys Asp Thr Lys Leu Gly Asn Tyr Asp Asn Val Arg Val Glu Phe
80                  85                  90                  95 aag aac aag gac ttg gct gac aag tac aag gac aag tat gtg gat gtg      335
Lys Asn Lys Asp Leu Ala Asp Lys Tyr Lys Asp Lys Tyr Val Asp Val
                100                 105                 110 ttt gga gct aac tac tat tac caa tgc tac ttc tct aag aaa acc aat      383
Phe Gly Ala Asn Tyr Tyr Tyr Gln Cys Tyr Phe Ser Lys Lys Thr Asn
            115                 120                 125
```

-continued

```
gac atc aac agc cac caa act gac aag aga aag act tgc atg tat ggt       431
Asp Ile Asn Ser His Gln Thr Asp Lys Arg Lys Thr Cys Met Tyr Gly
            130                 135                 140 ggt gtg act gag cac aac gga aac caa ttg gac aaa tac agg agc atc       479
Gly Val Thr Glu His Asn Gly Asn Gln Leu Asp Lys Tyr Arg Ser Ile
145                 150                 155 act gtg agg gtg ttt gag gat ggt aag aac ctc ctc tct ttt gat gtg       527
Thr Val Arg Val Phe Glu Asp Gly Lys Asn Leu Leu Ser Phe Asp Val
160                 165                 170                 175 caa act aac aag aag aag gtg act gct caa gag ttg gac tac ctc act       575
Gln Thr Asn Lys Lys Lys Val Thr Ala Gln Glu Leu Asp Tyr Leu Thr
                180                 185                 190 agg cac tac ttg gtg aag aac aag aag ctc tat gag ttc aac aac agc       623
Arg His Tyr Leu Val Lys Asn Lys Lys Leu Tyr Glu Phe Asn Asn Ser
            195                 200                 205 cct tat gag act gga tac atc aag ttc att gag aat gag aac agc ttc       671
Pro Tyr Glu Thr Gly Tyr Ile Lys Phe Ile Glu Asn Glu Asn Ser Phe
        210                 215                 220 tgg tat gac atg atg cct gca cca gga gac aag ttt gac caa tct aag       719
Trp Tyr Asp Met Met Pro Ala Pro Gly Asp Lys Phe Asp Gln Ser Lys
    225                 230                 235 tac ctc atg atg tac aat gac aac aag atg gtg gac tct aag gat gtg       767
Tyr Leu Met Met Tyr Asn Asp Asn Lys Met Val Asp Ser Lys Asp Val
240                 245                 250                 255 aag att gag gtg tac ctt acc acc aag aag aag taa gtcttcgagc tc         815
Lys Ile Glu Val Tyr Leu Thr Thr Lys Lys Lys
                260                 265
```

<210> SEQ ID NO 8
<211> LENGTH: 266
<212> TYPE: PRT
<213> ORGANISM: bean yellow dwarf virus

<400> SEQUENCE: 8

```
Met Asp Lys Arg Leu Phe Ile Ser His Val Ile Leu Ile Phe Ala Leu
1               5                   10                  15

Ile Leu Val Ile Ser Thr Pro Asn Val Leu Ala Glu Ser Gln Pro Asp
            20                  25                  30

Pro Lys Pro Asp Glu Leu His Lys Ser Ser Lys Phe Thr Gly Leu Met
        35                  40                  45

Glu Asn Met Lys Val Leu Tyr Asp Asp Asn His Val Ser Ala Ile Asn
    50                  55                  60

Val Lys Ser Ile Asp Gln Ser Leu Tyr Phe Asp Leu Ile Tyr Ser Ile
65                  70                  75                  80

Lys Asp Thr Lys Leu Gly Asn Tyr Asp Asn Val Arg Val Glu Phe Lys
                85                  90                  95

Asn Lys Asp Leu Ala Asp Lys Tyr Lys Asp Lys Tyr Val Asp Val Phe
            100                 105                 110

Gly Ala Asn Tyr Tyr Gln Cys Tyr Phe Ser Lys Lys Thr Asn Asp
        115                 120                 125

Ile Asn Ser His Gln Thr Asp Lys Arg Lys Thr Cys Met Tyr Gly Gly
    130                 135                 140

Val Thr Glu His Asn Gly Asn Gln Leu Asp Lys Tyr Arg Ser Ile Thr
145                 150                 155                 160

Val Arg Val Phe Glu Asp Gly Lys Asn Leu Leu Ser Phe Asp Val Gln
                165                 170                 175

Thr Asn Lys Lys Lys Val Thr Ala Gln Glu Leu Asp Tyr Leu Thr Arg
```

```
                180              185             190
His Tyr Leu Val Lys Asn Lys Lys Leu Tyr Glu Phe Asn Asn Ser Pro
            195             200             205

Tyr Glu Thr Gly Tyr Ile Lys Phe Ile Glu Asn Glu Asn Ser Phe Trp
    210             215             220

Tyr Asp Met Met Pro Ala Pro Gly Asp Lys Phe Asp Gln Ser Lys Tyr
225             230             235             240

Leu Met Met Tyr Asn Asp Asn Lys Met Val Asp Ser Lys Asp Val Lys
            245             250             255

Ile Glu Val Tyr Leu Thr Thr Lys Lys
            260             265
```

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:Peptide
      signal which targets nascent protein to the endoplasmic
      reticulum.

<400> SEQUENCE: 9

Lys Asp Glu Leu
  1

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:Peptide
      signal which targets nascent protein to the endoplasmic
      reticulum.

<400> SEQUENCE: 10

Ser Glu Lys Asp Glu Leu
  1               5

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence:Primer for
      amplifying a GFP expression cassette.

<400> SEQUENCE: 11
agctcgacca ggatgg                                                  16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence:Primer for
      amplifying a GFP expression cassette.

<400> SEQUENCE: 12
gtcctgctgg agttcg                                                  16

<210> SEQ ID NO 13
<211> LENGTH: 30
<212> TYPE: DNA
<213> ORGANISM: Artificial Sequence
<220> FEATURE:

```
<223> OTHER INFORMATION: Description of Artificial Sequence:Primer for
      amplifying SIR of BYDV.

<400> SEQUENCE: 13

-continued amplifying a form of the BYDV Rep gene.

<400> SEQUENCE: 19
cggataacaa tttcacacag                                            20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:Primer for
      amplifying a form of the BYDV Rep gene.

<400> SEQUENCE: 20
ctcagctaat taagctta                                              18

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence:Primer for
      mutagenesis of Rep C1 gene.

<400> SEQUENCE: 21
ccttgtatta gggtccttct tttttcg                                    27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:Primer for
      mutagenesis of Rep C1 gene.

<400> SEQUENCE: 22
cgaaaaaaga aggaccctaa tacaagg                                    27

What is claimed is:

1. A pair of recombinant nucleic acid molecules wherein a first molecule comprises at least a portion of a long intergenic region (LIR) of a geminivirus genome, wherein said first molecule lacks a functional geminiviral coat protein encoding sequence and further comprises an SIR; and a second molecule comprising a geminiviral replicase gene operably linked to a fruit ripening-dependent promoter.

2. The pair of recombinant nucleic acid molecules of claim 1, wherein said first molecule further comprises a plant-functional promoter.

3. The pair of recombinant nucleic acid molecules of claim 1, wherein said first molecule further comprises a gene of interest.

4. The pair of recombinant nucleic acid molecules of claim 1, wherein the said first molecule comprises a heterologous gene.

5. The pair of recombinant nucleic acid molecules of claim 3, wherein said gene of interest of said first DNA molecule is selected from the group consisting of a gene encoding luciferase, glucuronosidase (GUS), green fluorescent protein (GFP), shigatoxin B (StxB), staphylococcus enterotoxin B (SEB), *E. coli* labile toxin B (LT-B), Norwalk virus capsid protein (NVCP), and hepatitis B surface antigen (HBsAg).

6. The pair of recombinant nucleic acid molecules of claim 1, wherein said first molecule further comprises a plant-functional termination sequence.

7. The pair of recombinant nucleic acid molecules of claim 1 wherein said first molecule is single stranded.

8. The pair of recombinant nucleic acid molecules of claim 2, wherein said plant-functional promoter is selected from the group consisting of CaMV 35S, tomato E8, patatin, ubiquitin, mannopine synthase (mas), rice actin 1, soybean seed protein glycinin (Gy1) and soybean vegetative storage protein (vsp).

9. The pair of recombinant nucleic acid molecules of claim 6, wherein said plant-functional termination sequence is selected from the group consisting of nopaline synthase (nos), vegetative storage protein (vsp), pin2, and geminiviral short intergenic (sir) termination sequences.

10. A recombinant nucleic acid molecule comprising at least a portion of a long intergenic region (LIR) of a geminivirus genome and her comprising an SIR, and a geminiviral replicase gene operably linked to a fruit ripening-dependent promoter.

11. The recombinant nucleic acid molecule of claim 10 further comprising a plant-functional promoter.

12. The recombinant nucleic acid molecule of claim 10 further comprising a gene of interest.

13. The recombinant nucleic acid molecule of claim 10, further comprises a heterologous gene.

14. The recombinant nucleic acid molecule of claim 10, further comprising a plant-functional termination sequence.

15. The recombinant nucleic acid molecule of claim 10, wherein the geminiviral replicase gene is optimized for expression in plants by having at least one codon degenerate to a corresponding codon of the native protein encoding sequence.

16. The recombinant nucleic acid molecule of claim 10, which is single stranded.

17. The recombinant nucleic acid molecule of claim 11, wherein said plant-functional promoter is selected from the group consisting of CaMV 35S, tomato E8, patatin, ubiquitin, mannopine synthase (mas), rice actin 1, soybean seed protein glycinin (Gy1) and soybean vegetative storage protein (vsp).

18. The recombinant nucleic acid molecule of claim 13, wherein the said heterologous gene is selected from the group consisting of a gene encoding luciferase, glucuronosidase (GUS), green fluorescent protein (GFP), shigatoxin B (StxB), staphylococcus enterotoxin B (SEB), *E. coli* labile toxin B (LT-B), Norwalk virus capsid protein (NVCP), and hepatitis B surface antigen (HbsAg).

19. The recombinant nucleic acid molecule of claim 14, wherein said plant-functional termination sequence is selected from the group consisting of nopaline synthase (nos), vegetative storage protein (vsp), pin2, and geminiviral short intergenic (sir) termination sequences.

20. An expression vector comprising a selectable marker gene, at least a portion of a long intergenic region (LIR) of a geminivirus genome, an SIR, a restriction site for insertion of a gene of interest, and a functional geminiviral replicase gene operably linked to a fruit ripening-dependent promoter and wherein said nucleic acid sequence lacks a functional geminiviral coat protein encoding sequence.

21. The vector of claim 20, further comprising a gene of interest.

22. The vector of claim 20, further comprising a heterologous gene operably linked to a fruit ripening-dependent promoter.

23. The vector of claim 20, wherein said gene of interest is flanked by two LIR portions.

24. The vector of claim 20, wherein the 5' end of said gene of interest is operably linked to a plant-functional promoter sequence.

25. The vector of claim 20, wherein said gene of interest is selected from the group consisting of a gene encoding luciferase, glucuronosidase (GUS), green fluorescent protein (GFP), shigatoxin B (StxB), staphylococcus enterotoxin B (SEB), labile toxin B (LT-B), Norwalk virus capsid protein (NVCP), and hepatitis B surface antigen (HbsAg).

26. The vector of claim 20, wherein the 3' end of the gene of interest is operably linked to a plant-functional termination sequence.

27. The vector of claim 20, further comprising an *E. coli* origin of replication.

28. The vector of claim 20, wherein the inserted gene of interest is flanked by left and right T-DNA border regions of *Agrobacterium tumefaciens*.

29. The vector of claim 27, further comprising an *Agrobacterium tumefaciens* origin of replication.

30. A strain of *E. coli* transfected with the expression vector of claim 27.

31. A strain of *Agrobacterium tumefaciens* transfected with the expression vector of claim 29.

32. The strain of claim 31, further comprising a helper tumor-inducing (Ti) plasmid.

33. An expression vector comprising a selectable marker gene, at least a portion of a long intergenic region (LIR) of a geminivirus genome, an SIR, a restriction site for insertion of a gene of interest, and a fruit ripening-dependent promoter and wherein said nucleic acid sequence lacks a functional geminiviral coat protein encoding sequence.

34. A transgenic plant cell transformed with a nucleic acid having at least a portion of a long intergenic region (LIR) of a geminivirus genome, an SIR, a gene of interest, wherein said nucleic acid lacks a functional geminiviral coat protein encoding sequence.

35. The transgenic plant cell of claim 34, further comprising a heterologous gene.

36. The transgenic plant cell of claim 34, wherein said nucleic acid lacks a functional geminiviral replicase gene.

37. The transgenic plant cell of claim 34, wherein the nucleic acid is present in nuclear episomes in the cell.

38. The transgenic plant cell of claim 34, wherein the 5' end of said gene of interest is operably linked to a plant-functional promoter sequence.

39. The transgenic plant cell of claim 34, wherein said gene of interest is selected from the group consisting of a gene encoding luciferase, glucuronosidase (GUS), green fluorescent protein (GFP), shigatoxin B (StxB), staphylococcus enterotoxin B (SEB), labile toxin B (LT-B), Norwalk virus capsid protein (NVCP), and hepatitis B surface antigen (HBsAg).

40. The transgenic plant cell of claim 34, wherein the 3' end of said gene of interest is operably linked to a plant-functional termination sequence.

41. The transgenic plant cell of claim 34, further comprising a viral replicase encoding sequence operably linked to a plant functional promoter and a termination sequence.

42. The transgenic plant cell of claim 34, wherein the gene of interest is the viral replicase gene operably linked to an inducible promoter.

43. The transgenic plant cell of claim 34, wherein the gene of interest is the viral replicase gene operably linked at the 5' end to a tissue-specific promoter.

44. The transgenic plant cell of claim 41, wherein the viral replicase encoding sequence encodes a wild-type geminiviral replicase.

45. The transgenic plant cell of claim 41, wherein the viral replicase encoding sequence is provided as part of an expression cassette or part of a nucleic acid molecule comprising a viral replicon.

46. The transgenic plant cell of claim 43, wherein the tissue-specific promoter is selected from the group consisting of glucocorticoid, estrogen, jasmonic acid, insecticide RH5992, copper, tetracycline, and alcohol-inducible promoters.

47. A transgenic plant cell transformed with a nucleic acid comprising at least a portion of a long intergenic region (LIR) of a geminivirus genome, an SIR, a restriction site for of insertion of a gene of interest, and a functional geminiviral replicase gene operably linked to a fruit ripening-dependent promoter and wherein said nucleic acid sequence lacks a functional geminiviral coat protein encoding sequence.

48. A transgenic plant seed transformed with a nucleic acid having at least a portion of a long intergenic region (LIR) of a geminivirus genome, an SIR, a gene of interest, wherein said nucleic acid lacks a functional geminiviral coat protein encoding sequence.

49. The seed of claim 43, further comprising a heterologous gene.

50. A transgenic plant seed transformed with a nucleic acid comprising at least a portion of a long intergenic region (LIR) of a geminivirus genome, an SIR, a restriction site for insertion of a gene of interest, and a functional geminiviral replicase gene operably linked to a fruit ripening-dependent promoter and wherein said nucleic acid sequence lacks a functional geminiviral coat protein encoding sequence.

51. The seed of claim 49, wherein said nucleic acid lacks a functional geminiviral replicase gene.

52. The seed of claim 49, further comprising a viral replicase encoding sequence expressed in trans with said nucleotide sequence.

53. The seed of claim 49, which is selected from the group consisting of tobacco, tomato, potato, banana, soybean, pepper, wheat, rye, rice, spinach, carrot, and maize.

54. The seed of claim 52, wherein the 5' end of the viral replicase encoding sequence is operably linked to a tissue-specific promoter.

55. A method of transforming a plant cell comprising contacting the plant cell with a strain of *Agrobacterium tumefaciens* as in claim 31 under conditions effective to transfer and integrate said nucleic acid sequence into the nuclear genome of the cell.

56. A method of producing a transgenic plant comprising transforming a plant cell as in claim 55 and regenerating a plant from the plant cell.

57. A method of amplifying a heterologous nucleotide sequence in a transgenic plant comprising subjecting the transgenic plant of claim 56 to a wild-type geminivirus, which, expresses a viral replicase in planta that rescues and replicates said nucleotide sequence in cells of said plant.

58. A method of overproducing a protein in a plant comprising subjecting the transgenic plant of claim 56 to a wild-type geminivirus, which expresses a viral replicase in planta that rescues and replicates said nucleic acid sequence in said plant.

59. A method of amplifying a heterologous nucleotide sequence in a transgenic plant comprising subjecting the transgenic plant of claim 56 to a chemical or developmental agent, which induces expression of a viral replicase in planta that rescues and replicates said nucleotide sequence in said plant.

60. A method of overproducing a protein in a plant, comprising subjecting the transgenic plant of claim 56 to a chemical or developmental agent, which induces expression of a viral replicase in planta that rescues and replicates said nucleic acid sequence in said plant.

61. A method of transforming a plant cell comprising subjecting the plant cell to microparticle bombardment with solid particles loaded with a DNA construct as in claim 1 under conditions effective to transfer and integrate said nucleic acid sequence into the nuclear genome of the cell.

62. A method of producing a transgenic plant comprising transforming a plant cell as in claim 61 and regenerating a plant from the plant cell.

63. The method of claim 59, wherein the viral replicase is operably linked to an inducible promoter selected from the group consisting of glucocorticoid, estrogen, and alcohol-inducible promoters.

64. The method of claim 59, wherein replication of said viral replicase is expressed in trans with said nucleotide sequence.

65. A transgenic plant cell transformed with a nucleic acid comprising a SIR and a functional geminiviral replicase gene operably linked to a fruit ripening-dependent promoter.

66. A transgenic plant seed transformed with a nucleic acid comprising a SIR and a functional geminiviral replicase gene operably linked to a fruit ripening-dependent promoter.

* * * * *